(12) United States Patent
Sato et al.

(10) Patent No.: US 9,750,474 B2
(45) Date of Patent: Sep. 5, 2017

(54) IMAGE REGION MAPPING DEVICE, 3D MODEL GENERATING APPARATUS, IMAGE REGION MAPPING METHOD, AND IMAGE REGION MAPPING PROGRAM

(71) Applicant: Panasonic Corporation, Osaka (JP)

(72) Inventors: Taichi Sato, Kyoto (JP); Toru Nakada, Kyoto (JP)

(73) Assignee: PANASONIC CORPORATION, Osaka (JP)

(*) Notice: Subject to any disclaimer, the term of this patent is extended or adjusted under 35 U.S.C. 154(b) by 242 days.

(21) Appl. No.: 14/827,634

(22) Filed: Aug. 17, 2015

(65) Prior Publication Data
US 2015/0351713 A1 Dec. 10, 2015

Related U.S. Application Data

(63) Continuation of application No. PCT/JP2014/001926, filed on Apr. 2, 2014.

(30) Foreign Application Priority Data

Apr. 5, 2013 (JP) ................. 2013-079218

(51) Int. Cl.
*A61B 6/00* (2006.01)
*A61B 6/02* (2006.01)

(52) U.S. Cl.
CPC .............. *A61B 6/504* (2013.01); *A61B 6/481* (2013.01); *A61B 6/5235* (2013.01); *A61B 6/022* (2013.01); *A61B 6/547* (2013.01)

(58) Field of Classification Search
CPC ....... A61B 6/504; A61B 6/4441; A61B 6/481; A61B 6/022; A61B 6/4014; A61B 6/4266; A61B 6/486; A61B 6/4007; G01N 23/04
See application file for complete search history.

(56) References Cited

U.S. PATENT DOCUMENTS

| 6,169,917 B1 | 1/2001 | Masotti et al. |
| 2006/0250386 A1 | 11/2006 | Movassaghi et al. |

(Continued)

FOREIGN PATENT DOCUMENTS

| JP | 8-131429 | 5/1996 |
| JP | 10-5203 | 1/1998 |

(Continued)

OTHER PUBLICATIONS

International Preliminary Report on Patentability and Written Opinion issued Oct. 6, 2015 in International Application No. PCT/JP2014/001925. (English Translation).

(Continued)

*Primary Examiner* — Hoon Song
(74) *Attorney, Agent, or Firm* — Wenderoth, Lind & Ponack, L.L.P.

(57) ABSTRACT

An X-ray image acquiring unit, by irradiating a blood vessel through which contrast medium is passing with X-rays of equal intensity at first and second photographing angles, acquires first and second X-ray images. An absorption property acquiring unit acquires, from brightness of the contrast medium, an X-ray absorption property in a first image region corresponding to a portion of the blood vessel in the first X-ray image. An absorption property acquiring unit acquires, from brightness of the contrast medium, an X-ray absorption property of each of plural second image regions corresponding to a portion of the blood vessel in the second X-ray image as candidate corresponding image regions of the first image region. A similarity degree calculator calculates a similarity degree between the acquired absorption properties. A corresponding region determiner determines the second image region having the maximum similarity degree as a corresponding region of the first image region.

13 Claims, 54 Drawing Sheets

(56) References Cited

U.S. PATENT DOCUMENTS

2007/0195932 A1* 8/2007 Nakaura ................ A61B 6/504
378/98.12
2008/0205722 A1 8/2008 Schaefer et al.
2012/0148135 A1* 6/2012 Van Rens ............... G06T 7/194
382/131
2012/0155737 A1* 6/2012 Sakaguchi ............. A61B 5/055
382/132

FOREIGN PATENT DOCUMENTS

| | | |
|---|---|---|
| JP | 2004-201730 | 7/2004 |
| JP | 2007-502644 | 2/2007 |
| JP | 2008-6083 | 1/2008 |
| JP | 2009-504297 | 2/2009 |
| JP | 2013-501567 | 1/2013 |
| WO | 2006/051831 | 5/2006 |

OTHER PUBLICATIONS

International Preliminary Report on Patentability and Written Opinion issued Oct. 6, 2015 in International Application No. PCT/JP2014/001926. (English Translation).
International Search Report issued May 13, 2014 in International (PCT) Application No. PCT/JP2014/001926, with English translation.
Guy Shechter et al., "Three-Dimensional Motion Tracking of Coronary Arteries in Biplane Cineangiograms", IEEE Transactions on Medical Imaging, vol. 22, No. 4, Apr. 2003, pp. 493-503.
Tadahiro Yoshida et al., "Detection of Three Dimensional Coronary Arterial Tree from Biplane Cineangiogram", The Journal of the Institute of Electronics, Information and Communication Engineers, vol. J72-D-II, No. 3, Mar. 1989, pp. 433-441, with partial English translation.

* cited by examiner

*Fig.9*

| TRANSLATION VECTOR T | (T_X, T_Y, T_Z) |
|---|---|
| ROTATION VECTOR R | $\begin{pmatrix} R\_0\_0, R\_0\_1, R\_0\_2 \\ R\_1\_0, R\_1\_1, R\_1\_2 \\ R\_2\_0, R\_2\_1, R\_2\_2 \end{pmatrix}$ |
| INTERNAL PARAMETER A1 | $\begin{pmatrix} A1\_0\_0, A1\_0\_1, A1\_0\_2 \\ A1\_1\_0, A1\_1\_1, A1\_1\_2 \\ A1\_2\_0, A1\_2\_1, A1\_2\_2 \end{pmatrix}$ |
| INTERNAL PARAMETER A2 | $\begin{pmatrix} A2\_0\_0, A2\_0\_1, A2\_0\_2 \\ A2\_1\_0, A2\_1\_1, A2\_1\_2 \\ A2\_2\_0, A2\_2\_1, A2\_2\_2 \end{pmatrix}$ |

*Fig.10*

|  | RADIOGRAPHING UNIT 101 | RADIOGRAPHING UNIT 102 |
|---|---|---|
| TIME 0 | IMAGE 1_0 | IMAGE 2_0 |
| TIME 1 | IMAGE 1_1 | IMAGE 2_1 |
| ⋮ | ⋮ | ⋮ |
| TIME END | IMAGE 1_END | IMAGE 2_END |

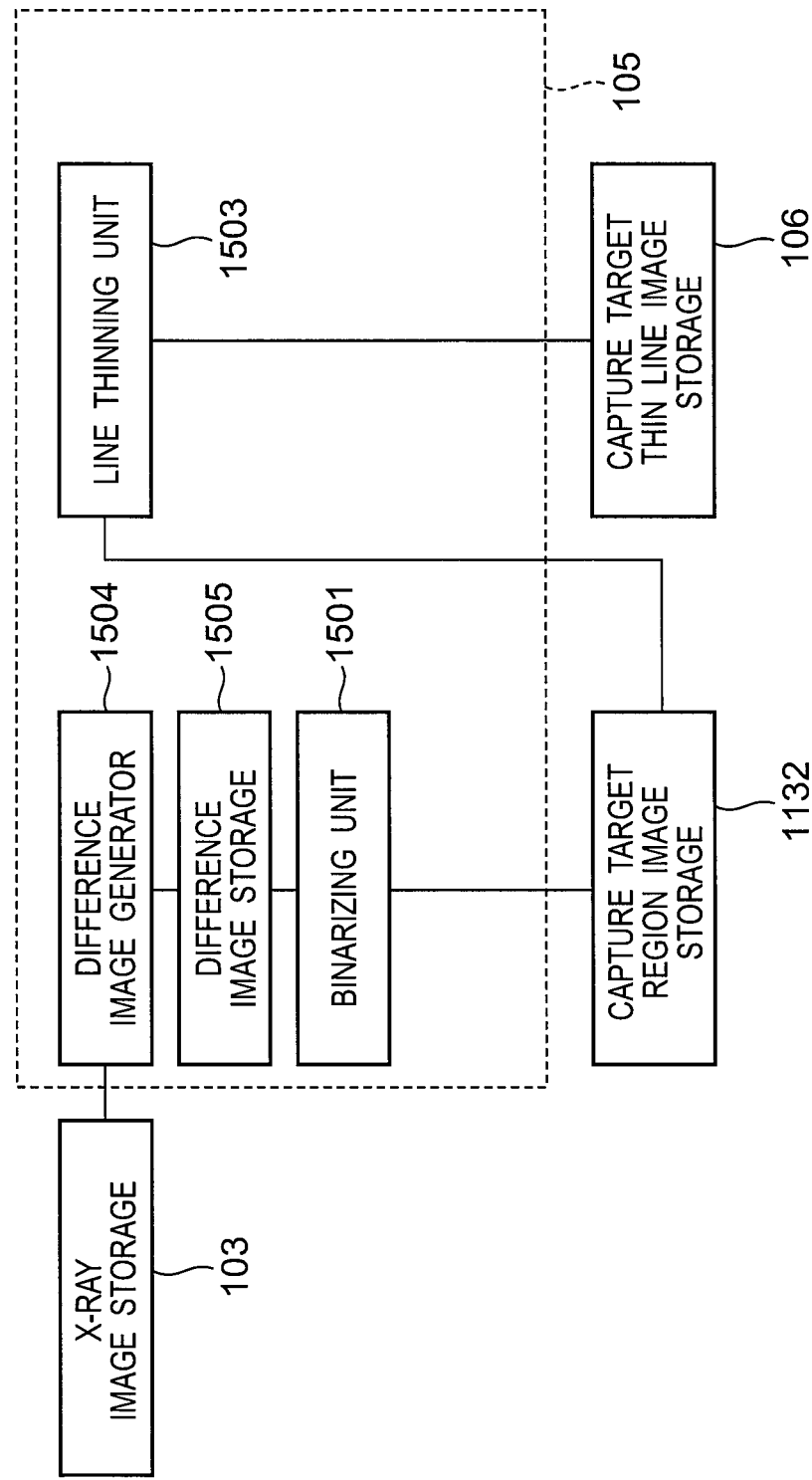

| 1 | (100, 200), (101, 200), ···, (113, 200), |
|---|---|
| 2 | (800, 200), (801, 200), ···, (110, 200), |

|  | Pk | Qk_1 | Qk_2 |
|---|---|---|---|
| TIME 0 | $\lambda\_Pk\_0$ | $\lambda\_Qk\_1\_0$ | $\lambda\_Qk\_2\_0$ |
| TIME 1 | $\lambda\_Pk\_1$ | $\lambda\_Qk\_1\_1$ | $\lambda\_Qk\_2\_1$ |
| ... | ... | ... | ... |
| TIME T_END | $\lambda\_Pk\_END$ | $\lambda\_Qk\_1\_END$ | $\lambda\_Qk\_2\_END$ |

Fig.30

|  | COORDINATES OF CONTRAST POINT Pk | COORDINATES OF CORRESPONDING POINT Qk | EVALUATION VALUE FOR CORRESPONDING POINT Qk |
|---|---|---|---|
| FIRST POINT | $(P1\_X, P1\_Y)$ | $(Q1\_X, Q1\_Y)$ | $H1$ |
| SECOND POINT | $(P2\_X, P2\_Y)$ | $(Q2\_X, Q2\_Y)$ | $H2$ |
| ⋮ | ⋮ | ⋮ | ⋮ |
| $K^{TH}$ POINT | $(PK\_X, PK\_Y)$ | $(QK\_X, QK\_Y)$ | $HK$ |

Fig.31

|  | COORDINATES OF 3D POINT Jk |
|---|---|
| FIRST POINT | $(J1\_X, J1\_Y, J1\_Z)$ |
| SECOND POINT | $(J2\_X, J2\_Y, J2\_Z)$ |
| ⋮ | ⋮ |
| $K^{TH}$ POINT | $(JK\_X, JK\_Y, JK\_Z)$ |

*Fig.51*

| 1 | [ {1,2}, {1} ] | FIG. 42 |
|---|---|---|
| 2 | [ {1,2}, {2} ] | FIG. 45 |
| 3 | [ {1,3}, {1} ] | FIG. 47 |
| 4 | [ {1,3}, {2} ] | FIG. 48 |
| 5 | [ {1}, {1} ] | FIG. 44 |
| 6 | [ {1}, {2} ] | FIG. 46 |

Fig.53

| No \ ID | F1 | F2 | F3 | S1 | S2 |
|---|---|---|---|---|---|
| 1 | 0 | 0 | 0 | 0 | 1 |
| 2 | 0 | 0 | 0 | 1 | 0 |
| 3 | 0 | 0 | 0 | 1 | 1 |
| 4 | 0 | 0 | 1 | 0 | 0 |
| ... | ... | ... | ... | ... | ... |
| 10 | 0 | 1 | 0 | 1 | 0 |
| 11 | 0 | 1 | 0 | 1 | 1 |
| 12 | 0 | 1 | 1 | 0 | 0 |
| 13 | 0 | 1 | 1 | 0 | 1 |
| 14 | 0 | 1 | 1 | 1 | 0 |
| 15 | 0 | 1 | 1 | 1 | 1 |

Fig.54

| No \ c | GROUP 0 | GROUP 1 |
|---|---|---|
| 1 | [ {F1, F2, F3}, {S1} ] | [ {}, {S2} ] |
| 2 | [ {F1, F2, F3}, {S2} ] | [ {}, {S1} ] |
| 3 | [ {F1, F2, F3}, {} ] | [ {}, {S1, S2} ] |
| 4 | [ {F1, F2}, {S1, S2} ] | [ {F3}, {} ] |
| 5 | [ {F1, F2}, {S2} ] | [ {F3}, {S1} ] |
| 6 | [ {F1, F2}, {S1} ] | [ {F3}, {S2} ] |
| 7 | [ {F1, F2}, {} ] | [ {F3}, {S1, S2} ] |
| 8 | [ {F1, F3}, {S1, S2} ] | [ {F3}, {} ] |
| 9 | [ {F1, F3}, {S1} ] | [ {F3}, {S2} ] |
| 10 | [ {F1, F3}, {S2} ] | [ {F2}, {S1} ] |
| 11 | [ {F1, F3}, {} ] | [ {F2}, {S1, S2} ] |
| 12 | [ {F1}, {S1, S2} ] | [ {F2, F3}, {} ] |
| 13 | [ {F1}, {S1} ] | [ {F2, F3}, {S2} ] |
| 14 | [ {F1}, {S2} ] | [ {F2, F3}, {S1} ] |
| 15 | [ {F1}, {} ] | [ {F2, F3}, {S1, S2} ] |

Fig.56

| No | GROUPING |
|---|---|
| 1 | [ {1, 2}, {2} ] |
| 2 | [ {1, 2}, {1} ] |
| 3 | [ {1, 3}, {1} ] |
| 4 | [ {1, 3}, {2} ] |
| 5 | [ {1}, {1} ] |
| 6 | [ {1}, {2} ] |

Fig.59

|  | COORDINATES OF CONTRAST POINT Pk | COORDINATES OF CORRESPONDING POINT Qk | EVALUATION VALUE |
|---|---|---|---|
| FIRST POINT | (Pk_1_X, Pk_1_Y) | (Qk_1_X, Qk_1_Y) | $H\alpha$ |
| SECOND POINT | (Pk_2_X, Pk_2_Y) | (Qk_1_X, Qk_1_Y) | $H\alpha$ |

Fig.60

|  | COORDINATES OF CONTRAST POINT Pk | COORDINATES OF CORRESPONDING POINT Qk | EVALUATION VALUE |
|---|---|---|---|
| FIRST POINT | (Pk_1_X, Pk_1_Y) | (Qk_1_X, Qk_1_Y) | $H\alpha$ |
| SECOND POINT | (Pk_1_X, Pk_1_Y) | (Qk_2_X, Qk_2_Y) | $H\alpha$ |

IMAGE REGION MAPPING DEVICE, 3D MODEL GENERATING APPARATUS, IMAGE REGION MAPPING METHOD, AND IMAGE REGION MAPPING PROGRAM

CROSS-REFERENCE TO RELATED APPLICATIONS

This is a continuation application of International Application No. PCT/JP2014/001926, with an international filing date of Apr. 2, 2014, which claims priority of Japanese Patent Application No. 2013-079218 filed on Apr. 5, 2013, the content of which is incorporated herein by reference.

TECHNICAL FIELD

The technical field relates to an image region mapping device configured to map a plurality of image regions in X-ray images of a blood vessel captured in two directions, a 3D model generating apparatus configured to generate a 3D model of the blood vessel using the image region mapping device, an image region mapping method, and an image region mapping program.

BACKGROUND ART

A catheter angiography examination exemplifies an examination of a disease caused by angiostenosis or vascular occlusion. The catheter angiography examination requires use of a contrast medium made of a radiopaque material. Injection of the contrast medium into a blood vessel to radiograph the blood vessel can clearly distinguish the blood vessel from other portions.

It is difficult for a person to grasp the shape of a blood vessel like a coronary artery having a large number of bifurcations with an image radiographed in one direction.

Research and development have been made on a technique of generating a 3D model of a blood vessel from two X-ray images captured in two directions (see Patent Literature 1 and Non-Patent Literature 1, for example). This technique enables a person to easily grasp the shape of a blood vessel.

CITATION LIST

Patent Literature

Patent Literature 1: JP 08-131429 A

Non-Patent Literature

Non-Patent Literature 1: Tadahiro YOSHIDA, Motohide MISAKI, Hiroyasu SATO, Tsuneo SAITO "Detection of Three Dimensional Coronary Arterial Tree from Biplane Cineangiogram", The Journal of the Institute of Electronics, Information and Communication Engineers, 89/3 Vol. J72-D-II No. 3, pp. 433-441

SUMMARY OF THE INVENTION

The conventional technique was, however, insufficient for generation of a 3D model of a blood vessel.

In view of the above, a non-limitative exemplary embodiment of the present disclosure provides an image region mapping device configured to map a plurality of image regions in X-ray images of a blood vessel captured in two directions, a 3D model generating apparatus configured to generate a 3D model of the blood vessel using the image region mapping device, an image region mapping method, and an image region mapping program.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

In one general aspect, the techniques disclosed here feature: An image region mapping device configured to map a plurality of image regions of a blood vessel, the device comprising:

an X-ray image acquiring unit configured to, by irradiating the blood vessel through which a contrast medium is passing with X-rays at first and second photographing angles different from each other, acquire an X-ray image set including a first X-ray image at the first photographing angle and a second X-ray image at the second photographing angle;

a first X-ray absorption property acquiring unit configured to acquire, as an absorption property, an absorbed X-ray amount in a first image region corresponding to a portion of the blood vessel in the first X-ray image, from brightness of the contrast medium;

a second X-ray absorption property acquiring unit configured to acquire, as an absorption property, an absorbed X-ray amount in each of a plurality of second image regions corresponding to a portion of the blood vessel in the second X-ray image as candidate corresponding image regions of the first image region, from brightness of the contrast medium;

a similarity degree calculator configured to calculate a similarity degree between the absorbed X-ray amount acquired by the first X-ray absorption property acquiring unit and each of the plurality of absorbed X-ray amounts acquired by the second X-ray absorption property acquiring unit; and a corresponding region determiner configured to determine one of the second image regions corresponding to the first image region in accordance with the similarity degrees calculated by the similarity degree calculator.

These general and specific aspects may be implemented using a system, a method, and a computer program, and any combination of systems, methods, and computer programs.

According to the non-limitative exemplary embodiment of the present disclosure, there is provided an image region mapping device configured to map a plurality of image regions in X-ray images of a blood vessel captured in two directions, a 3D model generating apparatus configured to generate a 3D model of the blood vessel using the image region mapping device, an image region mapping method, and an image region mapping program.

BRIEF DESCRIPTION OF THE DRAWINGS

These and other aspects and features of the present disclosure will become clear from the following description taken in conjunction with the embodiments thereof with reference to the accompanying drawings, in which:

FIG. 9 is a chart of a data structure in a radiographing unit information storage according to the second embodiment;

FIG. 10 is a chart of a data structure in an X-ray image storage according to the second embodiment;

FIG. 11 is a view of the configuration of a capture target region acquiring unit according to the second embodiment;

FIG. 27 is a chart of a data structure in an absorption property storage according to the second embodiment;

FIG. 30 is a chart of a data structure in the second image projection region storage according to the second embodiment;

FIG. 31 is a chart of a data structure in a 3D position storage according to the second embodiment;

FIG. 51 is an exemplary chart of grouping acquired by a grouping acquiring unit according to the third embodiment;

FIG. 53 is an exemplary chart of grouping performed by a two-grouping unit according to the third embodiment;

FIG. 54 is a chart of a grouping result of the two-grouping unit according to the third embodiment;

FIG. 56 is an exemplary chart of a grouping result of the grouping unit according to the third embodiment;

FIG. 59 is an exemplary chart of corresponding information added to a corresponding information storage according to the third embodiment;

FIG. 60 is an exemplary chart of corresponding information added to the corresponding information storage according to the third embodiment.

DETAILED DESCRIPTION

Figure 1:
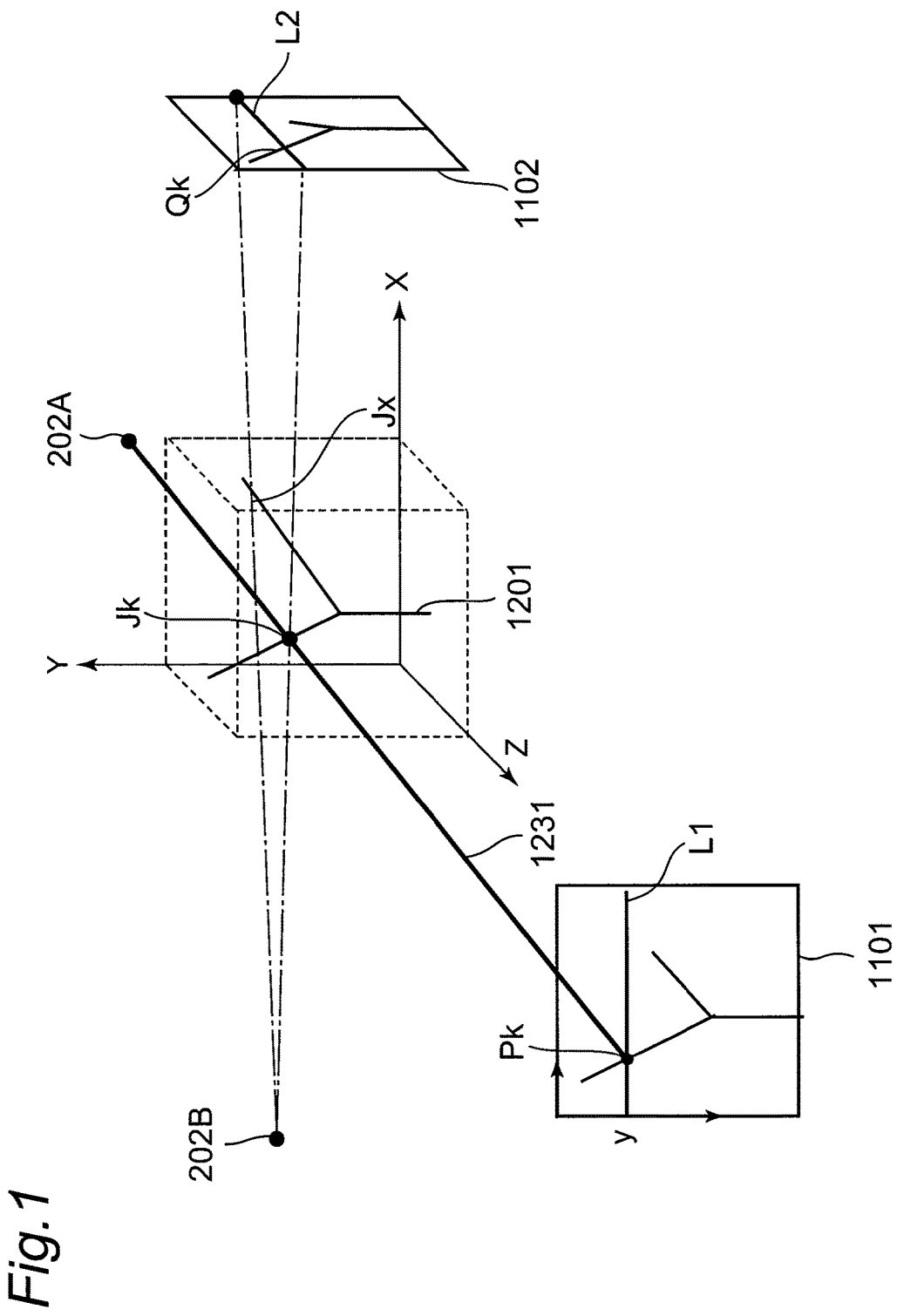
FIG. 1 is an explanatory view of generation of a 3D model of a blood vessel.

Before the description of the present disclosure proceeds, the same components are denoted by the same reference numerals in the attached drawings.

Before describing the embodiments according to the present disclosure with reference to the drawings, findings which are a basis for the present disclosure will be described.

(Finding as the Basis of the Disclosure)

FIG. 1 is an explanatory view of generation of a 3D model of a blood vessel.

X-ray generators (generating units) 202A and 202B irradiate a blood vessel 1201 with X-rays in two different directions to obtain first and second X-ray images 1101 and 1102, respectively.

The blood vessel 1201 includes a point Jk corresponding to a point Pk on the first X-ray image 1101.

When the point Jk can be specified in position on the second X-ray image 1102, the point Jk can be specified in 3D position in accordance with the triangulation principle. Similarly, a 3D model of the blood vessel 1201 can be generated by specifying in 3D position a plurality of points on the blood vessel 1201.

Described below is a method of obtaining a point on the second X-ray image 1102 corresponding to the point Jk.

Initially obtained is an epipolar line L2 in the second X-ray image 1102 for the point Pk on the first X-ray image 1101. The epipolar line L2 indicates a linear range in which a corresponding point of the point Pk possibly appears on the second X-ray image 1102. The epipolar line L2 is determined by the point Pk and a geometrical positional relation between the first and second X-ray images 1101 and 1102. There is only a point Qk as a candidate corresponding point of the point Pk in FIG. 1, so that the point Qk is determined as the corresponding point of the point Pk.

Figure 2:
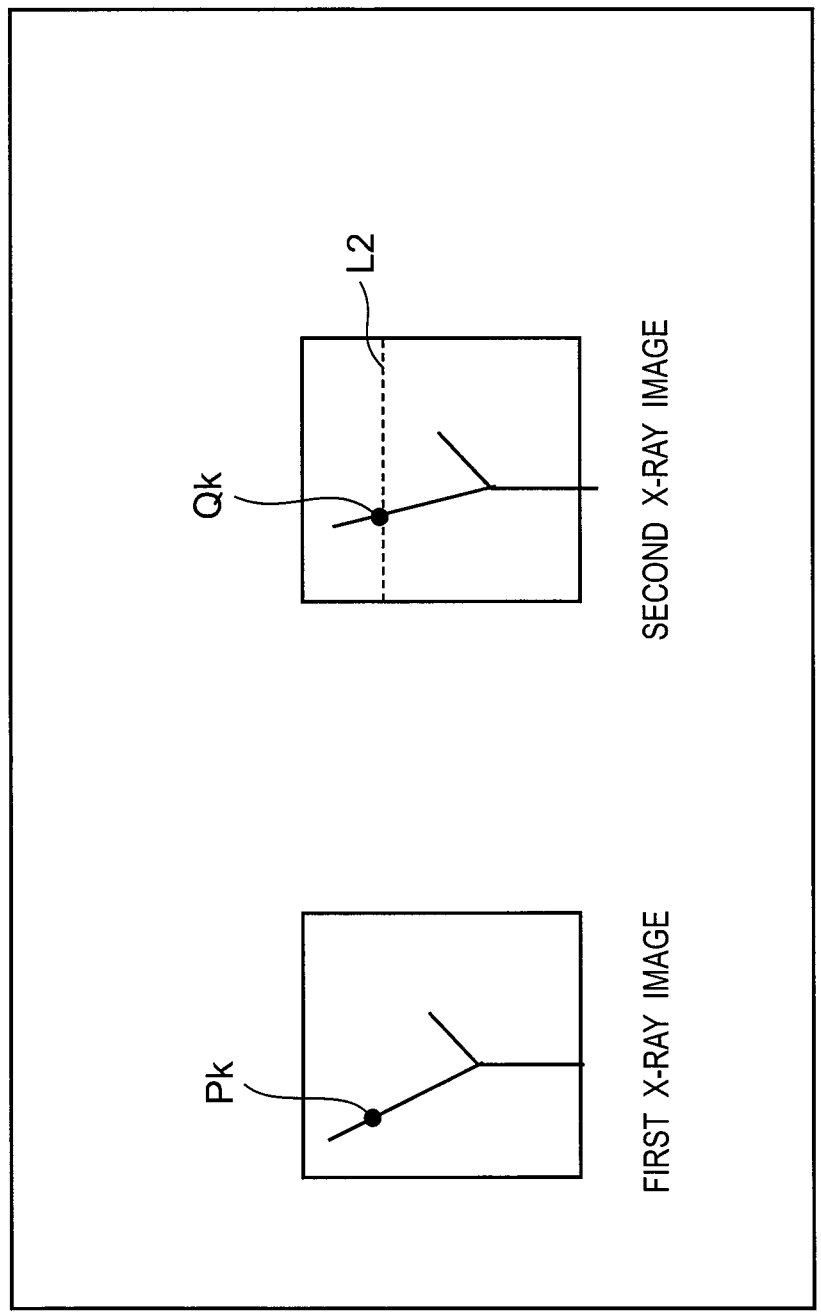
FIG. 2 is a view showing a case where there is one candidate corresponding point.

FIG. 2 is a view showing a case where there is one candidate corresponding point.

As shown in FIG. 2, in a case where the second X-ray image 1102 includes one intersection point between an end point of the blood vessel 1201 and the epipolar line L2, the point Qk is determined as the corresponding point of the point Pk.

Figure 3:
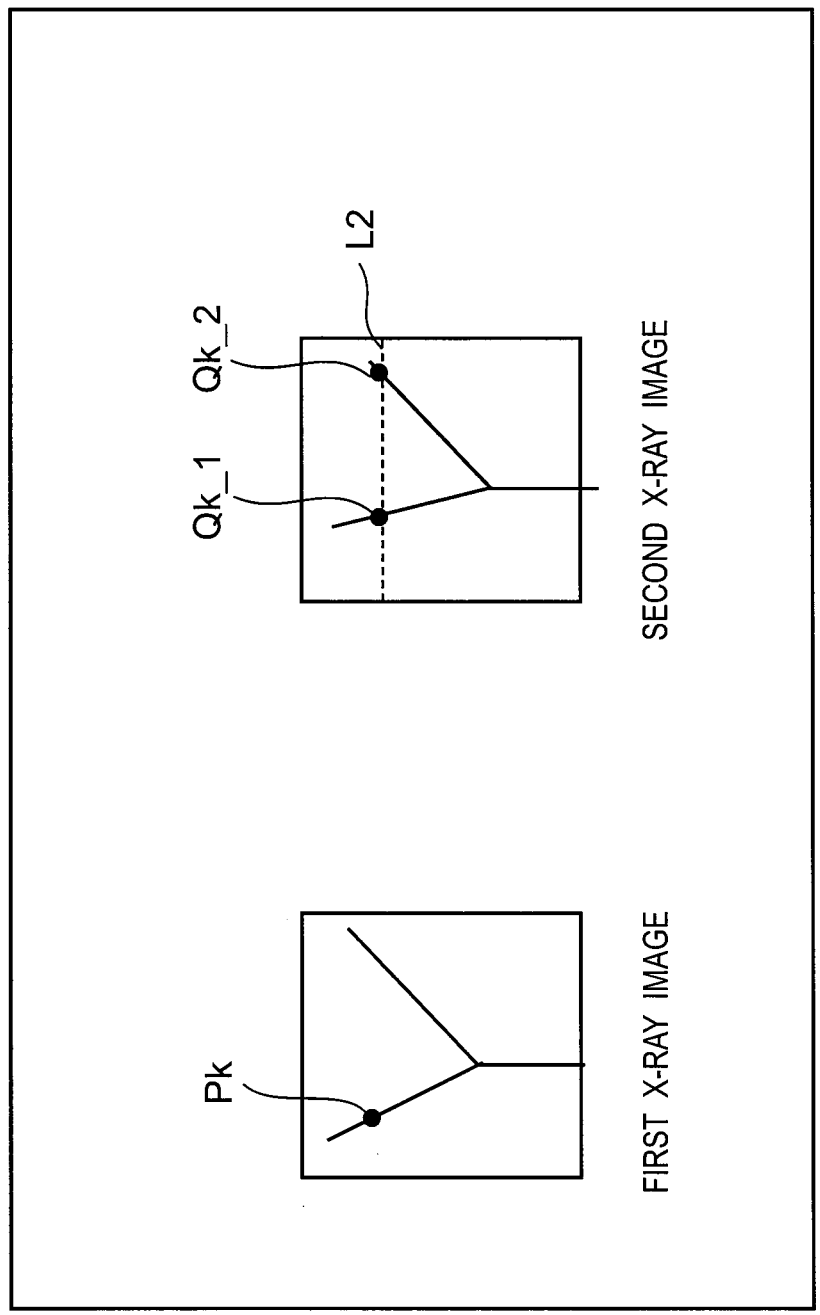
FIG. 3 is a view showing a case where there are two candidate corresponding points.

As shown in FIG. 3, in a different case where the second X-ray image 1102 includes two intersection points between the end point of the blood vessel 1201 and the epipolar line L2, the corresponding point of the point Pk cannot be determined between points Qk_1 and Qk_2.

First, the basic concept of the present disclosure is explained.

Examples of the disclosed technique are as follows.

1st aspect: An image region mapping device configured to map a plurality of image regions of a blood vessel, the device comprising:

an X-ray image acquiring unit configured to, by irradiating the blood vessel through which a contrast medium is passing with X-rays at first and second photographing angles different from each other, acquire an X-ray image set including a first X-ray image at the first photographing angle and a second X-ray image at the second photographing angle;

a first X-ray absorption property acquiring unit configured to acquire, as an absorption property, an absorbed X-ray amount in a first image region corresponding to a portion of the blood vessel in the first X-ray image, from brightness of the contrast medium;

a second X-ray absorption property acquiring unit configured to acquire, as an absorption property, an absorbed X-ray amount in each of a plurality of second image regions corresponding to a portion of the blood vessel in the second X-ray image as candidate corresponding image regions of the first image region, from brightness of the contrast medium;

a similarity degree calculator configured to calculate a similarity degree between the absorbed X-ray amount acquired by the first X-ray absorption property acquiring unit and each of the plurality of absorbed X-ray amounts acquired by the second X-ray absorption property acquiring unit; and a corresponding region determiner configured to determine one of the second image regions corresponding to the first image region in accordance with the similarity degrees calculated by the similarity degree calculator.

According to the 1st aspect, the plurality of image regions in X-ray images of a blood vessel captured in two directions can be adequately mapped.

2nd aspect: The image region mapping device according to the 1st aspect, further comprising:

a radiographing unit information acquiring unit configured to acquire relative positional information between positional information on a first radiographing unit configured to capture the blood vessel at the first photographing angle and positional information on a second radiographing unit configured to capture the blood vessel at the second photographing angle;

a capture target region acquiring unit configured to acquire positional information on the first image region on the first X-ray image; and a second image projection region acquiring unit configured to calculate an epipolar plane defined by the first radiographing unit, the second radiographing unit, and the first image region from the positional information acquired by each of the radiographing unit information acquiring unit and the capture target region acquiring unit, calculate an epipolar line as an intersection line between the calculated epipolar plane and the second X-ray image on the second X-ray image, and acquire positional information on a position on the calculated epipolar line for each of the plurality of second image regions, wherein the second X-ray absorption property acquiring unit acquires an absorption property at the position of the positional information on each of the plurality of second image regions acquired by the second image projection region acquiring unit.

The 2nd aspect achieves determination of mapping of the plurality of image regions according to the absorption properties, out of candidate corresponding regions acquired in accordance with the relative positional relation between the radiographing units.

3rd aspect: The image region mapping device according to the 1st or 2nd aspect, wherein the first X-ray absorption property acquiring unit acquires, as the absorption property, the absorbed X-ray amount in the first image region from a difference between a product of logarithms of a number of pixels in the first image region and intensity of an X-ray emitted from the first radiographing unit and logarithm sums of intensity of X-rays emitted from the first radiographing unit and acquired at the respective pixels in the first image region, and the second X-ray absorption property acquiring unit acquires, as the absorption property, the absorbed X-ray amount in each of the plurality of second image regions from a difference between a product of logarithms of a number of pixels in the corresponding second image region and intensity of an X-ray emitted from the second radiographing unit and a logarithm sum of intensity of X-rays emitted from the second radiographing unit and acquired at the respective pixels in the corresponding second image region.

The 3rd aspect achieves calculation of the absorption properties of the image regions from X-ray intensity of the image regions captured by the radiographing unit and determination of mapping of the plurality of image regions according to the calculated absorption properties.

4th aspect: The image region mapping device according to any one of the 1st to 3rd aspects, wherein the first X-ray absorption property acquiring unit acquires, as the absorption property, a change in absorbed X-ray amount in the first image region from brightness of the contrast medium for a predetermined time period, the second X-ray absorption property acquiring unit acquires, as the absorption property, a change in absorbed X-ray amount in each of the plurality of second image regions from brightness of the contrast medium for the predetermined time period, and the similarity degree calculator calculates a similarity degree between the change in absorbed X-ray amount acquired by the first X-ray absorption property acquiring unit and each of the plurality of changes in absorbed X-ray amount acquired by the second X-ray absorption property acquiring unit.

The 4th aspect achieves highly accurate determination of mapping of the plurality of image regions according to the absorption properties of chronological images captured by the radiographing unit.

5th aspect: The image region mapping device according to the 1st or 2nd aspect, wherein the X-ray image acquiring unit acquires an X-ray image set including the first X-ray image and the second X-ray image at each of first and second predetermined times different from each other, the first X-ray absorption property acquiring unit acquires, as the absorption property, the absorbed X-ray amount in the first image region from a difference between a logarithm sum of intensity of X-rays emitted from the first radiographing unit and acquired at the respective pixels in the first image region at the first predetermined time and logarithm sums of intensity of X-rays emitted from the first radiographing unit and acquired at the respective pixels in the first image region at the second predetermined time, and the second X-ray absorption property acquiring unit acquires, as the absorption property, the absorbed X-ray amount in each of the plurality of second image regions from a difference between logarithm sums of intensity of X-rays emitted from the second radiographing unit and acquired at the respective pixels in the corresponding second image region at the first predetermined time, and logarithm sums of intensity of X-rays emitted from the second radiographing unit and acquired at the respective pixels in the corresponding second image region at the second predetermined time.

The 5th aspect achieves appropriate mapping of the plurality of image regions of the blood vessel according to the absorption properties, also in an X-ray image including the blood vessel along with an object other than the blood vessel, such as a bone or an organ.

6th aspect: The image region mapping device according to the 1st or 2nd aspect, wherein the first X-ray absorption property acquiring unit acquires, as the absorption property, the absorbed X-ray amount in the first image region from a value obtained by dividing a product of intensities of X-rays emitted from the first radiographing unit and acquired at the respective pixels in the first image region by a value obtained by multiplying intensity of an X-ray emitted from the first radiographing unit and a number of pixels in the first image region, and the second X-ray absorption property acquiring unit acquires, as the absorption property, the absorbed X-ray amount in each of the plurality of second image regions from a value obtained by dividing a product of intensities of X-rays emitted from the second radiographing unit and acquired at the respective pixels in the corresponding second image region by a value obtained by multiplying intensity of an X-ray emitted from the second radiographing unit and a number of pixels in the corresponding second image region.

The 6th aspect achieves calculation of the absorbed amount through simple operation and mapping of the image regions.

7th aspect: The image region mapping device according to the 1st or 2nd aspect, wherein the X-ray image acquiring unit acquires an X-ray image set including the first X-ray image and the second X-ray image at each of first and second predetermined times different from each other, the first X-ray absorption property acquiring unit acquires, as the absorption property, the absorbed X-ray amount in the first image region from a value obtained by dividing a product of intensities of X-rays emitted from the first radiographing unit and acquired at the respective pixels in the first image region at the first predetermined time by a product of intensities of X-rays emitted from the first radiographing unit and acquired at the respective pixels in the first image region at the second predetermined time, and the second X-ray absorption property acquiring unit acquires, as the absorption property, the absorbed X-ray amount in each of the plurality of second image regions from a value obtained by dividing a product of intensities of X-rays emitted from the second radiographing unit and acquired at the respective pixels in the corresponding second image region at the first predetermined time by a product of intensities of X-rays emitted from the second radiographing unit and acquired at the respective pixels in the corresponding second image region at the second predetermined time.

The 7th aspect achieves appropriate mapping of the plurality of image regions of the blood vessel according to the absorption properties, also in an X-ray image including the blood vessel along with an object other than the blood vessel, such as a bone or an organ.

8th aspect: A 3D model generating apparatus configured to generate a 3D model of the blood vessel having a bifurcation, the apparatus comprising:

the image region mapping device according to any one of claims 1 to 7, in which the second X-ray absorption property acquiring unit acquires, as an absorption property, from brightness of the contrast medium, an absorbed X-ray amount in each of a plurality of second image regions corresponding to the bifurcation of the blood vessel in the second X-ray image as candidate corresponding image regions of the first image region; and a 3D model generator configured to generate the 3D model of the blood vessel in accordance with information determined by the image region mapping device.

The 8th aspect achieves generation of the 3D model by mapping of the plurality of image regions of the blood vessel. Particularly for generation of a 3D model according to the triangulation principle, an appropriate corresponding point can be determined even when there is a plurality of candidate corresponding points.

9th aspect: An image region mapping method of mapping a plurality of image regions of a blood vessel, the method comprising:

by irradiating the blood vessel through which a contrast medium is passing with X-rays of equal intensity at first and second photographing angles different from each other, with an X-ray image acquiring unit, acquiring an X-ray image set including a first X-ray image at the first photographing angle and a second X-ray image at the second photographing angle;

with a first X-ray absorption property acquiring unit, acquiring, as an absorption property, an absorbed X-ray amount in a first image region corresponding to a portion of the blood vessel in the first X-ray image, from brightness of the contrast medium;

with a second X-ray absorption property acquiring unit, acquiring, as an absorption property, an absorbed X-ray amount in each of a plurality of second image regions corresponding to a portion of the blood vessel in the second X-ray image as candidate corresponding image regions of the first image region, from brightness of the contrast medium;

with a similarity degree calculator, calculating a similarity degree between the absorbed X-ray amount acquired by the first X-ray absorption property acquiring unit and each of the plurality of absorbed X-ray amounts acquired by the second X-ray absorption property acquiring unit; and with a corresponding region determiner, determining the second image region having a maximum similarity degree out of the similarity degrees calculated by the similarity degree calculator as a corresponding region of the first image region.

According to the 9th aspect, the plurality of image regions in X-ray images of a blood vessel captured in two directions can be adequately mapped.

10th aspect: A non-transitory computer-readable recording medium including an image region mapping program configured to map a plurality of image regions of a blood vessel, the program causing a computer to function as:

an X-ray image acquiring unit configured to, by irradiating the blood vessel through which a contrast medium is passing with X-rays at first and second photographing angles different from each other, acquire an X-ray image set including a first X-ray image at the first photographing angle and a second X-ray image at the second photographing angle;

a first X-ray absorption property acquiring unit configured to acquire, as an absorption property, an absorbed X-ray amount in a first image region corresponding to a portion of the blood vessel in the first X-ray image, from brightness of the contrast medium;

a second X-ray absorption property acquiring unit configured to acquire, as an absorption property, an absorbed X-ray amount in each of a plurality of second image regions corresponding to a portion of the blood vessel in the second X-ray image as candidate corresponding image regions of the first image region, from brightness of the contrast medium;

a similarity degree calculator configured to calculate a similarity degree between the absorbed X-ray amount acquired by the first X-ray absorption property acquiring unit and each of the plurality of absorbed X-ray amounts acquired by the second X-ray absorption property acquiring unit; and a corresponding region determiner configured to determine one of the second image regions corresponding to the first image region in accordance with the similarity degrees calculated by the similarity degree calculator.

According to the 10th aspect, the plurality of image regions in X-ray images of a blood vessel captured in two directions can be adequately mapped.

(Basic Principle of the Present Disclosure)

Figure 4:
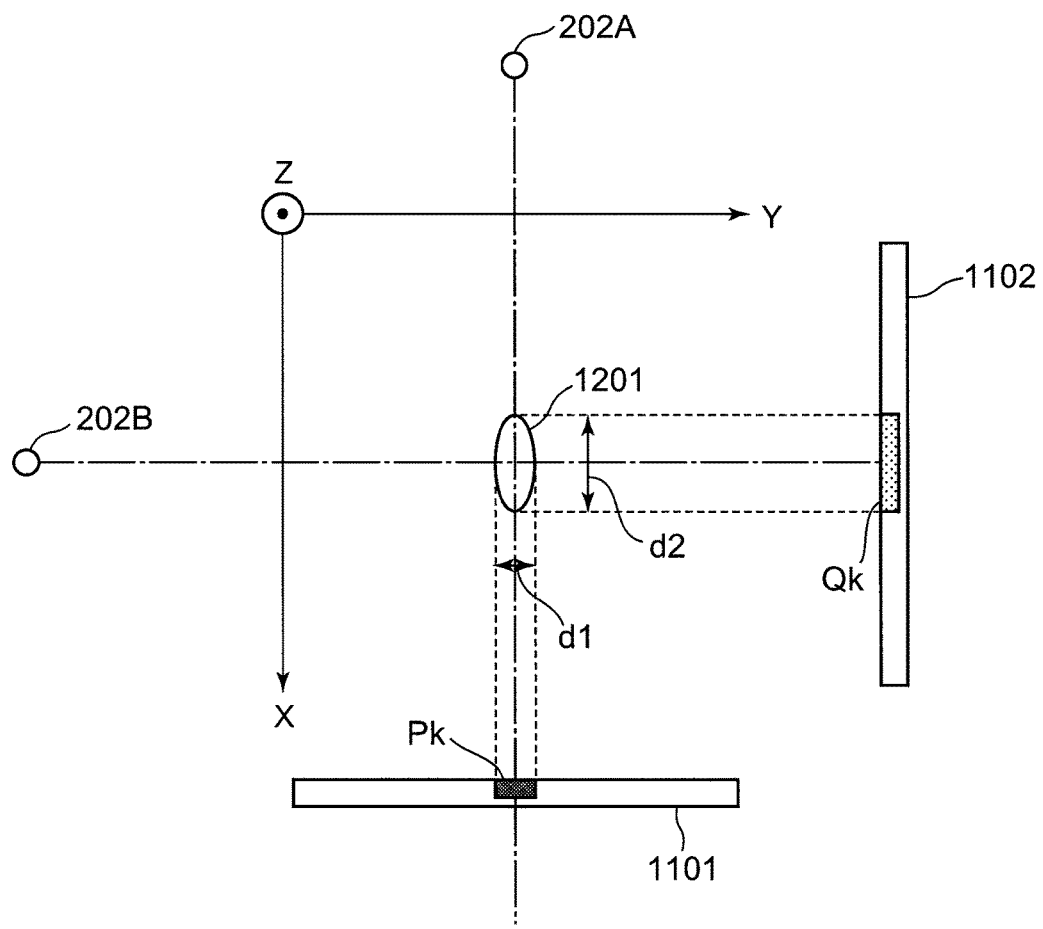
FIG. 4 is an explanatory view of the basic principle of the present disclosure.

FIG. 4 is an explanatory view of the basic principle of the present disclosure.

As depicted in FIG. 4, a blood vessel 1201 has a section in an elliptical shape in this specification. A portion of the blood vessel 1201 referred to for mapping of image regions in the following description may have a bifurcation or may have no bifurcation.

A first radiographing unit (hereinafter, also referred to as an X-ray generator 202A) irradiates the blood vessel 1201 with an X-ray at a first photographing angle to obtain a first X-ray image (first projection image) 1101. A first image region Pk is on the first X-ray image 1101 and corresponds to the blood vessel 1201 that is captured at an angle from the X-ray generator 202A toward the blood vessel 1201. The first image region Pk has brightness lower than that of the remaining region on the first X-ray image 1101 because a contrast medium in the blood vessel 1201 absorbs the X ray.

A second radiographing unit (hereinafter, also referred to as an X-ray generator 202B) irradiates the blood vessel 1201 with an X-ray at a second photographing angle to obtain a second X-ray image (second projection image) 1102. A second image region Qk is on the second X-ray image 1102 and corresponds to the blood vessel 1201 that is captured at an angle from the X-ray generator 202B toward the blood vessel 1201. The second image region Qk has brightness lower than that of the remaining region on the second X-ray image 1102 because the contrast medium in the blood vessel 1201 absorbs the X ray. The first photographing angle and the second photographing angle form a right angle as exemplified in the figure, but are not limited to this case. The first photographing angle and the second photographing angle have only to be different from each other.

When X-rays emitted from the X-ray generators 202A and 202B are equal in intensity, the first image region Pk is lower in brightness than a second image region Qk_2. An X-ray emitted from the X-ray generator 202A passes a width d2 of the blood vessel 1201 whereas an X-ray emitted from the X-ray generator 202B passes a width d1 (d1<d2) of the blood vessel 1201. The X-ray emitted from the X-ray generator 202A and absorbed by the contrast medium in the blood vessel 1201 is thus smaller in amount.

The sum of brightness in the first image region Pk is, however, equal to the sum of brightness in the second image region Qk. In other words, the X-ray emitted from the X-ray generator 202A to the blood vessel 1201 and absorbed by the contrast medium in the blood vessel 1201 is equal in amount to the X-ray emitted from the X-ray generator 202B to the blood vessel 1201 and absorbed by the contrast medium in the blood vessel 1201. Because the amount of an absorbed X-ray is dependent on the amount of a contrast medium, the X-ray absorbed at a certain portion of the blood vessel 1201 is constant in amount regardless of the X-ray incident direction.

The above feature will be described below by a formula.

An X-ray of intensity $I_0$ is attenuated to have intensity $I$ by passing an X-ray absorber of a thickness d. When a linear attenuation coefficient indicative of an attenuation degree is denoted by $\mu$, Equation 1 is obtained.

$$I = I_0 \times e^{-\mu \cdot d} \quad \text{(Equation 1)}$$

Logarithms of the both members of Equation 1 are calculated to obtain Equation 2.

$$\log I = \log I_0 - \mu d \quad \text{(Equation 2)}$$

The amount of the X-ray generated from the X-ray generator 202A and absorbed by the contrast medium in the blood vessel 1201 can be obtained from brightness of each pixel composing the first image region Pk, or intensity of the X-ray in each pixel. More specifically, the amount of the absorbed X-ray can be obtained in the following manner.

The sum of intensity $I_{p\_k\_n}$ (n=1, 2, ..., and N) in respective pixels composing the first image region Pk can be calculated in accordance with Equation 3. In this equation, N is an integer of 2 or more and denotes the maximum number of pixels composing the first image region Pk.

$$\sum_{n=1}^{N} \log I_{pk\_n} = N \log I_0 - \mu \sum_{n=1}^{N} d2_{pk\_n} \quad \text{(Equation 3)}$$

The thickness d2 of the blood vessel 1201 viewed from the X-ray generator 202A varies in each pixel composing the first image region Pk. The thickness d2 is thus expressed as thicknesses $d2_{p\_k\_n}$ (n=1, 2, ..., and N) in Equation 3.

By applying Equation 3, the amount of the X-ray generated from the X-ray generator 202A and absorbed by the contrast medium in the blood vessel 1201 is expressed by Equation 4.

$$\mu \sum_{n=1}^{N} d2_{pk\_n} = N \log I_0 - \sum_{n=1}^{N} \log I_{pk\_n} \quad \text{(Equation 4)}$$

Similarly, the amount of the X-ray generated from the X-ray generator 202B and absorbed by the contrast medium in the blood vessel 1201 is expressed by Equation 5.

$$\mu \sum_{m=1}^{M} d1_{qk\_m} = M \log I_0 - \sum_{m=1}^{N} \log I_{qk\_m} \quad \text{(Equation 5)}$$

Assume that intensity of respective pixels composing the second image region Qk is denoted by $I_{q\_k\_n}$ (m=1, 2, ..., and M) and thicknesses of the blood vessel 1201 viewed from the X-ray generator 202B are denoted by $d1_{q\_k\_m}$=1, 2, ... and M). In this equation, M is an integer of 2 or more and denotes the maximum number of pixels composing the second image region Qk.

As described above, the X-ray emitted from the X-ray generator 202A and absorbed by the contrast medium in the blood vessel 1201 is equal in amount to the X-ray emitted from the X-ray generator 202B and absorbed by the contrast medium in the blood vessel 1201. Equation 4 is thus equal to Equation 5.

The present disclosure is based on the principle described above, so as to achieve determination of a correspondence relation between a first region on the first X-ray image 1101 and a second region on the second X-ray image 1102. The present disclosure thus can achieve generation of a 3D model of the blood vessel 1201.

First Embodiment

Configuration of Apparatus

Figure 5:
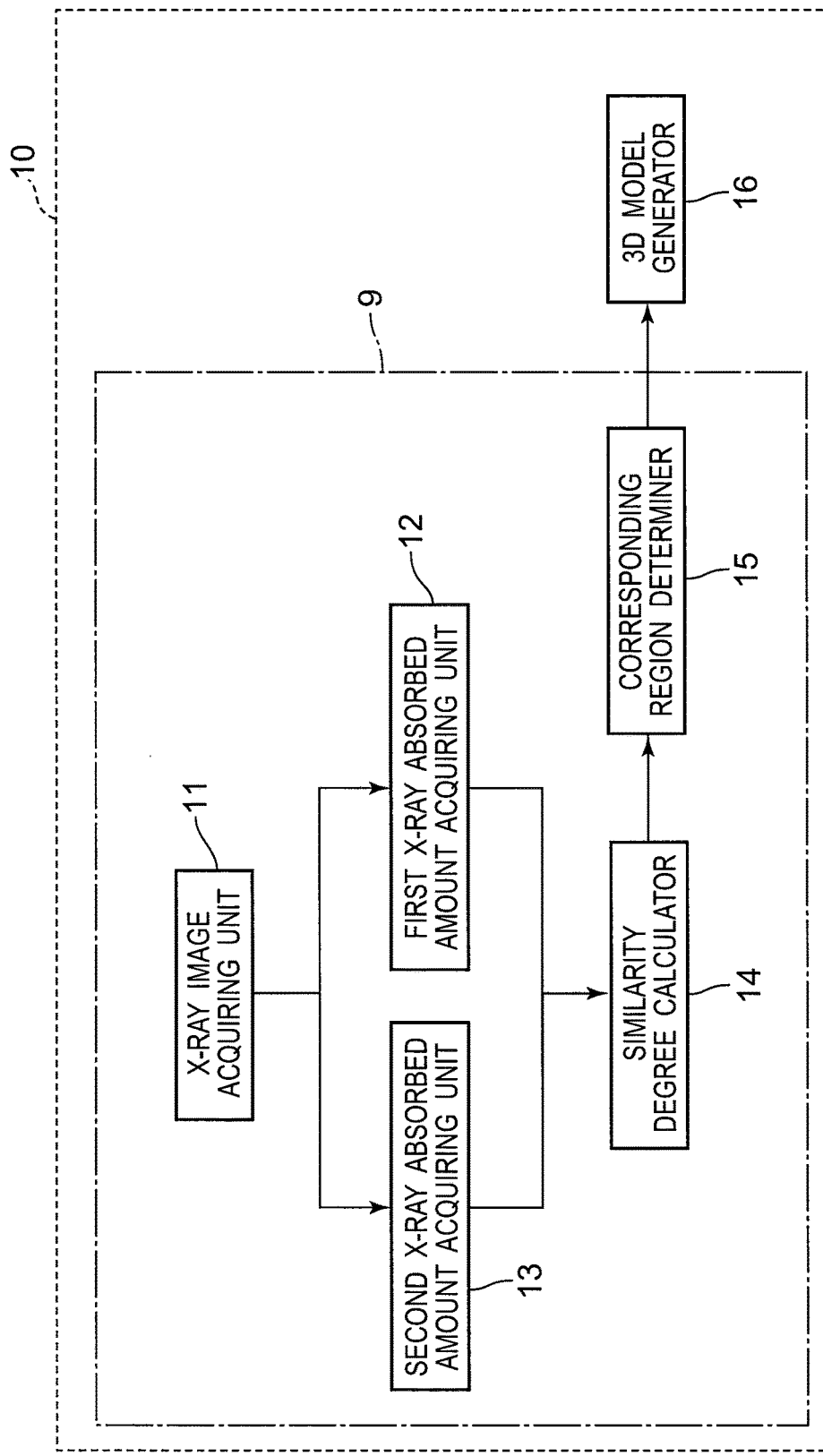
FIG. 5 is a block diagram of the functional configuration of a 3D model generating apparatus according to a first embodiment.

FIG. 5 is a functional block diagram of a 3D model generating apparatus 10 including an image region mapping device 9 according to the first embodiment of the present disclosure.

The 3D model generating apparatus 10 includes the image region mapping device 9 and a 3D model generator 16.

The image region mapping device 9 includes an X-ray image acquiring unit 11, a first X-ray absorbed amount acquiring unit 12 exemplifying and functioning as a first X-ray absorption property acquiring unit, a second X-ray absorbed amount acquiring unit 13 exemplifying and functioning as a second X-ray absorption property acquiring unit, a similarity degree calculator 14, and a corresponding region determiner 15.

<X-Ray Image Acquiring Unit 11>

The X-ray image acquiring unit 11 irradiates the blood vessel 1201 through which a contrast medium is passing with X-rays at the first and second photographing angles to acquire an X-ray image set including the first X-ray image 1101 at the first photographing angle and the second X-ray image 1102 at the second photographing angle, from photographing start timing to photographing end timing commanded by an input IF 114 (e.g. at predetermined time intervals). Acquisition of an image set can be performed only once at the timing commanded by the input IF 114, or can be performed from a start time to an end time commanded by the input IF 114.

<First X-Ray Absorbed Amount Acquiring Unit 12>

The first X-ray absorbed amount acquiring unit 12 acquires an amount of the absorbed X-ray in the first image region Pk at the portion of the blood vessel 1201 in the first X-ray image 1101 acquired by the X-ray image acquiring unit 11.

The first image region Pk includes the blood vessel 1201.

<Second X-Ray Absorbed Amount Acquiring Unit 13>

The second X-ray absorbed amount acquiring unit 13 acquires an amount of the absorbed X-ray in each of second image regions Qk_n (n=1, 2, ..., and N) as candidate image regions (candidate corresponding points) which are acquired by the X-ray image acquiring unit 11 and correspond to the first image region Pk.

The second image regions Qk_n each include the blood vessel 1201.

<Similarity Degree Calculator 14>

The similarity degree calculator 14 calculates a similarity degree between the amount of the absorbed X-ray acquired by the first X-ray absorbed amount acquiring unit 12 and the amount of each of the absorbed X-rays acquired by the second X-ray absorbed amount acquiring unit 13.

<Corresponding Region Determiner 15>

The corresponding region determiner 15 determines, as a region corresponding to the first image region Pk, the second image region Qk_n having the highest similarity degree out of a plurality of similarity degrees calculated by the similarity degree calculator 14. Alternatively, the corresponding region determiner 15 determines, as a region corresponding to the first image region Pk, the second image region Qk_n having a similarity degree higher than a predetermined threshold. If there are second image regions Qk_n each having a similarity degree higher than the predetermined threshold, the corresponding region determiner 15 determines that the second image region Qk_n initially decided as having a similarity degree higher than the predetermined threshold corresponds to the first image region Pk, for example. This determination enables mapping between the second image region Qk_n and the first image region Pk.

<3D Model Generator 16>

The 3D model generator 16 generates a 3D model of the blood vessel 1201 in accordance with information determined by the corresponding region determiner 15.

<Operation of Apparatus>

Figure 6:
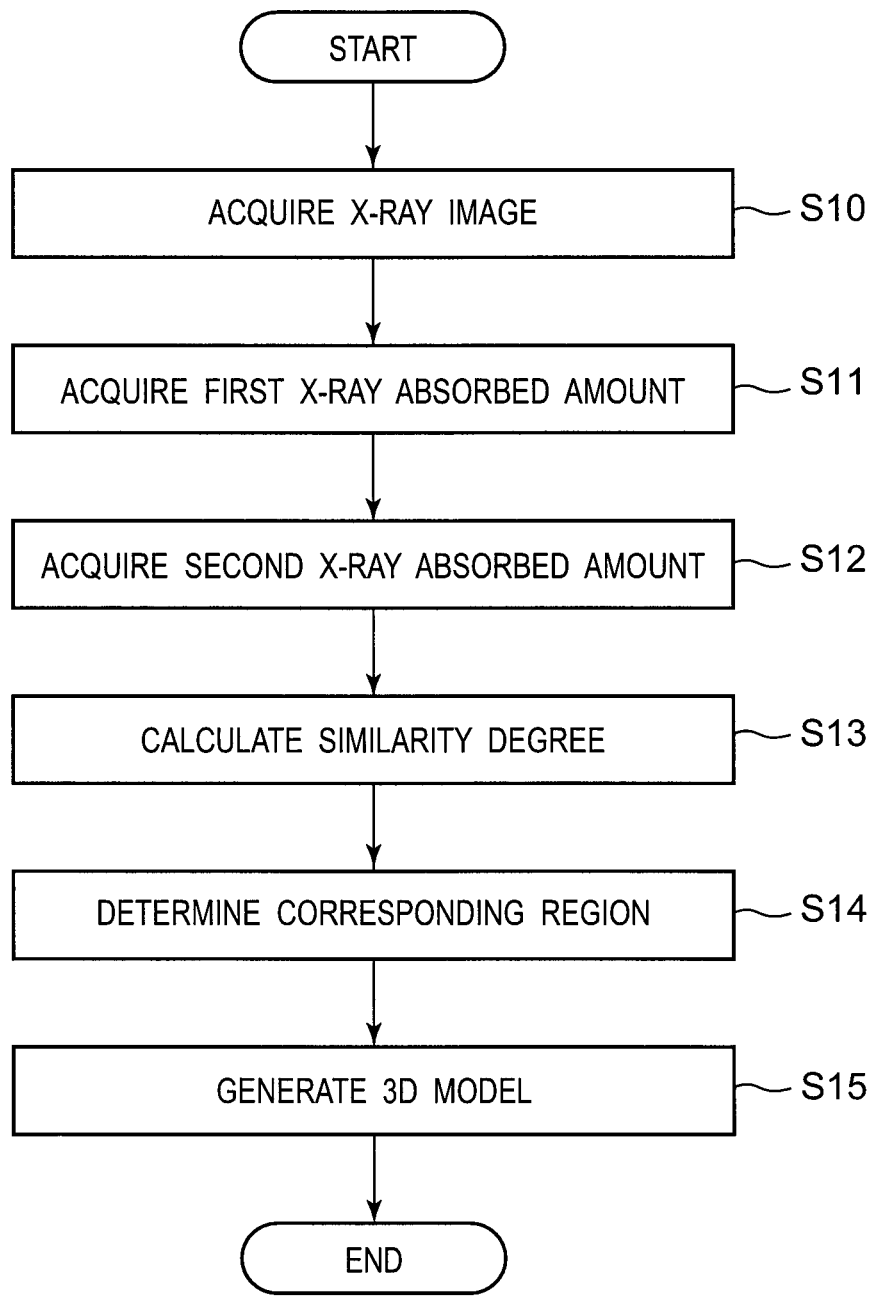
FIG. 6 is an exemplary flowchart of the processes of the 3D model generating apparatus according to the first embodiment.

FIG. 6 depicts a flow of the processes of the image region mapping device 9 and the 3D model generating apparatus 10 according to the first embodiment.

Initially, the X-ray image acquiring unit 11 irradiates the blood vessel 1201 through which a contrast medium is passing with X-rays of equal intensity at the first and second photographing angles to acquire an X-ray image set including the first X-ray image 1101 at the first photographing angle and the second X-ray image 1102 at the second photographing angle (step S10).

The first X-ray absorbed amount acquiring unit 12 subsequently calculates X-ray intensity after vascular permeability from brightness of the contrast medium to acquire an amount of the absorbed X-ray in the first image region Pk corresponding to the portion of the blood vessel 1201 in the first X-ray image 1101 acquired by the X-ray image acquiring unit 11 (step S11).

The second X-ray absorbed amount acquiring unit 13 then calculates X-ray intensity after vascular permeability from brightness of the contrast medium in each of the plurality of second image regions Qk_n (n=1, 2, . . . , and N) which correspond to the portion of the blood vessel 1201 in the second X-ray image 1102 acquired by the X-ray image acquiring unit 11 as candidate corresponding image regions of the first image region Pk, to acquire an amount of the absorbed X-ray in each of the second image regions Qk_n (step S12). Step S11 and step S12 can be executed simultaneously.

The similarity degree calculator 14 subsequently calculates a similarity degree between the amount of the absorbed X-ray acquired by the first X-ray absorbed amount acquiring unit 12 and the amount of each of the absorbed X-rays acquired by the second X-ray absorbed amount acquiring unit 13 (step S13).

The corresponding region determiner 15 thereafter determines, as a region corresponding to the first image region Pk, the second image region Qk_n having the highest similarity degree out of the plurality of similarity degrees calculated by the similarity degree calculator 14 (step S14). These processes are the processes of the image region mapping device 9.

The 3D model generator 16 subsequently generates a 3D model of the blood vessel 1201 in accordance with the information determined by the corresponding region determiner 15 (step S15).

Effects of First Embodiment

In the image region mapping device 9 according to the first embodiment, even when there is a plurality of second X-ray images 1102 for the first region on the first X-ray image 1101, the corresponding region determiner 15 can determine a correspondence relation between the first region on the first X-ray image 1101 and the second region on the most appropriate one of the second X-ray images 1102. The 3D model generating apparatus 10 can thus generate a 3D model of the blood vessel 1201 from the result of image region mapping by the image region mapping device 9.

Mapping is applied herein to the blood vessel 1201 into which a contrast medium is injected. Mapping can be applied similarly to an ordinary object other than a blood vessel.

Second Embodiment

Figure 7:
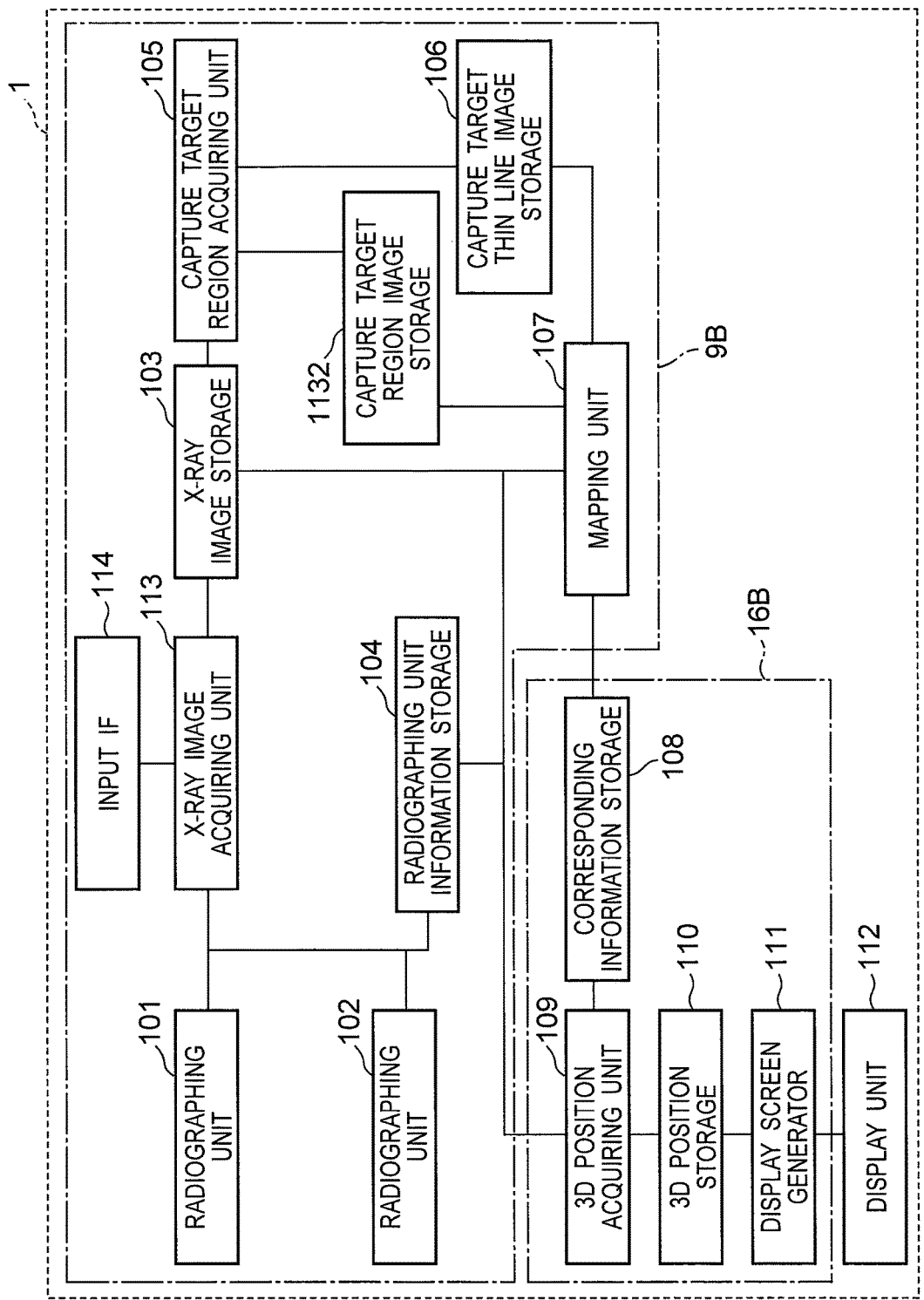
FIG. 7 is a block diagram of the functional configuration of a shape restoring apparatus according to a second embodiment.

FIG. 7 is a view of the configuration of a 3D model generating apparatus 1 (hereinafter, also referred to as a shape restoring apparatus 1) including an image region mapping device 9B according to the second embodiment of the present disclosure. The shape restoring apparatus 1 includes the image region mapping device 9B, a 3D model generator 16B, and a display unit 112, for example.

The image region mapping device 9B includes an X-ray image acquiring unit 113, radiographing units 101 and 102 corresponding to the X-ray generators 202A and 202B, a radiographing unit information storage 104, the input interface (IF) 114, an X-ray image storage 103, a capture target region acquiring unit 105, a capture target thin line image storage 106, a capture target region image storage 1132, and a mapping unit 107, for example. The X-ray image acquiring unit 113 corresponds to the X-ray image acquiring unit 11 according to the first embodiment. The mapping unit 107 corresponds to the first X-ray absorbed amount acquiring unit 12 (exemplifying the first X-ray absorption property acquiring unit) and the second X-ray absorbed amount acquiring unit 13 (exemplifying the second X-ray absorption property acquiring unit) according to the first embodiment, as well as to the similarity degree calculator 14 and the corresponding region determiner 15 according to the first embodiment, for example.

The 3D model generator 16B includes a corresponding information storage 108, a 3D position acquiring unit 109, a 3D position storage 110, and a display screen generator 111.

The radiographing units 101 and 102 are devices each configured to acquire a captured radioscopy image by irradiating a capture target site of a test subject with a radiation at a different angle or acquire a captured blood vessel contrast image by injecting a contrast medium, and are called X-ray blood vessel imaging devices, angiography devices, or the like. The radiographing units 101 and 102 according to the second embodiment each capture a blood vessel as a capture target. The radiographing units 101 and 102 are configured identically, so that the configuration of the radiographing unit 101 will be described representatively.

Figure 8:
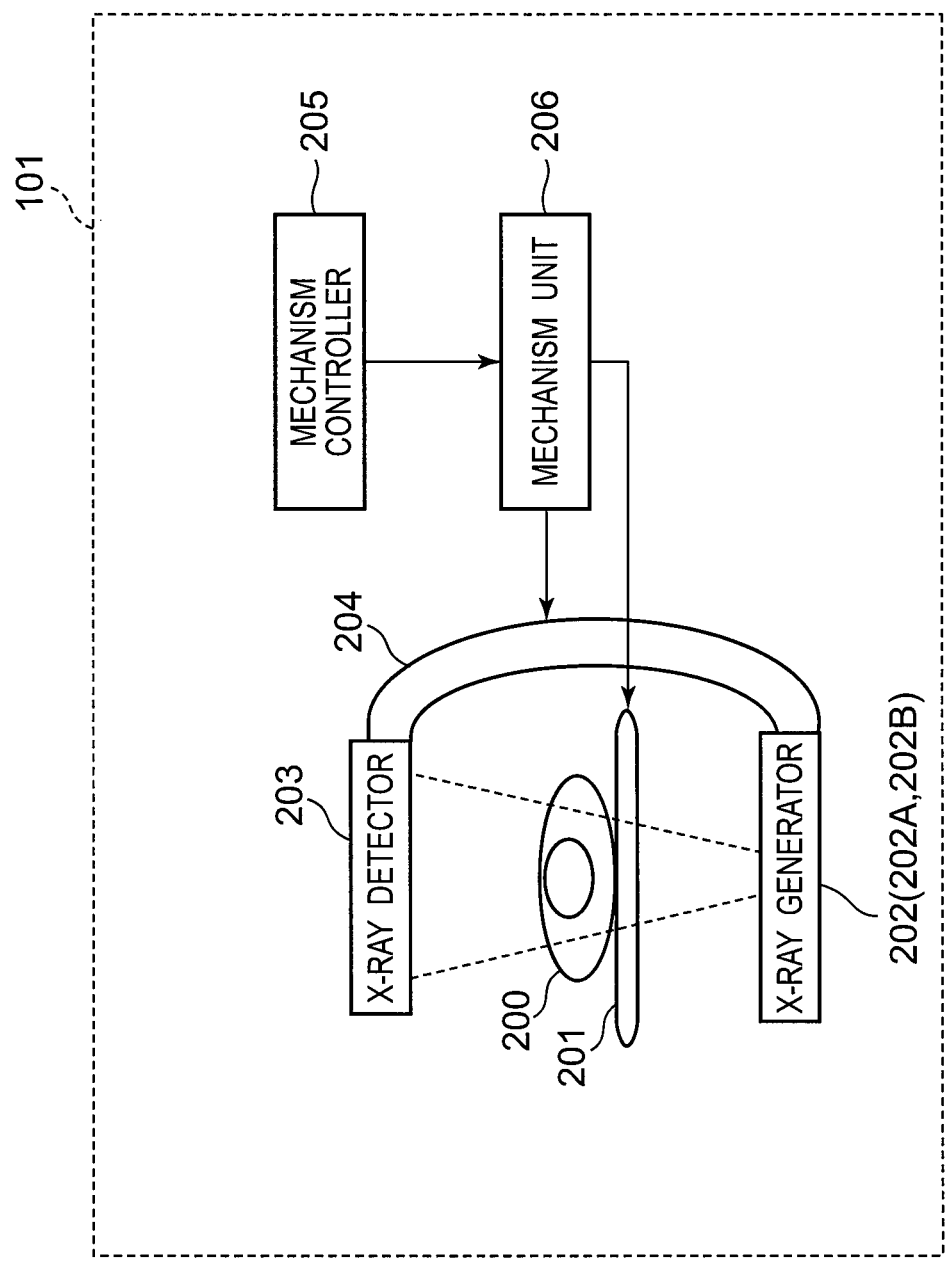
FIG. 8 is a block diagram of the configuration of a radiographing system.

FIG. 8 depicts the configuration of the radiographing unit 101. The radiographing unit 101 includes an X-ray generator 202, an X-ray detector 203, a mechanism unit 206, and a mechanism controller 205.

The X-ray generator 202 has an X-ray tube configured to generate an X-ray with high voltage, and an X-ray limiting device configured to partially block an X-ray to control an irradiation field, and irradiates a patient 200 on a bed 201 with an X-ray.

The X-ray detector 203 is a camera configured to record image information acquired by receiving an X-ray having transmitted the patient 200 and output the recorded image information. The X-ray detector 203 can be a flat panel detector (FPD) having an X-ray sensitive layer and configured to convert an X-ray to digital data and output the digital data. When the X-ray generator 202 irradiates the patient 200 with an X-ray, the X-ray detector 203 transmits, to the X-ray image acquiring unit 113, image information on a captured X-ray image.

The mechanism unit 206 shifts an arm 204 and the bed 201 in accordance with commands by the mechanism controller 205 that has received an operation command of an operator.

The mechanism controller 205 transmits a position of the X-ray generator 202 or the X-ray detector 203 to the radiographing unit information storage 104.

The radiographing unit 102 also has units similar to those of the radiographing unit 101. When the X-ray generator 202 in the radiographing unit 101 and the X-ray generator 202 in the radiographing unit 102 are distinguished from each other, the former will be called the X-ray generator 202A and the latter will be called the X-ray generator 202B.

The X-ray image acquiring unit 113 acquires an X-ray image (radiological image) from each of the radiographing units 101 and 102 and stores the acquired X-ray images in the X-ray image storage 103. The X-ray image acquiring unit 113 starts and ends image acquisition at timings commanded by the input IF 114 to be described later.

More specifically, the X-ray image acquiring unit 113 starts image acquisition in accordance with a command from the input IF 114, and stores an image acquired from the radiographing unit 101 in the X-ray image storage 103, for example. The X-ray image acquiring unit 113 then repeats acquiring an image from the radiographing unit 101 and stores the acquired image in the X-ray image storage 103 at timing commanded by the input IF 114 (e.g. at predetermined time intervals) until receiving an end command from the input IF 114. The X-ray image acquiring unit 113 similarly acquires an image from the radiographing unit 102 and stores the acquired image in the X-ray image storage 103 at timing commanded by the input IF 114 (e.g. at predetermined time intervals).

The radiographing unit information storage 104 holds information on the radiographing units 101 and 102. The radiographing unit information storage 104 is particularly embodied by a memory device such as a resister, a cash, a RAM, or a ROM of a CPU. Hereinafter, assume that any unit named to include "storage" is embodied similarly.

The radiographing unit information storage 104 specifically holds relative positional information on the radiographing units 101 and 102 and an internal parameter A of the camera in each of the radiographing units 101 and 102. FIG. 9 is an exemplary chart of a data structure in the radiographing unit information storage 104. The radiographing unit information storage 104 holds a translation vector T, a rotation vector R, and internal parameters A1 and A2.

The translation vector T indicates a position of the radiographing unit 102 based on a position of the radiographing unit 101, and exemplifies relative positional information between positional information pieces on the radiographing units 101 and 102 (positional information on the first radiographing unit and positional information on the second radiographing unit). The rotation vector R indicates a capture direction of the radiographing unit 102 relatively to a capture direction of the radiographing unit 101. The internal parameter A1 indicates a positional relation between an imaging lens and an imaging plane of an image sensor included in the camera of the radiographing unit 101. The internal parameter A1 indicates a positional relation between the X-ray generator 202 and the X-ray detector 203 in the radiographing unit 101. For simplified description, assume that the X-ray detector 203 is fixed in position relatively to the X-ray generator 202 and the internal parameters A1 and A2 preliminarily have values and are stored in the radiographing unit information storage 104.

Also assume that the radiographing unit 102 is constantly fixed in relative position to the radiographing unit 101 and the radiographing unit information storage 104 preliminarily holds the translation vector T and the rotation vector R. The radiographing unit information storage 104 can be alternatively configured to acquire positions of the radiographing units 101 and 102 and calculate a translation vector T and a rotation vector R from the acquired positions.

The input IF 114 is a device that allows an operating person (operator) to input a command to the shape restoring apparatus 1. The input IF 114 is embodied by a button, a switch, a computer keyboard, a mouse, or the like. The input IF 114 is used to command the X-ray image acquiring unit 113 to start and end image acquisition.

The X-ray image storage 103 holds images acquired by the X-ray image acquiring unit 113. FIG. 10 is a chart of a data structure in the X-ray image storage 103. Assume that the X-ray image acquiring unit 113 starts image acquisition at a time 0 and ends image acquisition at a time END. The X-ray image storage 103 holds images captured by the radiographing units 101 and 102 at each time from the start to the end of the image acquisition. Assume in the following description that the radiographing unit 101 captures an image 1_$n$ at a time n and the radiographing unit 102 captures an image 2_$n$ at the time n. Images 1_0 and 2_0 captured at the time 0 will be called background images.

The capture target region acquiring unit 105 acquires a region of the blood vessel 1201 into which a contrast medium is injected from images 1_END and 2_END. FIG. 11 is a view of the configuration of the capture target region acquiring unit 105. The capture target region acquiring unit 105 includes a difference image generator 1504, a difference image storage 1505, a binarizing unit 1501, and a line thinning unit 1503.

The difference image generator 1504 acquires images n_END and images n_0 (background images) from the X-ray image storage 103, generates a difference image, and stores the generated difference image in the difference image storage 1505 (n=1 and 2).

The difference image storage 1505 holds the difference image generated by the difference image generator.

The binarizing unit 1501 acquires the difference image from the difference image storage 1505, binarizes the acquired difference image, and stores the binary image in the capture target region image storage 1132. Assume that the blood vessel region has the pixel value "1" and the remaining region has the pixel value "0" in the present embodiment.

Figure 12:
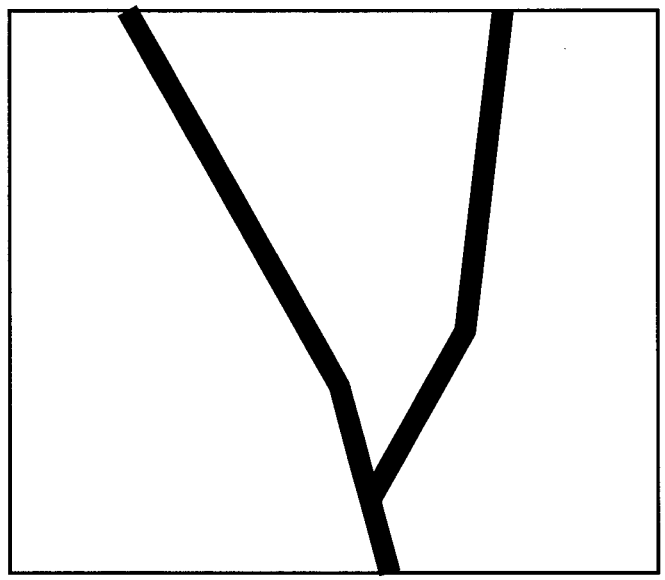
FIG. 12 is an exemplary view of a binary image according to the second embodiment.
Figure 13:
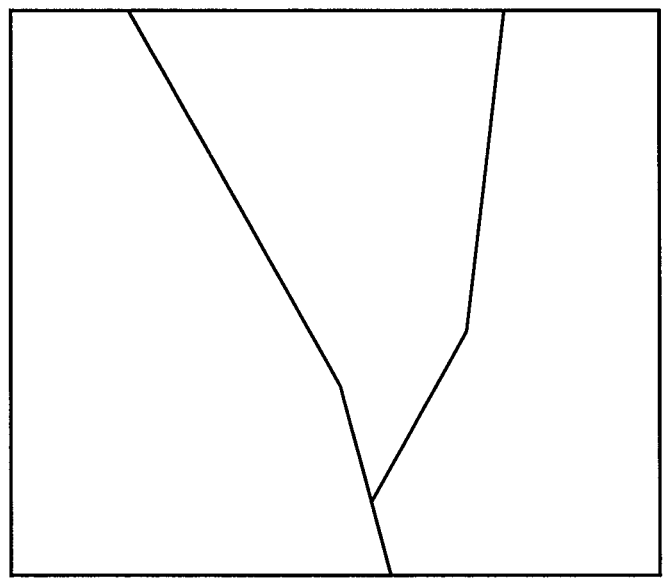
FIG. 13 is an exemplary view of a thin line image according to the second embodiment.

The line thinning unit 1503 thins lines in the binary image held by the capture target region image storage 1132 and stores a thin line image in the capture target thin line image storage 106. FIG. 13 depicts a thin line image obtained by thinning lines in the binary image in FIG. 12.

<Flow of Processes Executed by Capture Target Region Acquiring Unit 105>

Figure 14:
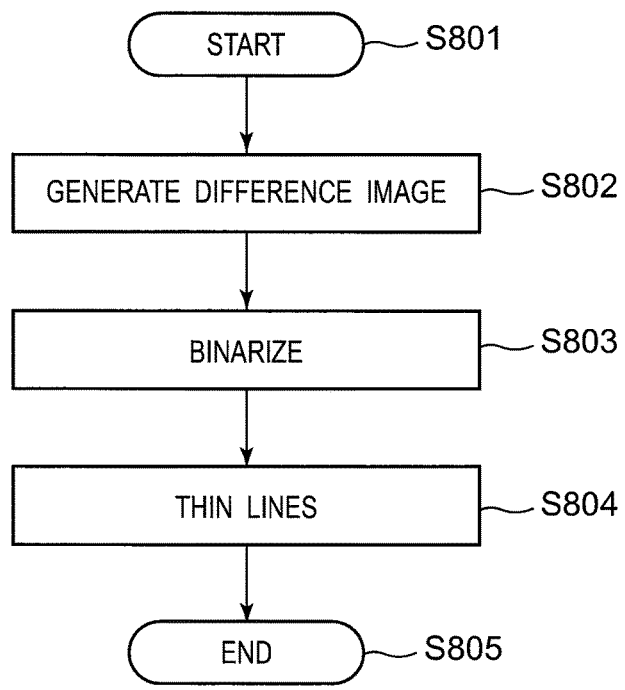
FIG. 14 is a flowchart of the capture target region acquiring unit according to the second embodiment.

FIG. 14 is a flowchart of the processes of the capture target region acquiring unit 105 that acquires a capture target region in the image 1_END.

The capture target region acquiring unit 105 starts the processes in step S801.

Subsequently in step S802, the difference image generator 1504 executes the above-described process of the difference image generator 1504. More specifically, the difference image generator 1504 acquires the images 1_0 and 1_END from the X-ray image storage 103, calculates a difference at each pixel of the acquired image to generate a difference image, and stores the generated difference image in the difference image storage 1505.

Subsequently in step S803, the binarizing unit 1501 executes the above-described process of the binarizing unit 1501. More specifically, the binarizing unit 1501 acquires the difference image from the difference image storage 1505, binarizes the acquired difference image, and stores the binary image in the capture target region image storage 1132.

Subsequently in step S804, the line thinning unit 1503 executes the above-described process of the line thinning unit 1503. More specifically, the line thinning unit 1503 thins lines in the binary image held by the capture target region image storage 1132 and stores the thin line image in the capture target thin line image storage 106.

The capture target region acquiring unit 105 then ends the processes in step S805.

The capture target region acquiring unit 105 similarly processes the image 2_END that is captured by the radiographing unit 102.

Figure 15:
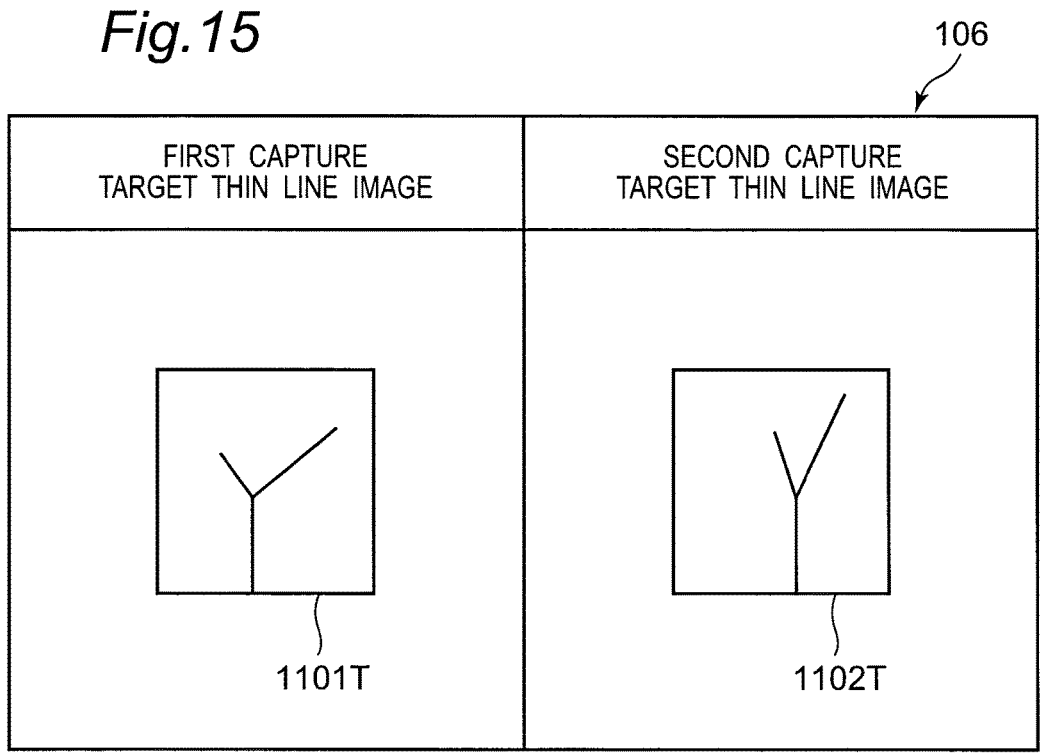
FIG. 15 is a chart of a data structure in a capture target thin line image storage according to the second embodiment.

The capture target thin line image storage 106 holds a capture target region acquired by the capture target region acquiring unit 105. FIG. 15 is a chart of a data structure in the capture target thin line image storage 106. The capture target thin line image storage 106 holds a first capture target thin line image 1101T generated from the image 1_END and a second capture target thin line image 1102T generated from the image 2_END.

The capture target region image storage 1132 holds a capture target region image acquired by the capture target region acquiring unit 105. The capture target region image storage 1132 holds a first capture target region image generated from the image 1_END and a second capture target region image generated from the image 2_END.

The mapping unit 107 acquires a position of a corresponding point on the second capture target thin line image 1102T, of a black point on the first capture target thin line image 1101T held by the capture target thin line image storage 106. In the following description, respective points on the first capture target thin line image 1101T will be called first image projection points Pk (k=1, 2, . . . , and K; where K is the number of first image projection points on the first capture target thin line image 1101T) (see FIG. 18).

Figure 16:
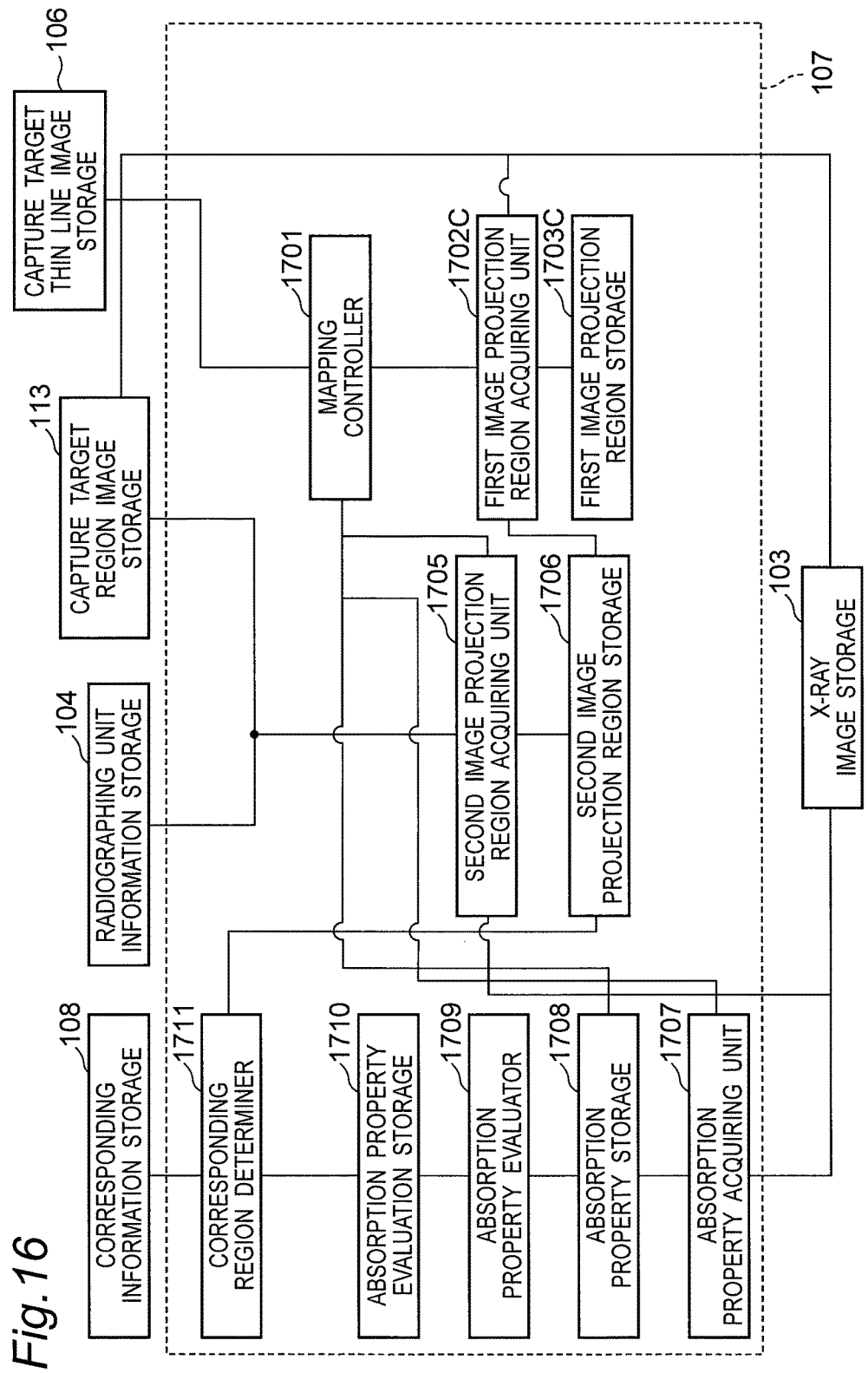
FIG. 16 is a view of the configuration of a mapping unit according to the second embodiment.

FIG. 16 is a view of the configuration of the mapping unit 107. The mapping unit 107 includes a first image projection region acquiring unit 1702C functioning as one example of the capture target region acquiring unit, a first image projection region storage 1703C, a second image projection region acquiring unit 1705, a second image projection region storage 1706, an absorption property acquiring unit 1707 functioning as one example of each of the first X-ray absorption property acquiring unit 12 and the second X-ray absorption property acquiring unit 13, an absorption property storage 1708, an absorption property evaluator 1709 functioning as one example of the similarity degree calculator, an absorption property evaluation storage 1710, a corresponding region determiner 1711, and a mapping controller 1701.

An epipolar line and an epipolar plane acquired through calculation by the second image projection region acquiring unit 1705 will be described with reference to FIG. 18 before description of the second image projection region acquiring unit 1705.

Figure 18:
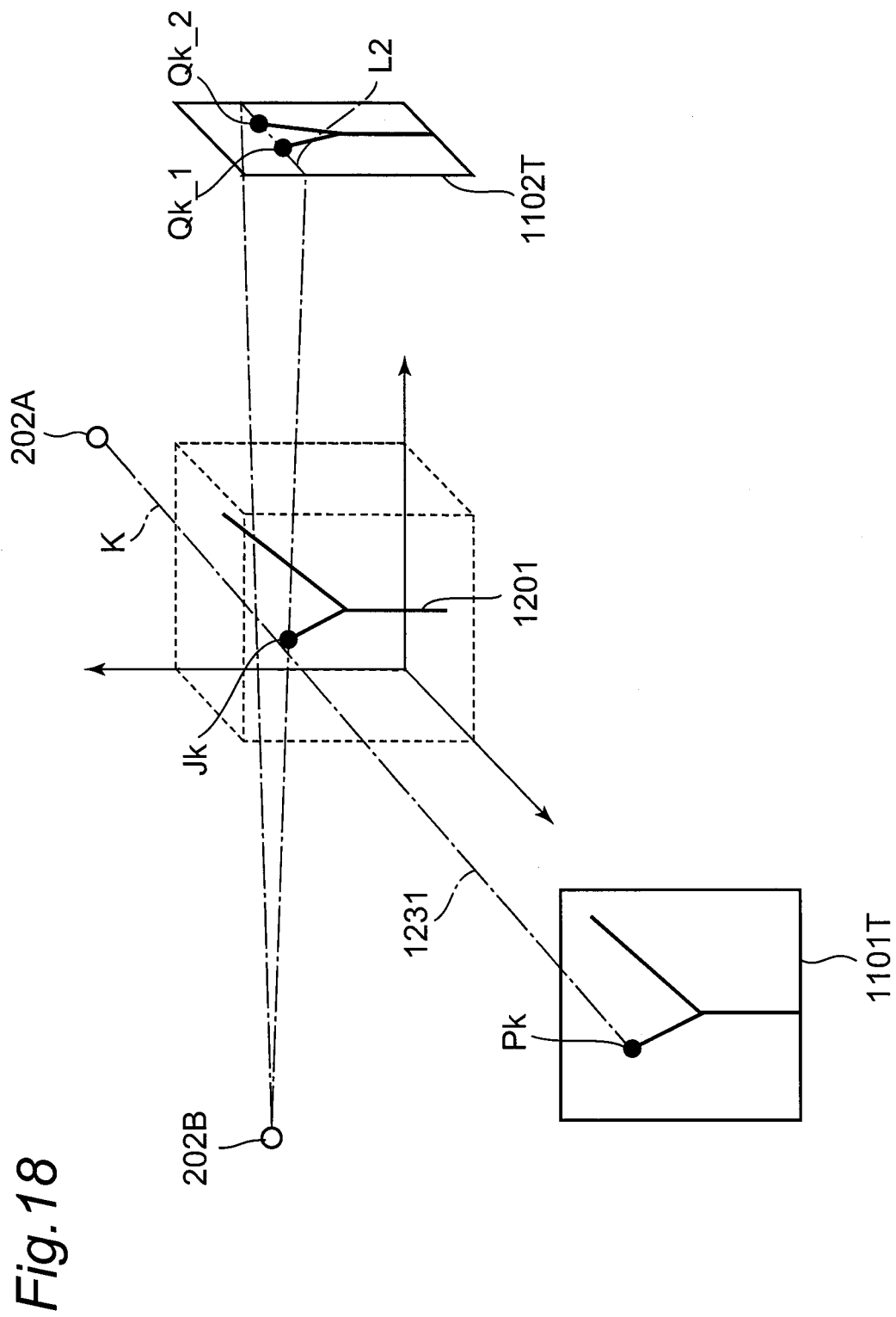
FIG. 18 is a view of an epipolar line L2 according to the second embodiment.

Reference sign 1201 indicates a blood vessel in FIG. 18. An X-ray generated by the X-ray generator 202A in the radiographing unit 101 and having passed a 3D point Jk is projected at the first image projection point Pk on the first image 1101 on the X-ray detector 203A.

The position of the 3D point Jk cannot be specified only from the position of the first image projection point Pk. The 3D point Jk is assumed to be located somewhere on a straight line 1231 that connects the X-ray generator 202A and the first image projection point Pk.

The point on the straight line 1231 is projected on an epipolar line L2 in FIG. 18 on the second image 1102. The 3D point Jk is located on the straight line 1231, so that a projection point of the 3D point Jk also appears somewhere on the epipolar line L2. A candidate corresponding point of the 3D point Jk can be accordingly narrowed down to the projection point on the epipolar line L2.

A plane including the X-ray generator 202B and the X-ray generator 202A in the radiographing unit 102 and the first image projection point Pk will be described next. This plane is called an epipolar plane (for the first image projection point Pk).

All 3D points on this plane including the 3D point Jk are projected on the epipolar line L2 on the second image 1102. It is because all straight lines connecting the X-ray generator 202B and such 3D points are projected on the epipolar line L2.

All 3D points on this plane are projected on an epipolar line L1 on the first image 1101. It is because all straight lines connecting the X-ray generator 202A and such 3D points are projected on the epipolar line L1.

Figure 19:
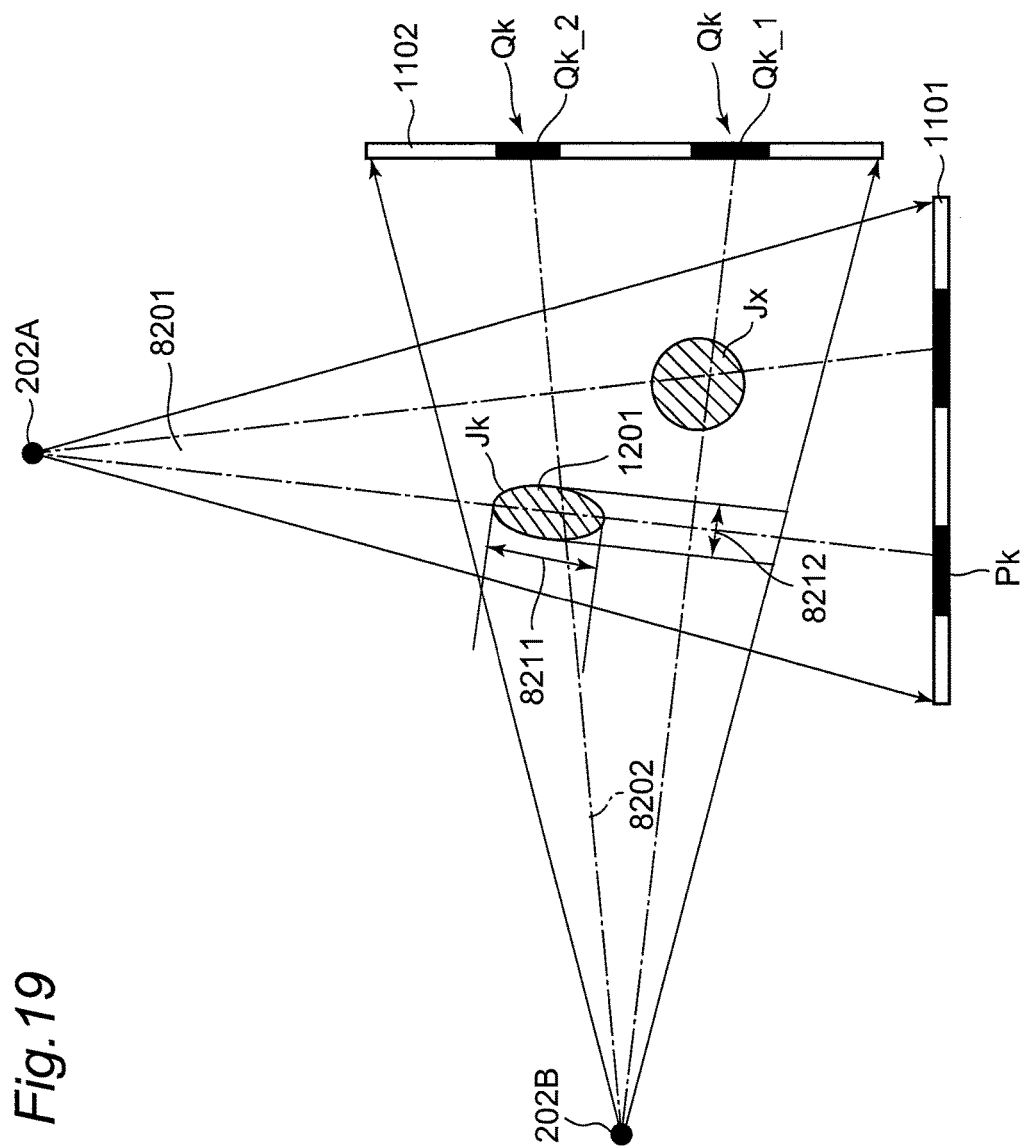
FIG. 19 is a view of an epipolar plane according to the second embodiment.

FIG. 19 is a view of an epipolar plane. A point on the blood vessel 1201 is assumed as the 3D point Jk in the above description. More particularly, a section of the blood vessel 1201 by the epipolar line has an area of an ellipse or the like as depicted in FIG. 19. The 3D point Jk will be hereinafter referred to as a 3D region Jk when taking into consideration that the section has an area. Furthermore, the first image projection point Pk and the second image projection point Qk as projection points of the 3D region Jk actually each have a length as a line segment. The first image projection point Pk and the second image projection point Qk will be hereinafter referred to as a first image projection region Pk and a second image projection region Qk when taking into consideration that the points each have a length.

Figure 17:
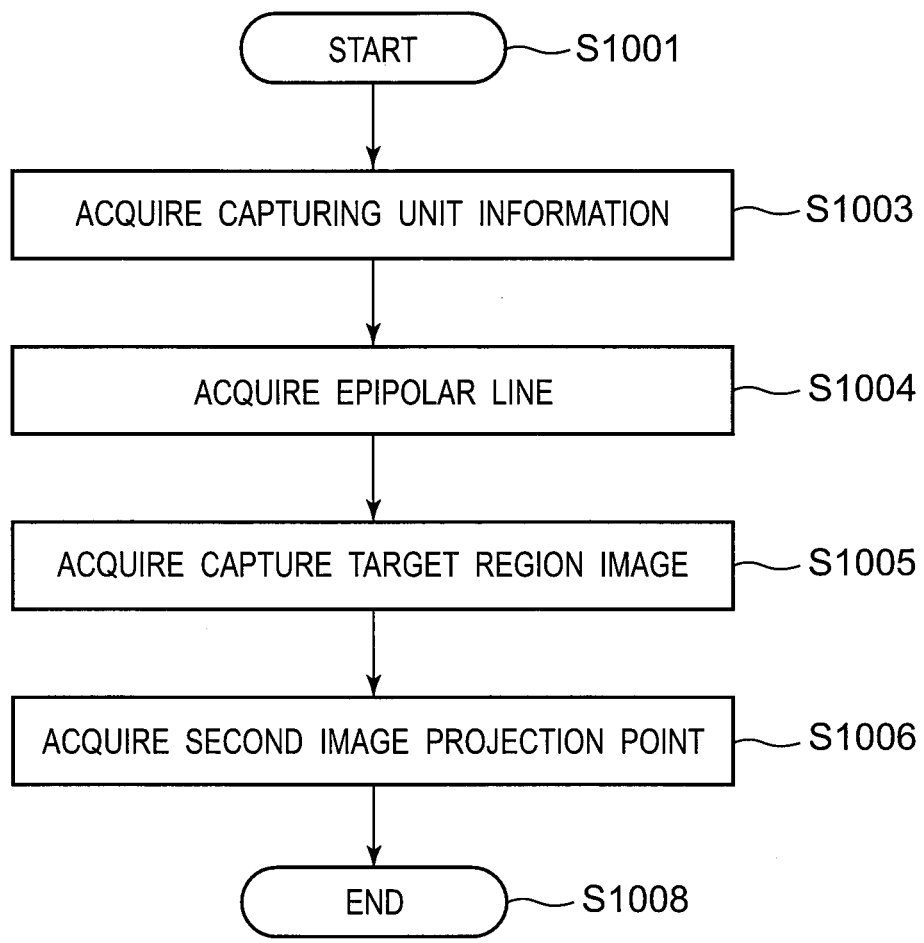
FIG. 17 is a flowchart of a second image projection region acquiring unit according to the second embodiment.

The second image projection region acquiring unit 1705 acquires a position of each of second image projection regions Qk_n (n=1, 2, . . . , and N; where N is the number of second image projection regions), as a candidate corresponding point for the first image projection point Pk designated by the mapping controller 1701 to be described later. A specific method will be described with reference to the flowchart in FIG. 17 of the processes executed by the capture target region acquiring unit 105.

The second image projection region acquiring unit 1705 starts the processes in step S1001.

Subsequently in step S1003, the second image projection region acquiring unit 1705 acquires the translation vector T, the rotation vector R, and the internal parameters A1 and A2 from the radiographing unit information storage 104.

Then, in step S1004, the second image projection region acquiring unit 1705 calculates the epipolar line L2 corresponding to the acquired first image projection region. The epipolar line L2 has a linear range in which a corresponding point of the first image projection point Pk possibly appears on a second screen and is determined in accordance with the position of the first image projection point Pk and a geometrical positional relation between the radiographing unit 101 and the radiographing unit 102.

The epipolar line L2 is calculated from the relative positional information on the positions of the radiographing unit 101 (the X-ray generator 202A) and the radiographing unit 102 (the X-ray generator 202B) (the translation vector T and the rotation vector R) and information on the camera used for capture (the internal parameters A1 and A2). More specifically, the second image projection region acquiring unit 1705 calculates a parameter 12 of the epipolar line L2 by calculation in accordance with Equations 6 and 7.

$$F = A1^{-T}[T]_x R A2^{-1} \quad \text{(Equation 6)}$$

$$l2 = Fm \quad \text{(Equation 7)}$$

In Equation 6, F denotes a determinant called a fundamental determinant, $A1^{-T}$ denotes a transpose of an inverse matrix of the internal parameter A1, and $[T]_x$ denotes a skew-symmetric matrix of the translation vector T. In this equation, m denotes position coordinates of the first image projection point Pk.

When the calculated parameter l2 of the epipolar line L2 is expressed as (a, b, c) T, the epipolar line L2 satisfies ax+by +c=0.

Subsequently in step S1005, the second image projection region acquiring unit 1705 acquires a second capture target region image 7902 from the capture target region image storage 1132.

Figures 20, 21, 22:
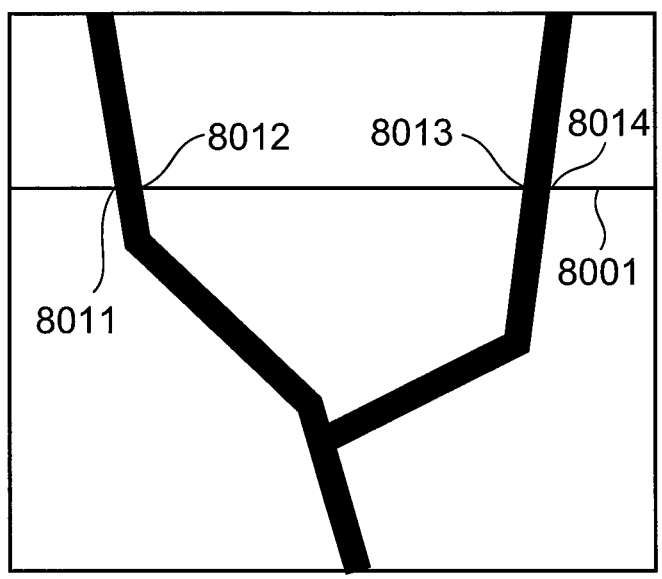
FIG. 20 is a view of second image projection regions Qk (k=1 and 2) according to the second embodiment.
FIG. 21 is an exemplary chart of data held by a second image projection region storage according to the second embodiment.
FIG. 22 is an exemplary chart of data held by a first image projection region storage according to the second embodiment.

Then, in step S1006, the second image projection region acquiring unit 1705 acquires a position of each of the second image projection regions Qk_n (n=1, 2, . . . , and N; where N is the number of second image projection regions), as an intersection point with the epipolar line L2 on the second capture target region image 7902. FIG. 20 is an exemplary view of the second image projection regions Qk (k=1, 2). Reference sign 8001 in FIG. 20 denotes the epipolar line L2. The thick line region in FIG. 20 indicates the capture target region including the blood vessel 1201 on the image 2_END that is captured by the radiographing unit 102. In FIG. 20, the second image projection regions Qk_n (n=1, 2) correspond to regions where the capture target region (the thick line region) and the epipolar line L2 cross each other. In the case of FIG. 20, a region on a line segment connecting a point 8011 and a point 8012 corresponds to the second image projection region Qk_1 and a region on a line segment connecting the point 8012 and a point 8013 corresponds to the second image projection region Qk_2. The second image projection region acquiring unit 1705 stores coordinates of points included in the respective regions in the second image projection region storage 1706.

The second image projection region acquiring unit 1705 then ends the processes in step S1008.

The second image projection region storage 1706 holds coordinates of the second image projection regions Qk_n (n=1, 2, . . . , and N) acquired by the second image projection region acquiring unit 1705. In the case of FIG. 20, the second image projection region acquiring unit 1705 acquires coordinates of the second image projection regions Qk_1 and Qk_2. FIG. 21 is an exemplary chart of data held by the second image projection region storage 1706. Coordinates of the points 8011 and 8012 are held in the first row, whereas coordinates of the points 8013 and 8014 are held in the second row. In the following description, respective pixels composing the second image projection region Qk_n will be denoted by qk_n_an (an=1, 2, . . . , and An; where An is the number of pixels composing the second image projection region Qk_n).

The first image projection region acquiring unit 1702C acquires a position of the first image projection region Pk for the first image projection point Pk designated by the mapping controller 1701 to be described later.

A specific method will be described below. A parameter l1 of the epipolar line L1 is initially calculated in accordance with Equation 8.

$$l1 = F^T m \quad \text{(Equation 8)}$$

In Equation 8, F indicates the determinant F calculated in accordance with Equation 6, and $F^T$ denotes a transpose of the determinant F. Furthermore, m denotes coordinates of a point in the arbitrary second image projection region Qk_n acquired from the second image projection region storage 1706.

When the calculated parameter l1 of the epipolar line L1 is expressed as (a, b, c) T, the epipolar line L1 satisfies ax+by +c=0. Coordinates of an intersection point between the calculated epipolar line L1 and the first capture target thin line image 1101T are acquired similarly to the case with the second image projection region acquiring unit 1705, and the method thereof will not be described repeatedly.

The first image projection region storage 1703C holds coordinates of the first image projection region Pk acquired by the first image projection region acquiring unit 1702C. FIG. 22 indicates exemplary coordinates in the first image projection region Pk. In the following description, respective pixels composing the first image projection region Pk will be denoted by pk_b (b=1, 2, . . . , and B; where B is the number of pixels composing the first image projection region Pk).

The absorption property will be described before description of the absorption property acquiring unit 1707.

In the epipolar plane depicted in FIG. 19, brightness of the first image projection point Pk is different from brightness of the second image projection point Qk_2, so that a corresponding point of the first image projection point Pk cannot be determined in accordance with brightness. The sum of thicknesses in a 3D region Jk_1 passed by X-rays generated by the X-ray generator 202A and reaching the first image projection region Pk (the total lengths of thick lines in FIG. 23) is, however, equal to the sum of thicknesses in the 3D region Jk passed by X-rays generated by the X-ray generator 202B and reaching the second image projection region Qk_2 (the total lengths of thick lines in FIG. 24). Furthermore, the total amount of the contrast medium passed by X-rays (the amount of substance absorbing X-rays) generated by the X-ray generator 202A and reaching the first image projection region Pk (the total amount of the contrast medium on the thick lines in FIG. 24) is equal to the total amount of the contrast medium passed by X-rays (the amount of substance absorbing X-rays) generated by the X-ray generator 202B and reaching the second image projection region Qk_2 (the total amount of the contrast medium on the thick lines in FIG. 23). A corresponding point of the first image projection region Pk is determined in accordance with these relations in the present embodiment.

Why mapping according to brightness is impossible will be described initially. In the epipolar plane depicted in FIG. 19, An X-ray 8201 passing the X-ray generator 202A and the 3D region Jk and reaching the first image projection point Pk passes a portion of the blood vessel 1201 at a thickness 8211. An X-ray 8202 passing the X-ray generator 202B and the 3D region Jk and reaching the second image projection point Qk_2 passes a portion of the blood vessel 1201 at a thickness 8212.

The thickness 8211 is different from the thickness 8212, so that brightness of the first image projection point Pk is different from brightness of the second image projection point Qk_2. Determination of a corresponding point of the first image projection point Pk according to brightness is thus difficult.

An area of the blood vessel 1201 that is passed by X-rays toward the first image projection region Pk and that reaches the first image projection region Pk is equal to an area of the blood vessel 1201 passed by X-rays toward the second image projection region Qk_2 and that reaches the second image projection region Qk_2.

Figure 23:
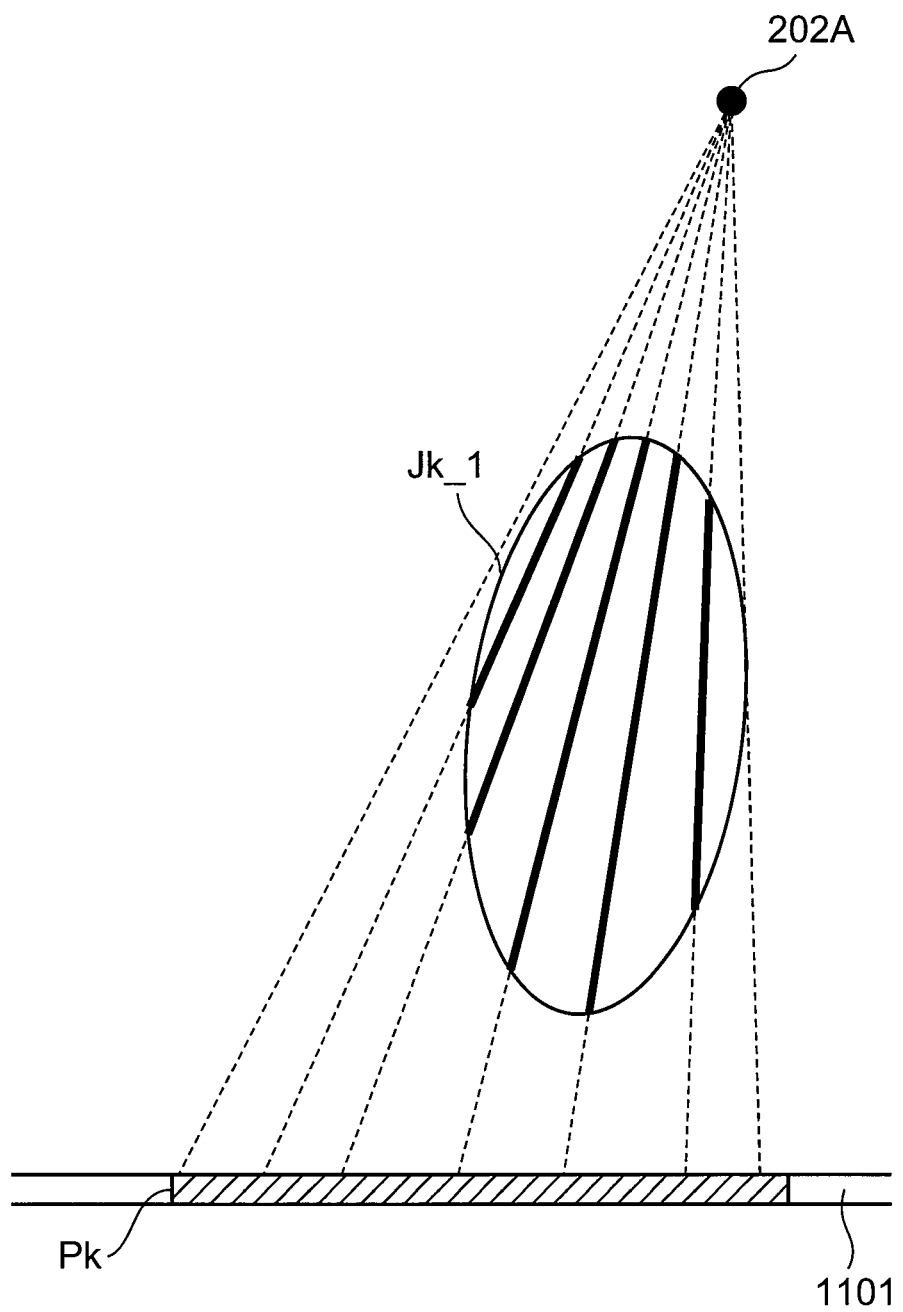
FIG. 23 is a view of an epipolar plane according to the second embodiment.

This relevance will be described with reference to FIGS. 23 and 24. FIG. 23 is a view indicating the area of the blood vessel 1201 that is passed by X-rays toward the first image projection region Pk and reaches the first image projection region Pk. For easier description, the 3D region Jk in this view is different in size and position from the 3D region Jk depicted in FIG. 19. The area of the blood vessel 1201 that is passed by X-rays toward the first image projection region Pk and reaches the first image projection region Pk can approximate to the total lengths of the thick lines in FIG. 23.

Figure 24:
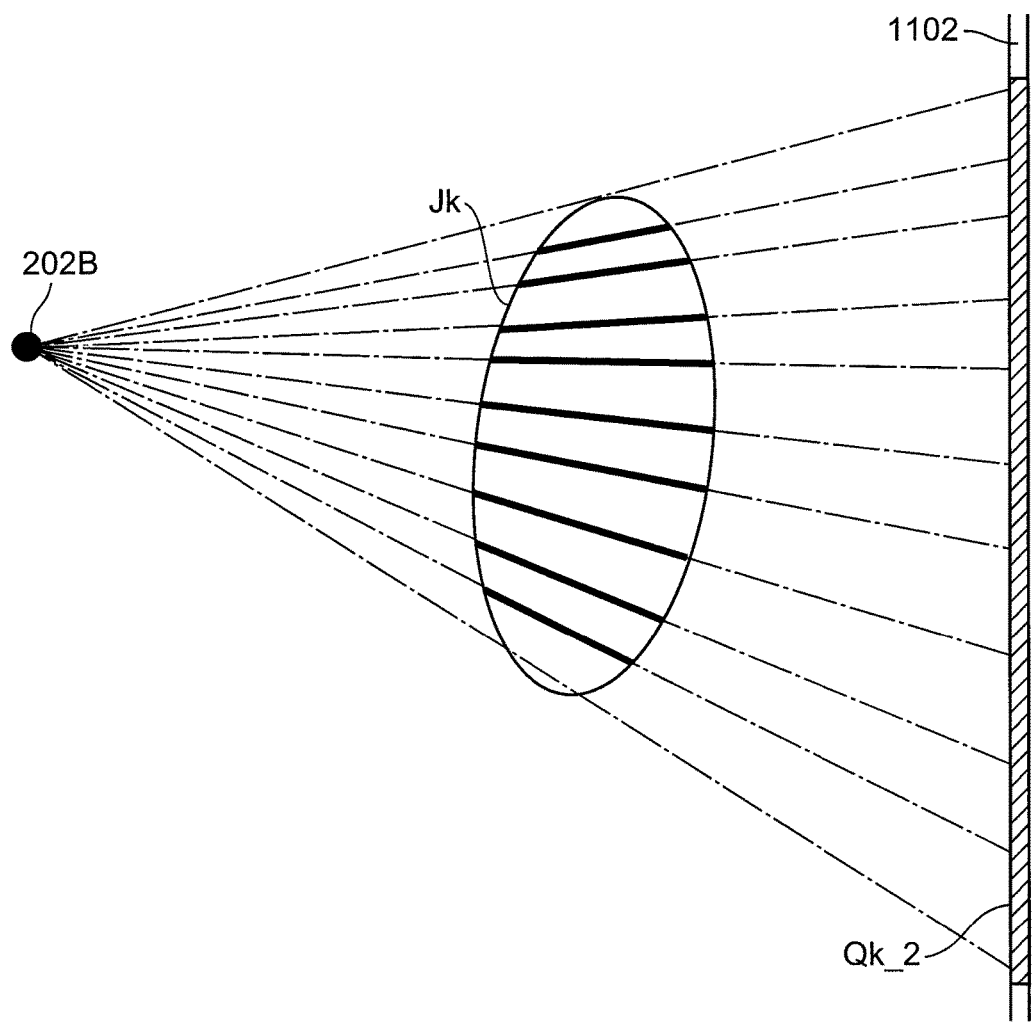
FIG. 24 is a view of an epipolar plane according to a modification example 2 of the second embodiment.

FIG. 24 is a view indicating the area of the blood vessel 1201 that is passed by X-rays toward the second image projection region Qk_2 and reaches the second image projection region Qk_2. The area of the blood vessel 1201 that is passed by X-rays toward the first image projection region Pk and reaches the first image projection region Pk can approximate to the total lengths of the thick lines in FIG. 24. The area in FIG. 23 is equal to the area in FIG. 24. The amount of the contrast medium on the thick lines (the amount of substance absorbing X-rays) in FIG. 23 is also equal to that in FIG. 24.

According to the second embodiment of the present disclosure, the absorption property acquiring unit 1707 estimates the area or the amount of the contrast medium from brightness of a point in the first capture target region on the X-ray image.

The principle will be described below. An X-ray of the intensity $I_0$ is attenuated to have the intensity I by passing an object of a thickness d [cm]. When a linear attenuation coefficient indicative of an attenuation degree is denoted by $\mu$ [cm$^{-1}$], Equation 9 is obtained.

$$I = I_0 \times e^{-\mu \cdot d} \quad \text{(Equation 9)}$$

Equation 8 is also applicable to each of the pixels pk_b composing the first image projection region Pk. When intensity of an X-ray acquired at the pixel pk_b (brightness of the pixel pk_b) is denoted by I_b, and a thickness of the 3D region Jk passed by X-rays reaching the pixel pk_b is denoted by d_b, Equation 10 is obtained.

$$I\_b = I_0 \times e^{-\mu \cdot d\_b} \quad \text{(Equation 10)}$$

When logarithms of the both members of the equation are obtained and the absorption property acquiring unit 1707 calculates the sum of b=1, 2, . . . , and B (where B is the number of pixels composing the first image projection region Pk as already described), Equation 11 is obtained.

$$\sum_{b=1}^{B} \log I\_b = \sum_{b=1}^{B} \log(I_0 \times e^{-\mu \cdot d\_b}) = \sum_{b=1}^{B} \log I_0 + \sum_{b=1}^{B} \log e^{-\mu \cdot d\_b} = B \log I_0 - \mu \sum_{b=1}^{B} d\_b \quad \text{(Equation 11)}$$

Equation 12 is obtained by modifying Equation 11.

$$\mu \sum_{b=1}^{B} d\_b = B \log I_0 - \sum_{b=1}^{B} \log I\_b \quad \text{(Equation 12)}$$

Equation 8 is also applicable to each of the pixels qk_n_an composing the second image projection region Qk_n. When intensity of the pixel qk_n_an is denoted by Ian and a thickness of the 3D region Jk passed by X-rays reaching the pixel qk_n_an is denoted by d_an, Equation 13 is obtained similarly.

$$\mu \sum_{an=1}^{An} d\_an = An \log I_0 - \sum_{an=1}^{An} \log I\_an \quad \text{(Equation 13)}$$

In Equation 12, $\Sigma d\_b$ denotes a sectional area of the 3D region Jk. When the second image projection region Qk_n is the corresponding point of the first image projection region Pk, $\Sigma d\_an$ in Equation 13 also denotes a sectional area of the 3D region Jk. Equations 12 and 13 have equal values in this case. A 3D region Jx has a substantially elliptical shape or a plurality of aligned elliptical shapes indicating the region of the section of the blood vessel 1201 by the epipolar plane.

According to the second embodiment of the present disclosure, the corresponding region determiner 1711 determines, as a corresponding point of the first image projection region Pk, a second image projection region Qk_x having the value of Equation 13 most approximate to the value of Equation 12 out of the second image projection regions Qk_n (n=1, 2, . . . , and N). In the following description, the value of Equation 12 will be called an absorption property $\lambda$_pk whereas the value of Equation 13 will be called an absorption property $\lambda$_qk_n.

The absorption property acquiring unit 1707 calculates an absorbed X-ray amount in the first image region Pk exemplifying the absorption property according to the second embodiment, as a difference between a product of logarithms of the number of pixels in the projection region (the first image region Pk) and intensity of the X-ray emitted from the X-ray generator in the first radiographing unit and logarithm sums of intensities of X-rays acquired at the respective pixels in the projection region (the first image region Pk). The absorption property acquiring unit 1707 also calculates an absorbed X-ray amount in the second image region Qk exemplifying the absorption property according to the second embodiment, as a difference between a product of logarithms of the number of pixels in the projection region (the second image region Qk) and intensity of the X-ray emitted from the X-ray generator in the second radiographing unit and logarithm sums of intensities of X-rays acquired at the respective pixels in the projection region (the second image region Qk).

Described herein is a case where the linear attenuation coefficient $\mu$ of the section of the 3D region Jk is constant. Even when the section includes very small regions having different linear attenuation coefficients, the sum of the linear attenuation coefficients is constant regardless of the capture direction, and thus, mapping can be achieved in accordance with the present disclosure.

The absorption property acquiring unit 1707 acquires a value at each time, of the absorption property $\lambda$_Pk for the first image projection point Pk designated by the mapping controller 1701. The absorption property acquiring unit 1707 acquires a value at each time, of the absorption property $\lambda$_Qk_n for each of the second image projection regions Qk_n (n=1, 2, . . . , and N). In the following description, the absorption properties at each of times t (t=1, 2, . . . , and END) will be denoted by $\lambda$_Pk_t and $\lambda$_Qk_n_t.

Figure 25:
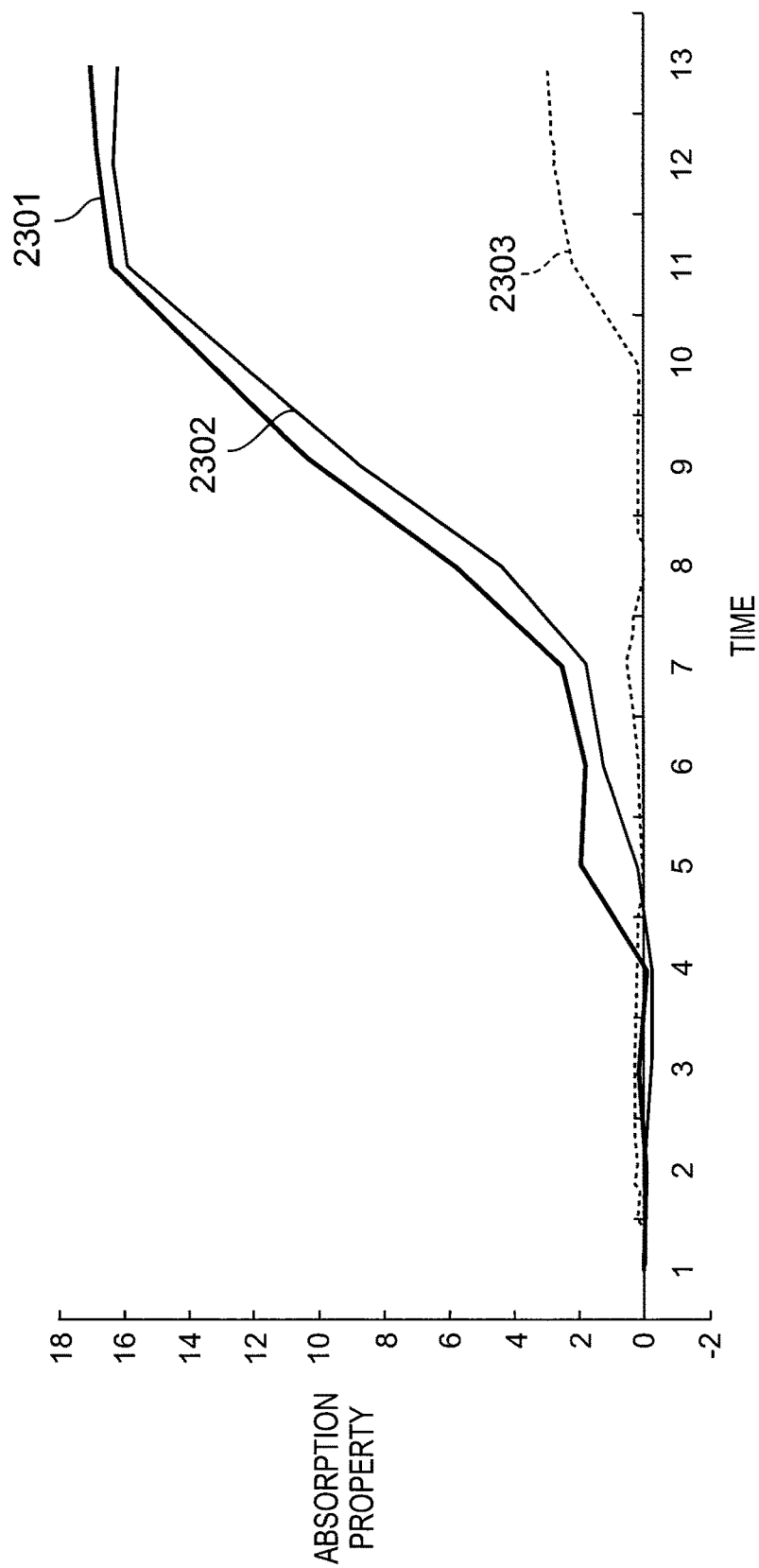
FIG. 25 is a graph indicating absorption properties of a first image projection point Pk and second image projection regions Qk_1 and Qk_2 according to the second embodiment.

FIG. 25 is an exemplary graph of absorption properties acquired by the absorption property acquiring unit 1707. A thick line 2301, a solid line 2302, and a dotted line 2303 in FIG. 25 indicate absorption property changes in the first image projection region Pk, the second image projection region Qk_1, and the second image projection region Qk_2, respectively. The transverse axis in the graph indicates time and each scale indicates 33 msec. The ordinate axis in the graph indicates an absorption property. This graph indicates absorption property changes at a stage where a contrast medium is injected into the blood vessel 1201 and the contrast medium in the blood vessel 1201 is increasing in concentration as time elapses (in other words, within a predetermined time period).

FIG. 27 is a chart of a data structure of absorption properties held by the absorption property storage 1708. Data of the absorption properties acquired by the absorption property acquiring unit 1707 includes the absorption properties λ_Pk_t (t=0, 2, . . . , and END) of the first image projection point Pk and the absorption properties λ_Qk_n_t (n=1, 2, . . . , and N, and t=0, 1, . . . , and END) of the second image projection region Qk_n. In other words, the absorption property acquiring unit 1707 acquires, as an absorption property, a change in absorbed X-ray amount in the first image region Pk from brightness of the contrast medium for the predetermined time period, and acquires, as an absorption property, a change in absorbed X-ray amount in each of the plurality of second image regions Qk from brightness of the contrast medium for the predetermined time period.

The absorption property storage 1708 holds the absorption properties (absorption property changes) acquired by the absorption property acquiring unit 1707. FIG. 27 is a chart of absorption properties (absorption property changes) held by the absorption property storage 1708 in a case where there are two second image projection regions Qk_n.

The absorption property evaluator 1709 evaluates each of the second image projection regions Qk_n (n=1, 2, . . . , and N) held by the absorption property storage 1708.

The absorption property evaluator 1709 calculates, as an example of similarity degree according to the first embodiment, an evaluation value regarding whether each of the absorption properties of the second image projection regions Qk_n (n=1, 2, . . . , and N) held by the absorption property storage 1708 changes similarly to or differently from the absorption property of the first image projection point Pk, and stores the calculated evaluation value in the absorption property evaluation storage 1710. Such evaluation is performed in accordance with Equation 14 in the second embodiment. In other words, the absorption property evaluator 1709 calculates, as an evaluation value, a similarity degree between an absorption property change of each of the second image projection regions Qk_n (n=1, 2, . . . , and N) held by the absorption property storage 1708 and an absorption property change of the first image projection point Pk.

$$H\_n = \sum_{t=1}^{END} |\lambda\_Pk\_t - \lambda\_Qk\_n\_t| \quad \text{(Equation 14)}$$

In this equation, |X| indicates the absolute value of X. An evaluation value H_n in Equation 14 in the second embodiment is thus the sum of the absolute values of differences between the absorption properties λ_Pk of the first image projection point Pk and the absorption properties λ_Qk_n of the second image projection region Qk_n at the respective times t (from t=0 to t=END).

Figure 28:
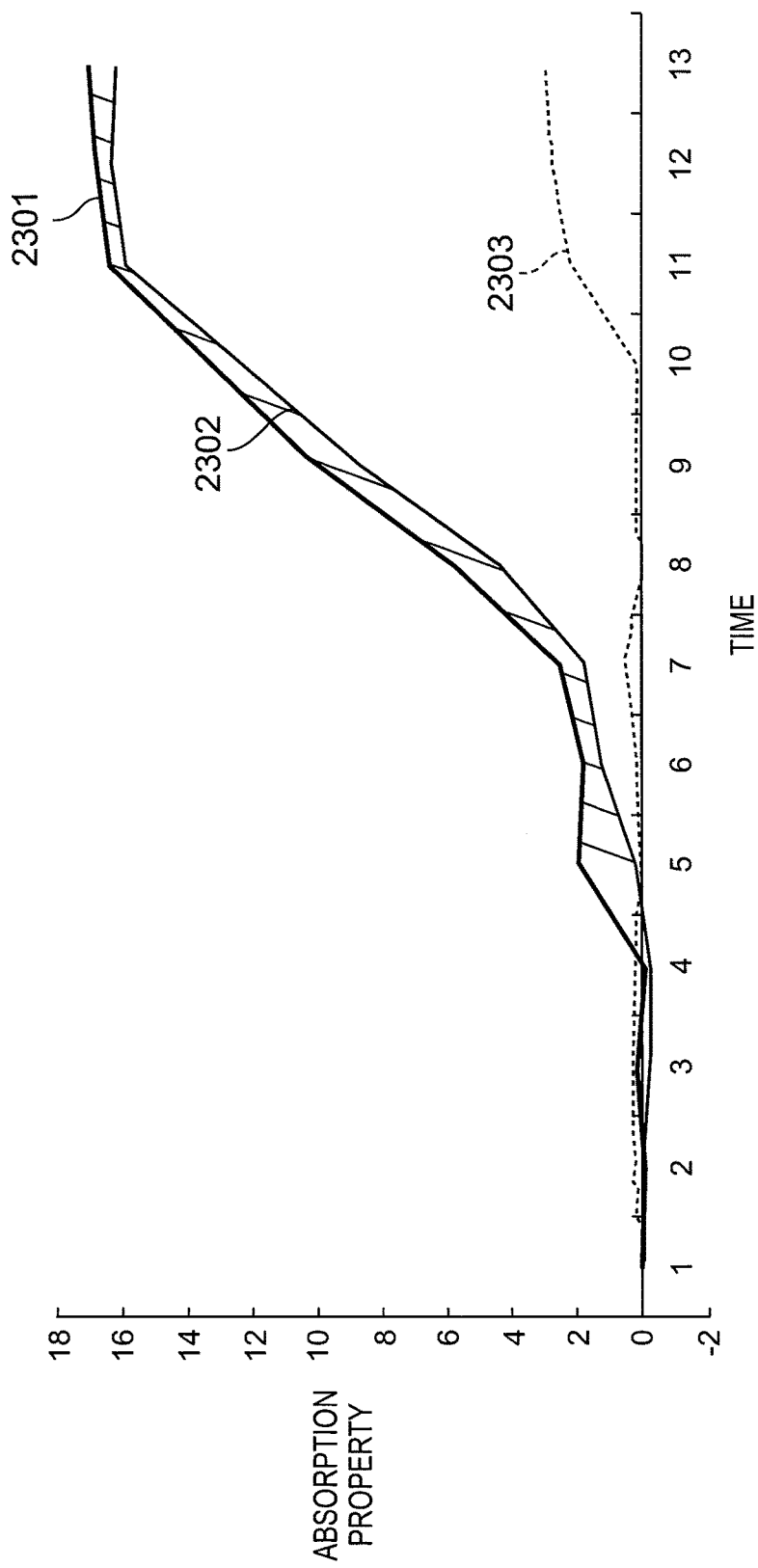
FIG. 28 is a graph indicating an evaluation value for the second image projection region Qk_1 according to the second embodiment.
Figure 29:
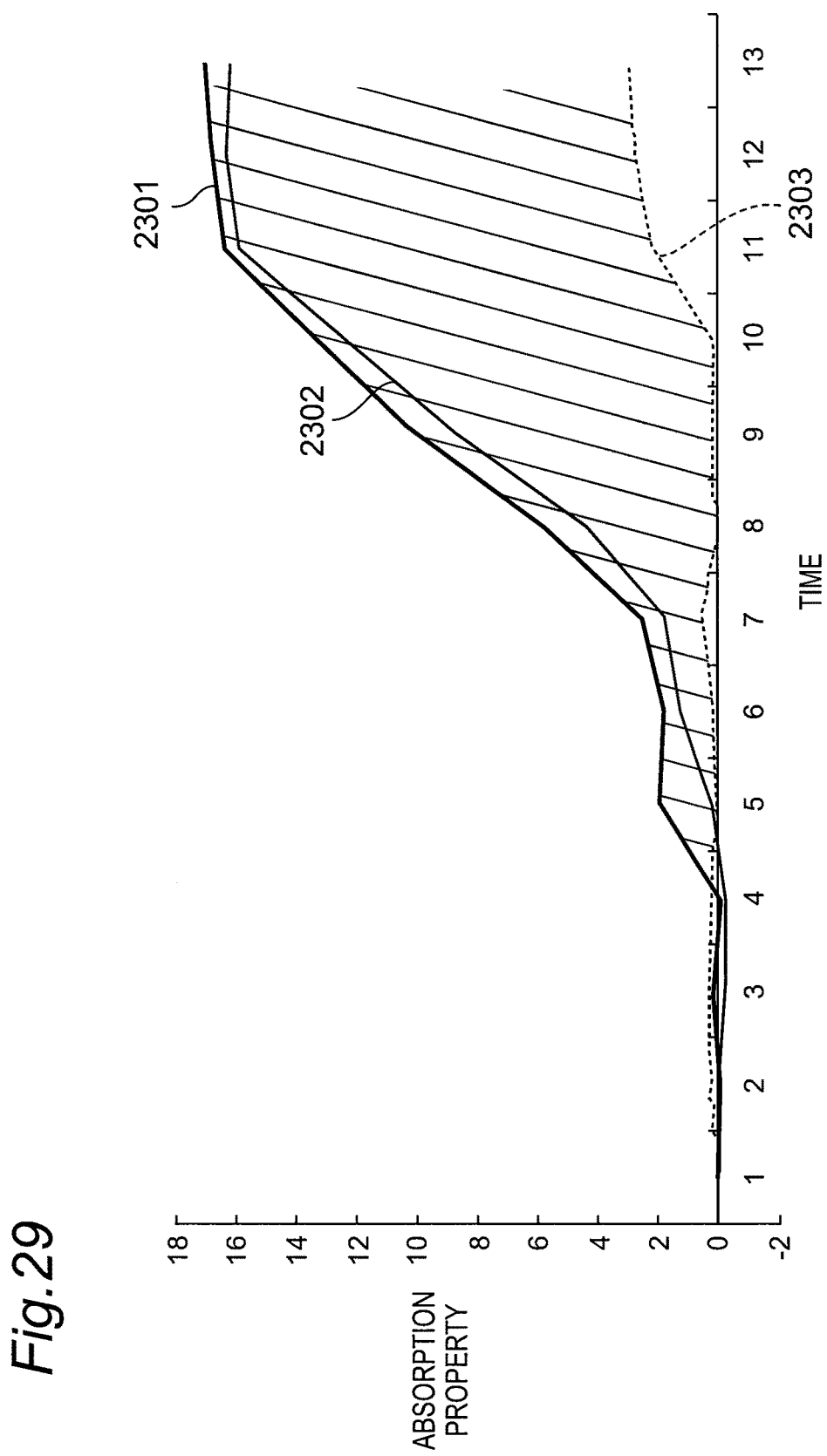
FIG. 29 is a graph indicating an evaluation value for the second image projection region Qk_2 according to the second embodiment.

FIG. 28 is a graph indicating the evaluation value for the second image projection region Qk_1. The thick line 2301 and the solid line 2302 in FIG. 28 indicate the absorption properties of the first image projection region Pk and the second image projection region Qk_1. The evaluation value for the second image projection region Qk_1 corresponds to the area of the shaded region between the thick line 2301 and the solid line 2302 in FIG. 28. FIG. 29 is a graph indicating the evaluation value for the second image projection region Qk_2. The thick line 2301 and the dotted line 2303 in FIG. 29 indicate the absorption properties of the first image projection region Pk and the second image projection region Qk_2. The evaluation value for the second image projection region Qk_2 corresponds to the area of the shaded region between the thick line 2301 and the dotted line 2303 in FIG. 29.

The absorption property evaluation storage 1710 holds the evaluation values H_n (n=1, 2, . . . , and N) for the absorption properties of the respective second image projection regions Qk_n (n=1, 2, . . . , and N) calculated and acquired by the absorption property evaluator 1709.

The corresponding region determiner 1711 selects the minimum evaluation value from the evaluation values H_n (n=1, 2, . . . , and N) held by the absorption property evaluation storage 1710. When the corresponding region determiner 1711 selects an evaluation value H_x (where x is selected from n=1, 2, . . . , and N for the minimum evaluation value), the corresponding region determiner 1711 determines the second image projection region Qk_n (where n=x) as the corresponding region Qk of the first image projection region Pk. In a case where evaluation values H_1 and H_2 correspond to the areas of the shaded regions in FIGS. 28 and 29, respectively, the corresponding region determiner 1711 determines the second image projection region Qk_1 having the smaller area as the corresponding point Qk of the first image projection region Pk.

Figure 26:
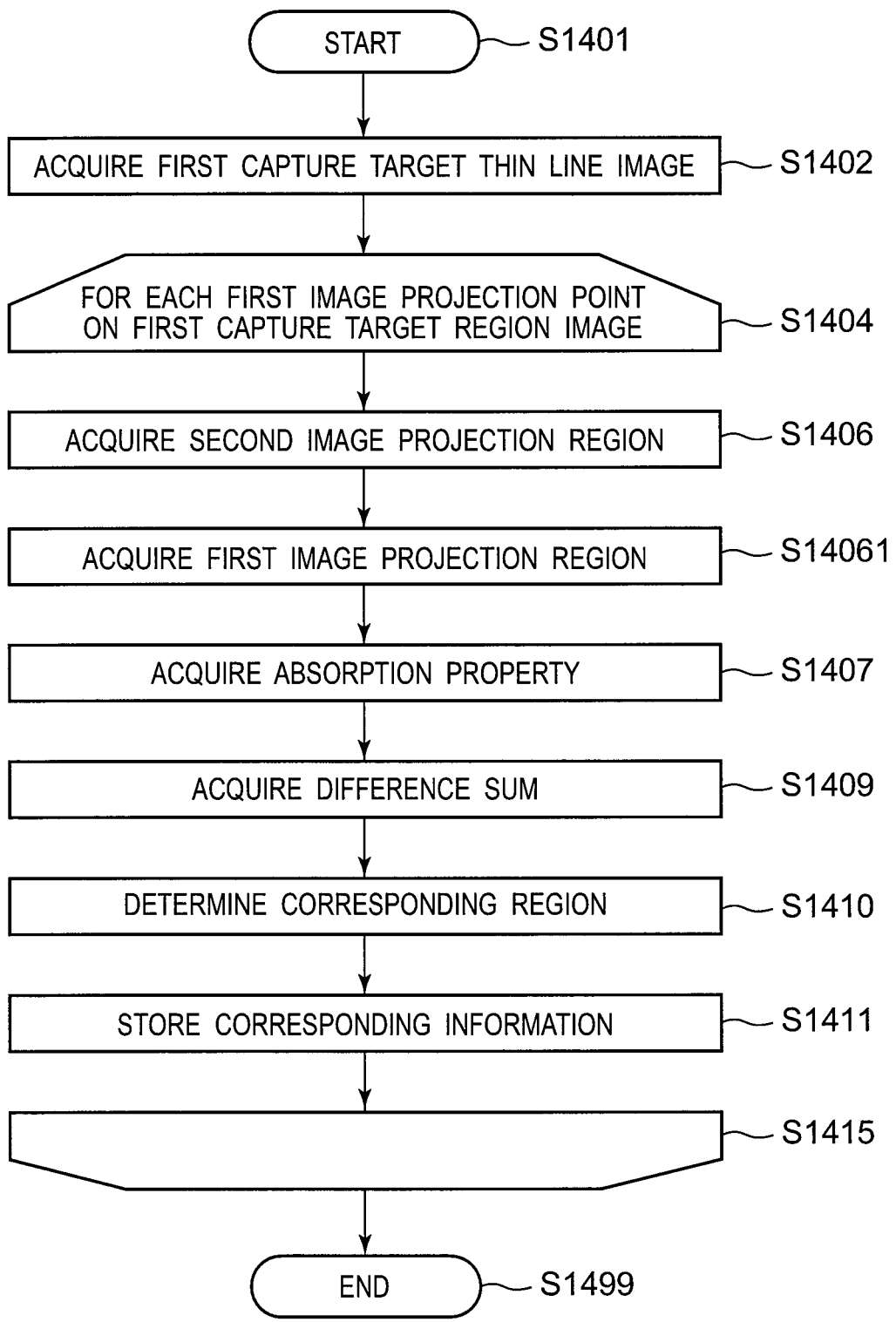
FIG. 26 is a flowchart of a mapping controller according to the second embodiment.

The mapping controller 1701 controls the respective units composing the mapping unit 107 to perform mapping. FIG. 26 is a flowchart of a flow of the processes executed by the mapping controller 1701.

The mapping controller 1701 starts the processes in step S1401.

Subsequently in step S1402, the mapping controller 1701 acquires the first capture target thin line image 1101T from the capture target thin line image storage 106.

The mapping controller 1701 then executes the processes in steps S1404 to S1415 to a black point in the capture target region on the first capture target thin line image 1101T acquired in step S1402. The black point will be called each of the first image projection points Pk (k=1, 2, . . . , and K; where K is the number of black points) in the following description.

Initially in step S1406, the mapping controller 1701 causes the second image projection region acquiring unit 1705 to acquire the second image projection regions Qk_n (n=1, 2, . . . , and N) for the first image projection point Pk, and store a coordinate of the acquired second image projection regions Qk_n (n=1, 2, . . . , and N) in the second image projection region storage 1706.

Subsequently in step S14061, the mapping controller 1701 causes the first image projection region acquiring unit 1702C to acquire the first image projection region Pk for the first image projection point Pk, and store coordinates of the acquired first image projection region Pk in the first image projection region storage 1703C.

In step S1407, the mapping controller 1701 causes the absorption property acquiring unit 1707 to respectively acquire the absorption properties of the first image projection region Pk and the second image projection regions Qk_n (n=1, 2, . . . , and N) and store the absorption properties in the absorption property storage 1708.

In step S1409, the mapping controller 1701 causes the absorption property evaluator 1709 to acquire the evaluation values (the difference sums) for the second image projection regions Qk_n (n=1, 2, . . . , and N) and store the evaluation values in the absorption property evaluation storage 1710.

In step S1410, the mapping controller 1701 causes the corresponding region determiner 1711 to determine the corresponding region Qk of the first image projection region Pk. More specifically, the corresponding region determiner 1711 selects the second image projection region Qk_x having the minimum evaluation value from the evaluation values H_n held by the absorption property evaluation storage 1710. The corresponding region determiner 1711 regards a minimum evaluation value Hk as the evaluation value for the corresponding region Qk.

In step S1411, the mapping controller 1701 stores the coordinate of the first image projection point Pk, the coordinate of the corresponding region Qk, and the evaluation value Hk for the corresponding region Qk in the corresponding information storage 108, and ends the processes from step S1404.

Then, the mapping controller 1701 ends the processes in step S1499.

The corresponding information storage 108 stores coordinates of gravity centers of the first image projection regions Pk (k=1, 2, . . . , and K; where K is the number of first image projection points), coordinates of gravity centers of the corresponding regions Qk (k=1, 2, . . . , and K), and the evaluation values Hk (k=1, 2, . . . , and K) for the corresponding regions Qk, which are acquired by the mapping unit 107. FIG. 30 indicates a data structure in the corresponding information storage 108. The corresponding information storage 108 holds no set in the initial state. One row of data is added to the corresponding information storage 108 every time the mapping controller 1701 executes the process in step S1411.

The 3D position acquiring unit 109 calculates coordinates of the 3D points Jk on the 3D from the coordinates of the gravity centers of the first image projection regions Pk in respective rows and the coordinates of the gravity centers of the corresponding regions Qk in the respective rows held by the corresponding information storage 108 in accordance with the triangulation principle, and stores the calculated coordinates of the 3D points Jk (k=1, 2, . . . , and K) in the 3D position storage 110.

The 3D position storage 110 holds the coordinates of the 3D points Jk (k=1, 2, . . . , and K) restored by the 3D position acquiring unit 109. FIG. 31 is a chart of a data structure in the 3D position storage 110. The 3D position storage 110 holds coordinates (JK_X, JK_Y, JK_Z) in a row K (k=K). The 3D point Jk has X, Y, and Z coordinates of JK_X, JK_Y, and JK_Z, respectively.

Figure 32:
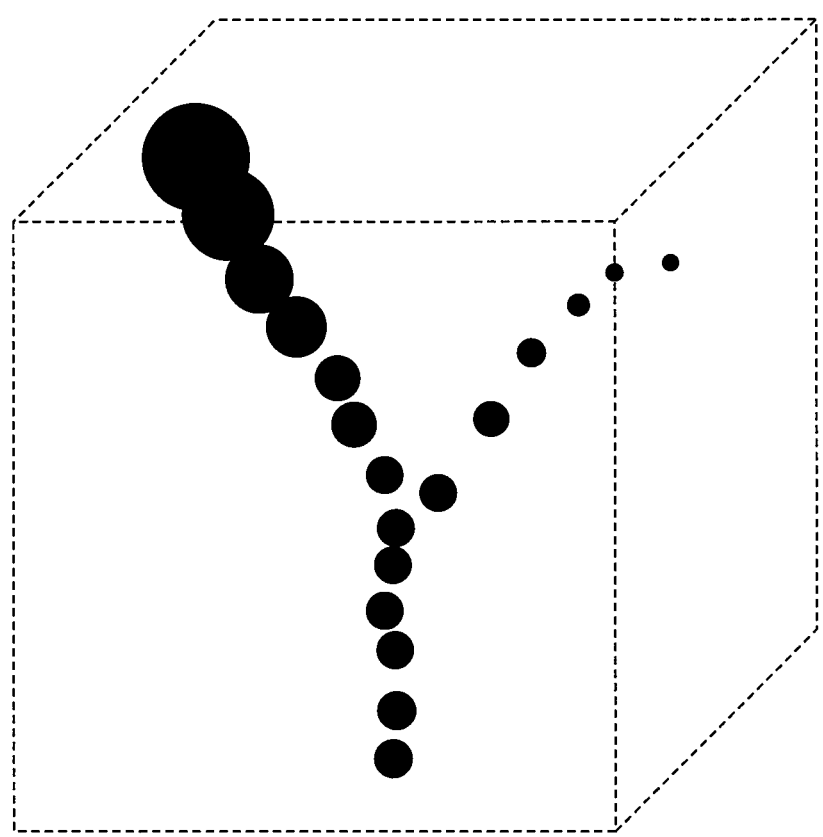
FIG. 32 is a view of a display screen generated by a display screen generator according to the second embodiment.

The display screen generator 111 generates a computer graphics (CG) screen displaying the 3D point Jk (k=1, 2, . . . , and K) held by the 3D position storage 110. FIG. 32 is an exemplary view of the display screen generated by the display screen generator 111. Each 3D point is indicated by a sphere in an exemplary 3D display manner in FIG. 32, but each 3D point can be indicated in any other manner. For example, the adjacent 3D points can be connected by a column and displayed as a polygon.

The display unit 112 displays a screen generated by the display screen generator 111. More particularly, the display unit 112 is a display device such as a display or a projector.

<Flow of Processes Executed by Shape Restoring Apparatus 1>

Figure 33:
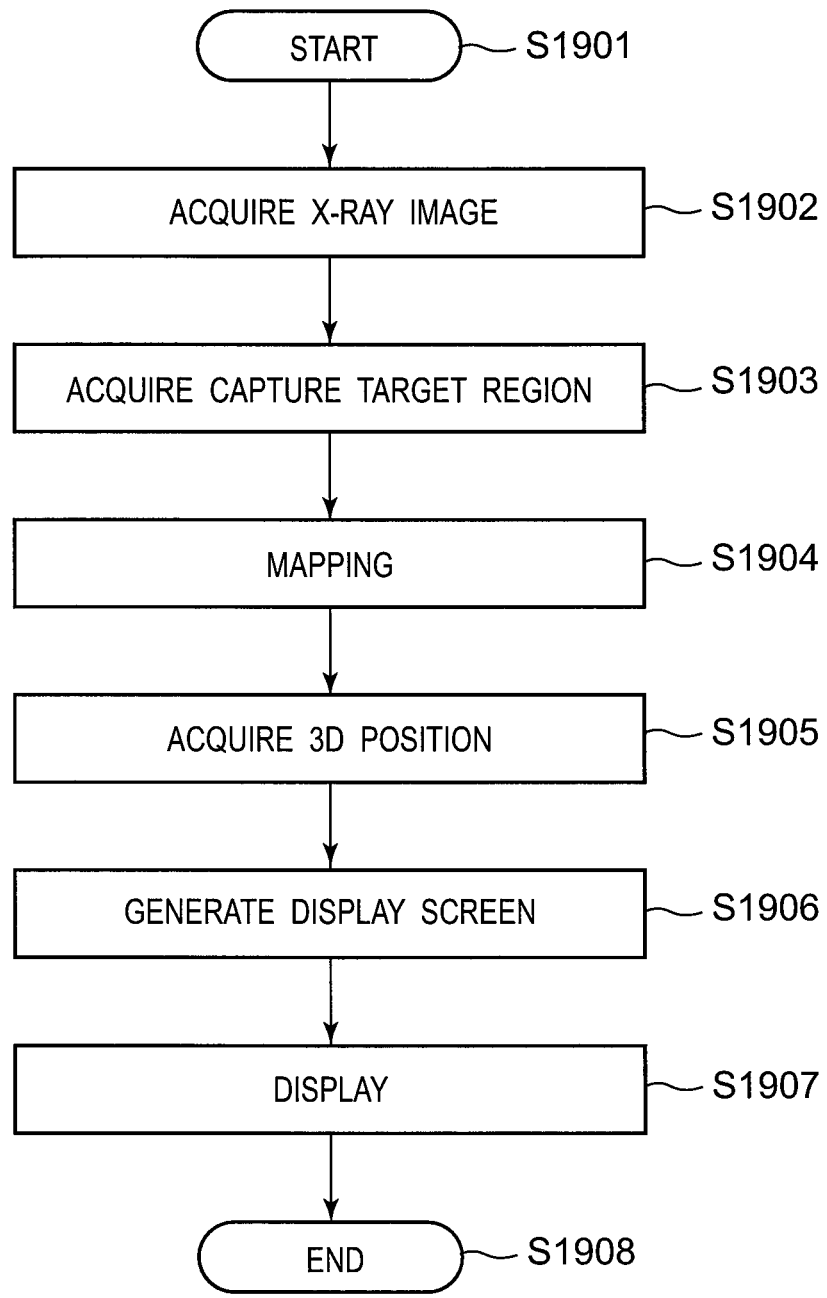
FIG. 33 is a flowchart of the shape restoring apparatus according to the second embodiment.

FIG. 33 is a flowchart of the processes executed by the shape restoring apparatus 1.

Firstly, the shape restoring apparatus 1 starts the processes in step S1901.

Subsequently in step S1902, the X-ray image acquiring unit 113 executes the above-described process of the X-ray image acquiring unit 113. More specifically, the X-ray image acquiring unit 113 acquires X-ray images from the radiographing units 101 and 102 and stores the acquired X-ray images in the X-ray image storage 103.

Subsequently in step S1903, the capture target region acquiring unit 105 executes the above-described process of the capture target region acquiring unit 105. More specifically, the capture target region acquiring unit 105 acquires the first and second capture target thin line images 1101T and 1102T in accordance with the images held by the X-ray image storage 103, and stores the first and second capture target thin line images 1101T and 1102T thus acquired in the capture target thin line image storage 106.

Subsequently in step S1904, the mapping unit 107 executes the above-described process of the mapping unit 107. More specifically, the mapping unit 107 determines the corresponding region Qk of each of the first image projection regions Pk (k=1, 2, . . . , and K) on the first capture target thin line image 1101T held by the capture target thin line image storage 106, and stores corresponding information in the corresponding information storage 108.

Subsequently in step S1905, the 3D position acquiring unit 109 executes the above-described process of the 3D position acquiring unit 109. More specifically, the 3D position acquiring unit 109 calculates a 3D position of the 3D point Jk for each of the first image projection regions Pk (k=1, 2, . . . , and K) on the first capture target thin line image 1101T in accordance with the corresponding information held by the corresponding information storage 108, and stores the 3D positions in the 3D position storage 110.

In step S1906, the display screen generator 111 generates a CG screen displaying each 3D point Jk (k=1, 2, . . . , and K) in accordance with the 3D position of the 3D point Jk held by the 3D position storage 110.

Then in step S1907, the display unit 112 displays the screen generated by the display screen generator 111. The series of processes then end in step S1908.

<Principle of Processes Executed by Shape Restoring Apparatus 1>

When a contrast medium is injected into the blood vessel 1201, the contrast medium staying at the 3D point Jk on the blood vessel 1201 changes in amount as time elapses. The first image projection point Pk obtained by capturing the 3D point Jk and the corresponding point Qk change in brightness in this case. The shape restoring apparatus 1 causes the absorption property acquiring unit 1707 to acquire absorption property changes of the first image projection point Pk and the second image projection points Qk_n (n=1, 2, . . . , and N), causes the absorption property evaluator 1709 to evaluate similarity (a similarity degree) of the brightness change as an evaluation value, and causes the corresponding region determiner 1711 to determine the corresponding point Qk out of the second image projection points Qk_n.

Figure 34:
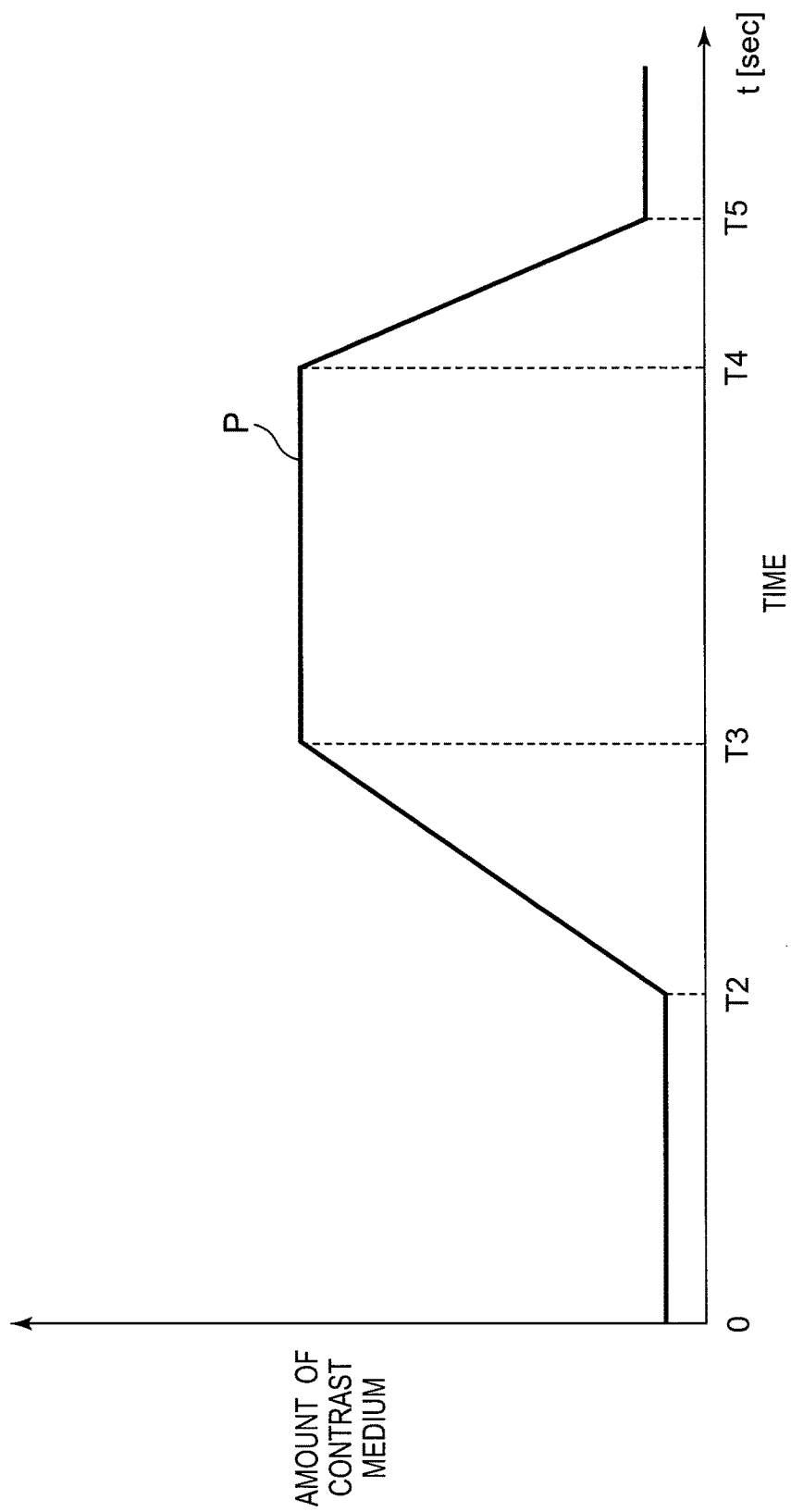
FIG. 34 is a graph indicating an amount of a contrast medium flowing to a 3D point J1 according to the second embodiment.

A change in amount of the contrast medium at the 3D point Jk on the blood vessel 1201 will be described initially. FIG. 34 indicates a change in amount of a contrast medium at a certain 3D point Jk. Any contrast medium does not flow before a contrast medium is injected (until a time T2). The contrast medium starts flowing gradually from the time T2 and flows constantly at a time T3. The contrast medium starts decreasing gradually from a time T4 and does not flow at a time T5.

Such a change in amount of the contrast medium in the blood vessel 1201 with time differs at portions of the blood vessel. For example, the change in amount of the contrast medium with time at the time T2 when the contrast medium starts flowing is fast at a position close to a point of jetting the contrast medium. In contrast, the change in amount of the contrast medium with time at the time T2 when the contrast medium starts flowing is slow at a position distant from the point of jetting the contrast medium. The change in amount of the contrast medium with time at the time T4 when the contrast medium decreases also differs at portions of the blood vessel.

The change in amount of the contrast medium with time from the time T2 when the contrast medium starts flowing to the time T3 when the contrast medium flows constantly also differs at portions of the blood vessel. For example, at a portion where blood flows upward, the contrast medium flows against the gravity and it takes a long time period for the contrast medium to increase concentration. A time period (T3-T2) required for the contrast medium to be constant in concentration is thus long. In contrast, at a portion where the contrast medium flows downward, the contrast medium is increased in speed by the gravity. The time period (T3-T2) required for the contrast medium to be constant in concentration is thus short. Blood flows fast in a narrow blood vessel and the time period (T3-T2) required for the contrast medium to be constant in concentration is thus short. In contrast, blood flows slowly in a wide blood vessel and the time period (T3-T2) required for the contrast medium to be constant in concentration is thus long. As described above, the contrast medium flowing at a certain portion of the blood vessel changes in amount with time, and how the contrast medium changes in amount differs at portions of the blood vessel. A time period (T5-T4) from the start to the end of decrease of the contrast medium also differs at portions of the blood vessel.

Brightness changes at the first image projection point Pk and the corresponding point Qk in a case where the contrast medium at the 3D point Jk changes in concentration will be described next. Brightness of the first image projection point Pk that is obtained by projecting the 3D point Jk on an X-ray image changes at a degree similar to the concentration change of the contrast medium at the 3D point Jk. The first image projection point Pk and the corresponding point Qk are decreased in brightness when the contrast medium at the 3D point Jk is increased in concentration. In contrast, the first image projection point Pk and the corresponding point Qk are increased in brightness when the contrast medium at the 3D point Jk is decreased in concentration. The first image projection point Pk and the corresponding point Qk are obviously changed in brightness at a degree similar to the concentration change of the contrast medium.

Figure 61:
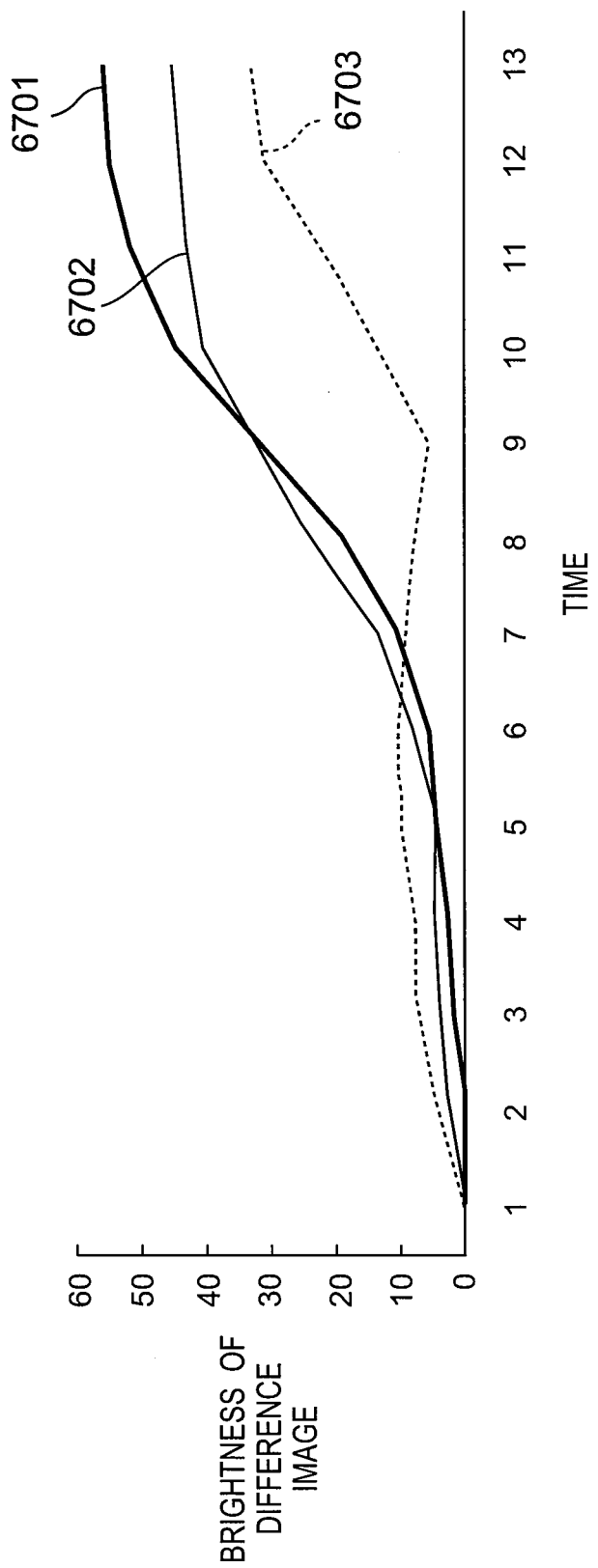
FIG. 61 is a graph indicating brightness sequences of the first image projection point Pk and candidate corresponding points Qk_1 and Qk_2 according to the second embodiment.

FIG. 61 indicates brightness sequences at the first image projection point Pk as a point in the first image region Pk and the corresponding point Qk as a point in the corresponding region Qk in a case where a certain 3D region Jk is captured in two different directions. In FIG. 61, a thick line 6701 indicates the brightness sequence of the first image projection point Pk of the 3D region Jk, and a solid line 6702 indicates the brightness sequence of the corresponding point Qk. A dotted line 6703 indicates a brightness change of a point Qx as a point in a region Qx obtained by capturing the 3D region Jx (x≠k) that is different from the 3D region Jk in a second direction. The transverse axis in the graph indicates time and each scale indicates 33 msec. The ordinate axis indicates brightness of a difference image. This graph indicates brightness from the time when the contrast medium is injected to the time when the contrast medium is stabilized halfway in concentration. In this graph, the brightness sequences of the first image projection point Pk and the corresponding point Qk are increased and decreased at similar degrees, but the brightness sequences of the first image projection point Pk and the corresponding point Qx are changed at different degrees.

However, the brightness itself of the first image projection point Pk and the brightness itself of the corresponding point Qk do not match each other as indicated in FIG. 61. For example, the first image projection point Pk has brightness "56" whereas the corresponding point Qk has brightness "46" at a time 13.

Figure 35:
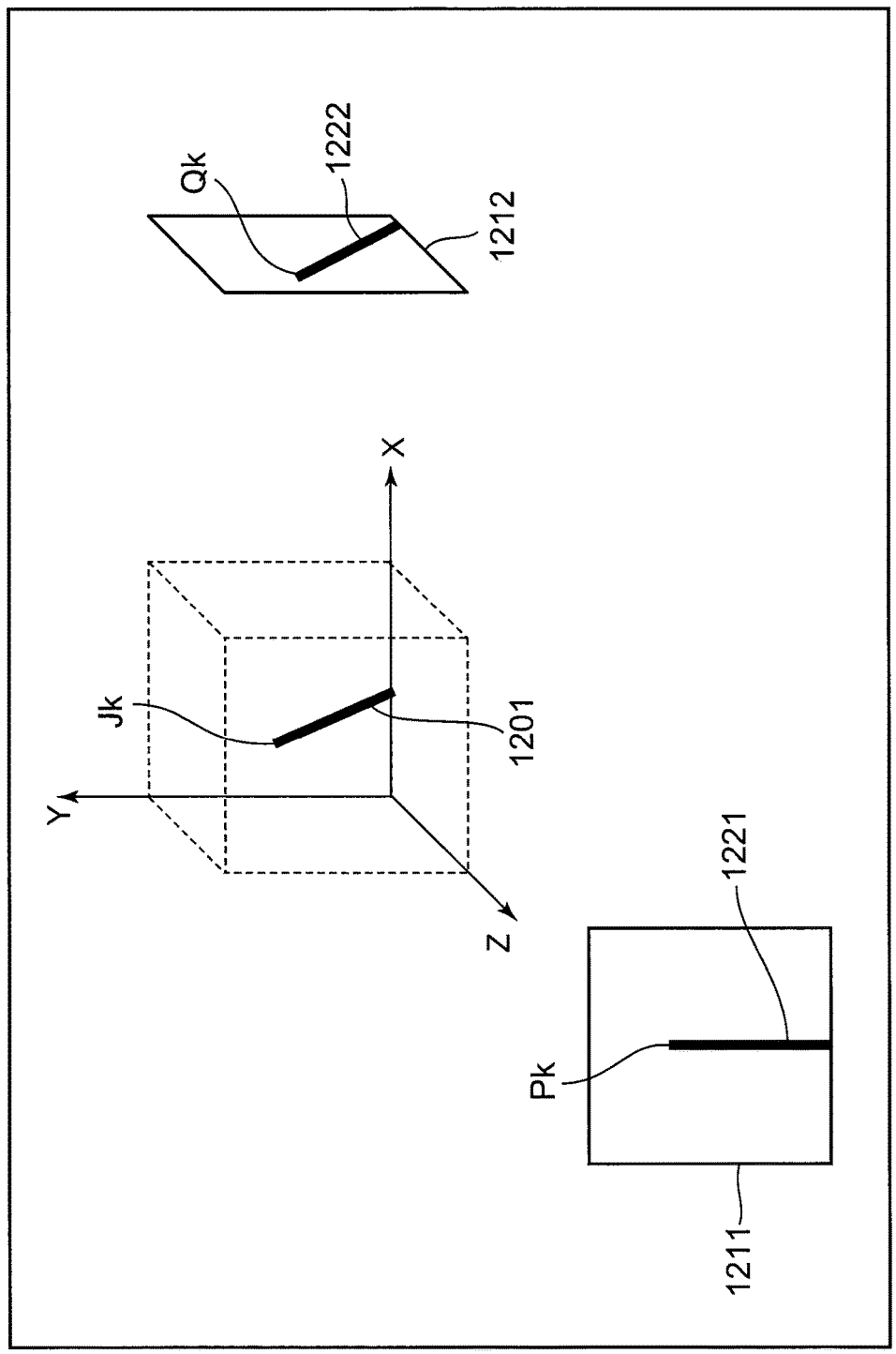
FIG. 35 is an exemplary view of a 3D blood vessel according to the second embodiment.
Figure 36:
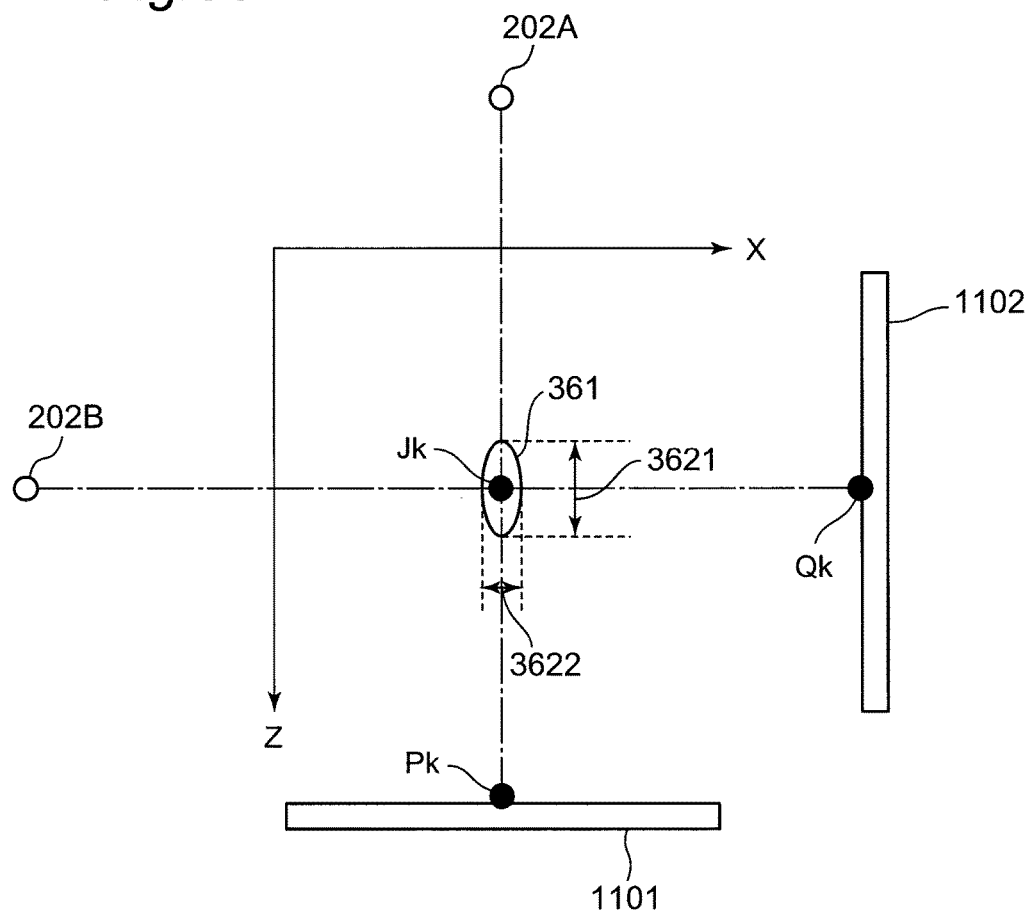
FIG. 36 is a view of a section of the blood vessel according to the second embodiment.

A reason for such a difference in brightness is relevant to a sectional shape of the blood vessel 1201. This relevance will be described below with reference to FIGS. 35 and 36. FIG. 35 is an exemplary view of the blood vessel 1201. An X-ray image 1211 is captured by the radiographing unit 101, and a blood vessel image 1221 is an image of the blood vessel 1201 on the X-ray image 1211. Similarly, an X-ray image 1212 is captured by the radiographing unit 102, and a blood vessel image 1222 is an image of the blood vessel 1201 on the X-ray image 1212. Reference signs Jk, Pk, and Qk indicate the 3D region Jk, the first image projection point Pk of the 3D region Jk, and the corresponding point Qk of the first image projection point Pk, respectively. FIG. 36 is a view of a plane (epipolar plane) including the 3D region Jk, the first image projection point Pk, and the corresponding point Qk, which is viewed from a +Y position toward a −Y position in FIG. 35. The blood vessel 1201 has a blood vessel section 361 in an elliptical shape as depicted in FIG. 36. (The blood vessel 1201 typically has an elliptical sectional shape except in a specific case.) The blood vessel 1201 has a thickness 3621 at a portion that an X-ray passes to reach the first image projection point Pk, and has a thickness 3622 at a portion that an X-ray passes to reach the second image projection point Qk. The thickness 3621 and the thickness 3622 are different from each other because the blood vessel 1201 has the elliptical sectional shape (not a circular shape). An X-ray passes a thicker blood vessel section to reach the first image projection point Pk, and the first image projection point Pk thus has brightness lower than the brightness of the corresponding point Qk (with a smaller brightness difference from the background). In this manner, brightness of the first image projection point Pk obtained by capturing the 3D point Jk on the blood vessel 1201 (or the corresponding point Qk) has a smaller value as an X-ray passes a thicker portion of the blood vessel 1201. The thickness of the portion of the blood vessel 1201 passed by an X-ray differs depending on the capture direction of the blood vessel 1201. The projection point has different brightnesses depending on the capture directions even though the identical 3D point Jk is projected.

The second embodiment of the present disclosure adopts absorption properties for mapping independent from such a difference in brightness caused by capture directions. Mapping according to absorption properties is performed effectively even at a single time. For further improvement in accuracy with fewer influences by noise and the like, the second embodiment adopts determination of a corresponding point by comparison between chronological absorption properties, not at the single time. (Mapping according to absorption properties at a single time will be described in a modification example.)

Absorption properties are compared in accordance with Equation 3 on difference summing in the second embodiment. When the absorption property of the second image projection point Qk and the absorption property of the corresponding point Qk change at the same degrees, the absorption properties are equal to each other in value at each time. When the absorption property evaluator 1709 in the mapping unit 107 calculates the sum of the absolute values of the differences in absorption property at respective times, the sum of the absolute values will be theoretically 0. The value of Equation 14 is regarded as an evaluation value in the second embodiment, and the mapping controller 1701 determines the second image projection region Qk_x having the minimum evaluation value as the corresponding region Qk of the first image projection region Pk.

Effects of Second Embodiment

The image region mapping device and the 3D model generating apparatus according to the present disclosure can determine a corresponding point in accordance with absorption properties in a case where the epipolar line L2 includes a plurality of candidate corresponding points Qk_n (n=1, 2, . . . , and N) of the first image projection point Pk.

Firstly, a corresponding region can be determined for each of the first image projection regions Pk of the blood vessel into which a contrast medium is injected. According to the technique of Non-Patent Literature 1, a blood vessel can be mapped only at an end point of a capture target region. In contrast, the image region mapping device and the 3D model generating apparatus according to the second embodiment of the present disclosure can map points in addition to the endpoint to restore a finer shape.

According to the present disclosure, the absorption property acquiring unit 1707 calculates a difference between a product of logarithms of the number of pixels in the projection region (the first image region Pk) and intensity of an X-ray emitted from the X-ray generator in the first radiographing unit and logarithm sums of intensity of X-rays acquired at the respective pixels in the projection region (the first image region Pk), and the absorption property evaluator 1709 acquires the sum of the differences as an evaluation value. Such an evaluation value for the corresponding point Qk of the first image projection point Pk is smaller (than evaluation values for the second image projection regions other than the corresponding point). The corresponding point can be thus determined in accordance with the evaluation values.

Secondly, the first image projection point Pk can be mapped even when the blood vessel 1201 has an elliptical sectional shape.

Figure 37:
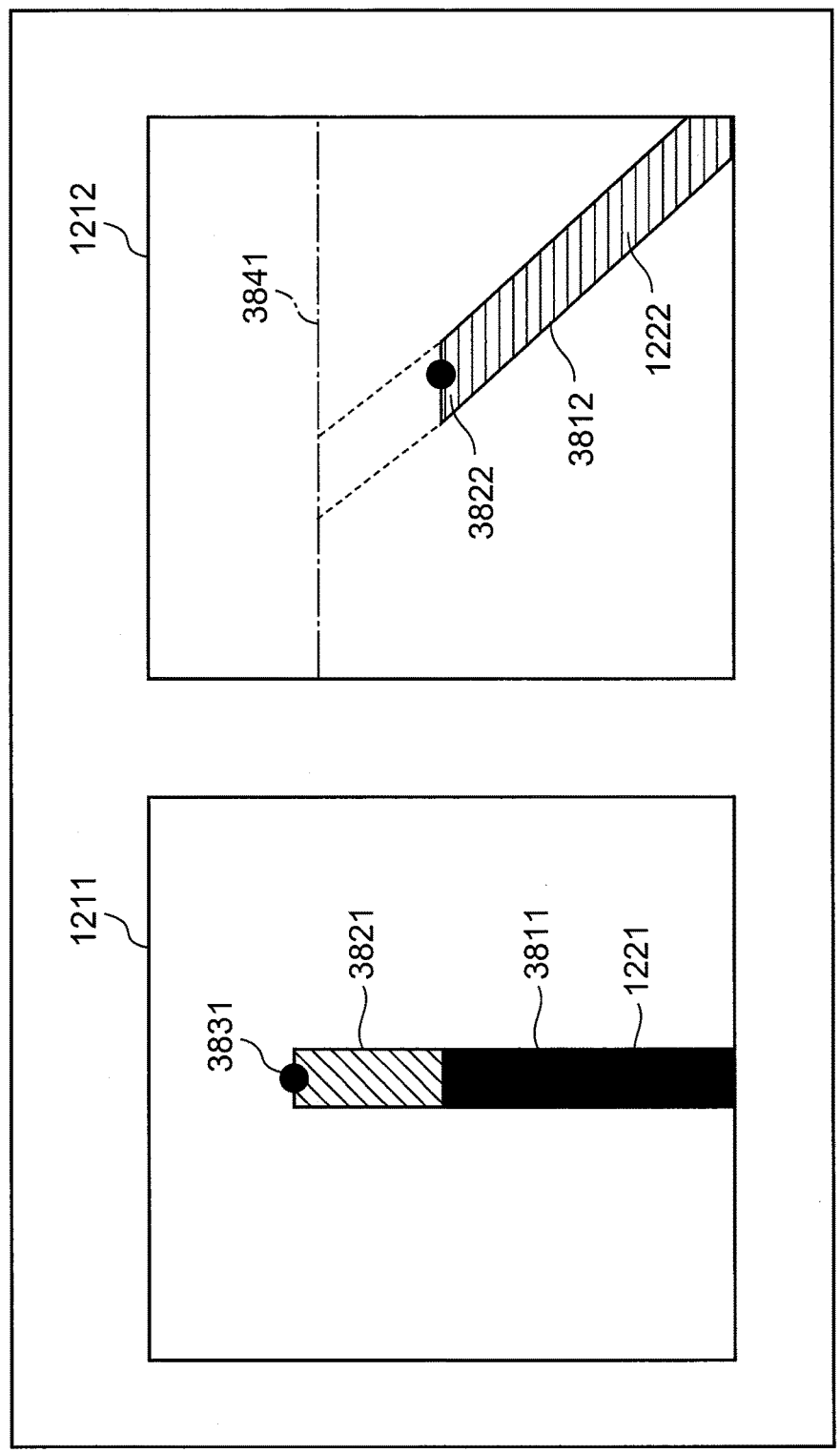
FIG. 37 is a view of X-ray images photographing the 3D blood vessels according to the second embodiment.
Figure 38:
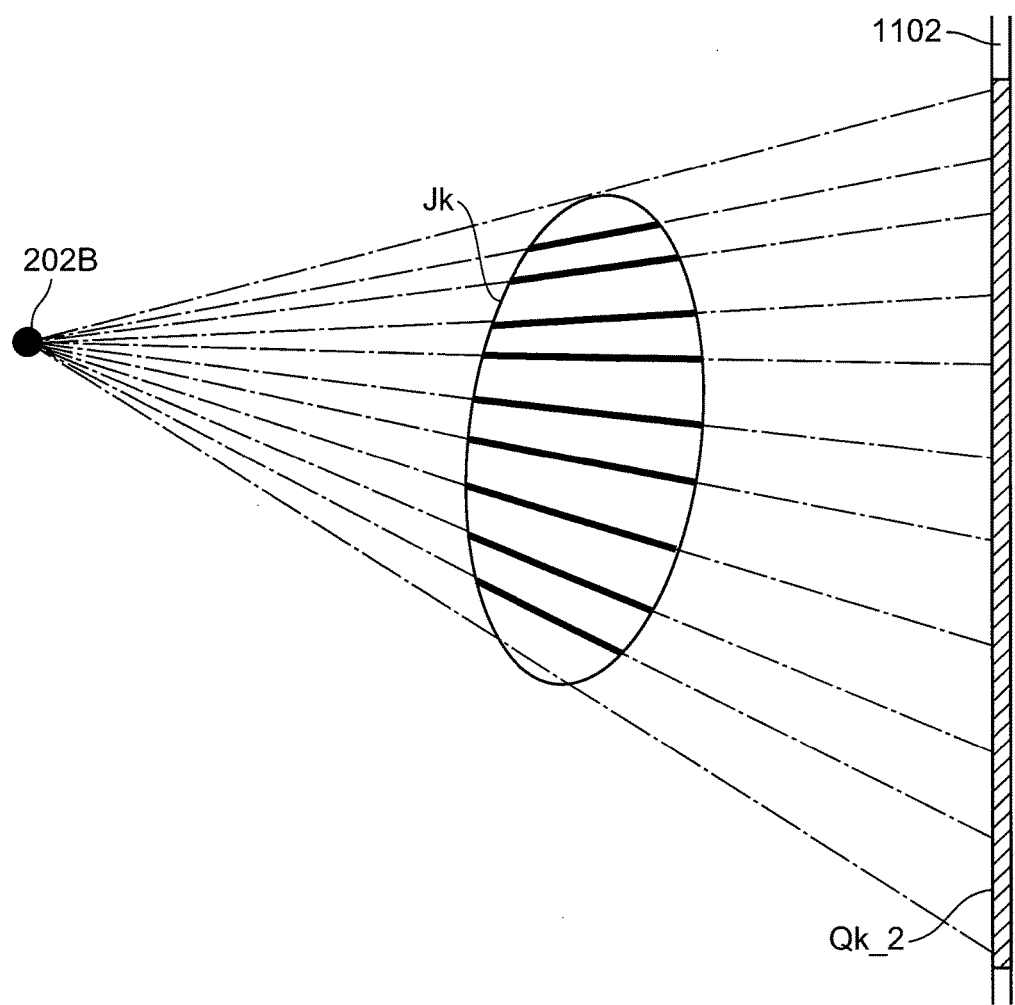
FIG. 38 is a view of an epipolar plane according to the modification example 2 of the second embodiment.

Two illustrations in FIG. 37 depict the enlarged X-ray images 1211 and 1212 in FIG. 35. The blood vessel image 1221 on the X-ray image 1211 has a dark portion 3811 (the portion with low brightness, in other words, the portion largely different in brightness from the background) and a bright portion 3821 (the portion with high brightness, in other words, the portion slightly different in brightness from the background). The bright portion 3821 actually has gradation in brightness, and is gradually brighter in the upward direction. The contrast medium injected into the blood vessel 1201 is mixed with peripheral blood, so that the contrast medium is gradually decreased in concentration toward the end. In other words, brightness is higher toward the end. A blood vessel end point 3831 is an end point of the blood vessel image 1221. A blood vessel portion captured as the dark portion 3811 on the X-ray image 1211 corresponds to a bright portion 3812 on the X-ray image 1212. This is because the X-ray images 1211 and 1212 are different from each other in brightness of the blood vessel images, as described earlier. A blood vessel portion captured as the bright portion 3821 on the X-ray image 1211 appears brighter on the X-ray image 1212 and cannot be extracted (the range surrounded with a dotted line in the right illustration in FIG. 37 cannot be extracted). The blood vessel image 1222 thus has an end point at the position denoted by reference sign 3822. The end point 3831 extracted on the X-ray image 1211 and the end point 3822 extracted on the X-ray image 1212 correspond to projection points of different 3D points. Any corresponding point is not located on an epipolar line 3841 for the end point 3831 and end points cannot be mapped in this case. It is assumed that there is only one blood vessel 1201 in this case. If an end point of a different blood vessel is located on the epipolar line 3841, the different blood vessel may be mapped erroneously. Absorption properties are compared between the first image projection point Pk and the second image projection region Qk_n in the present disclosure. Even when the first image projection point Pk and the corresponding point Qk are different from each other in brightness, comparison of absorption properties achieves accurate mapping. Even when the first image projection point Pk and the corresponding point Qx (x≠k) are equal to each other in brightness at a specific time, comparison of absorption properties achieves accurate mapping.

Described in the second embodiment is the configuration of comparison between the absorption properties λ_Pk_t (t=1, 2, . . . , and END) and the absorption properties λ_Qk_n_t at each time t. This configuration can be replaced with the configuration of comparison of absorption properties normalized so that the maximum absorption property is 1 and the minimum absorption property is 0. Such a configuration achieves comparison of absorption properties even in a case where there is an intensity difference between X-rays generated by the X-ray generators 202 in the radiographing units 101 and 102 or a detection property difference between the respective X-ray detectors 203.

The second embodiment refers to the case where injection of a contrast medium starts after the X-ray image acquiring unit 113 starts the process. Alternatively, the X-ray image acquiring unit 113 can start the process after injection of a contrast medium starts.

The second embodiment refers to the case where the capture target region acquiring unit 105 executes the process after the input IF 114 commands end of image capture. Alternatively, subsequent steps S1903 to S1907 can be executed every time the X-ray image acquiring unit 113 acquires an X-ray image. In such a configuration, an operating person (operator) can view the display unit 112 to check a 3D shape of the blood vessel 1201 also at timing when a contrast medium is expanding in the blood vessel 1201.

The second embodiment refers to the configuration in which the display screen generator 111 generates the second image projection region Qk_n having the best evaluation value out of the second image projection regions Qk_n (n=1, 2, . . . , and N) and the display unit 112 displays the generated second image projection region Qk_n. However, a corresponding point of the first image projection point Pk is not always captured. For example, any corresponding point is not captured when the 3D point Jk is located at a position not captured by the radiographing unit 102. In a case where the best evaluation value is worse than a predetermined threshold (where the minimum evaluation value out of the evaluation values for the second image projection regions is larger than a predetermined evaluation value in this case), the display unit 112 can be configured not to display the second image projection region Qk_n. There can be optionally provided a unit configured to input the predetermined threshold to the display unit 112. In this case, the display unit 112 displays only corresponding points that have evaluation values smaller than the predetermined threshold.

The second embodiment refers to the configuration in which the radiographing unit information storage 104 preliminarily holds the radiographing unit information including the translation vector T, the rotation vector R, and the internal parameters A1 and A2. Alternatively, the radiographing unit information storage 104 can be configured to acquire and hold such information when necessary from the positions of the X-ray generators 202 and the X-ray detectors 203 of the radiographing units 101 and 102.

The capture target region acquiring unit 105 according to the second embodiment acquires the region of the blood vessel 1201 into which a contrast medium is injected from the images 1_END and 2_END. Alternatively, the capture target region acquiring unit 105 can acquire the region into which a contrast medium is injected at each time and regard the sum of the acquired regions as a capture target region. In such a configuration, if there is a range not extracted as a capture target region at the time END and such a range can be extracted as a capture target region at a different time, the capture target region acquiring unit 105 can eventually extract a capture target region including the region. The absorption property evaluator 1709 according to the second embodiment compares absorption properties of the first image projection point Pk and the second image projection regions Qk_n and obtains the sum of the absorption property differences as the evaluation value. The absorption property evaluator 1709 can alternatively regard the maximum value of the absorption property differences as the evaluation value.

Modification Example 1 of Second Embodiment

The second embodiment refers to the configuration of comparison between the absorption properties of the chronological images captured by the radiographing unit 101 and the absorption properties of the chronological images captured by the radiographing unit 102 and determination of a corresponding region. This configuration can be replaced with the configuration according to the modification example 1 of the second embodiment, of comparison between an absorption property of a single image captured by the radiographing unit 101 and an absorption property of a single image captured by the radiographing unit 102 and determination of a corresponding region.

The difference between the modification example 1 of the second embodiment and the second embodiment in this case will be described below.

The X-ray image acquiring unit 113 acquires the image 1_0 from the radiographing unit 101 and the image 2_0 from the radiographing unit 102 at timing commanded by the input IF 114 and ends image acquisition.

The absorption property acquiring unit 1707 acquires only an absorption property $\lambda\_Pk\_0$ and absorption properties $\lambda\_Qk\_n\_0$ (n=1, 2, . . . , and N) and stores the acquired absorption properties in the absorption property storage 1708.

The subsequent processes similar to those according to the second embodiment are applied only to the absorption property $\lambda\_Pk\_0$ and the absorption properties $\lambda\_Qk\_n\_0$ (n=1, 2, . . . , and N) held by the absorption property storage 1708. Such a configuration achieves 3D reconfiguration of a blood vessel with a small number of images. Reconfiguration can be achieved even in a case where a blood vessel shifts due to pulsation or shift of a patient.

Modification Example 2 of Second Embodiment

Figure 39:
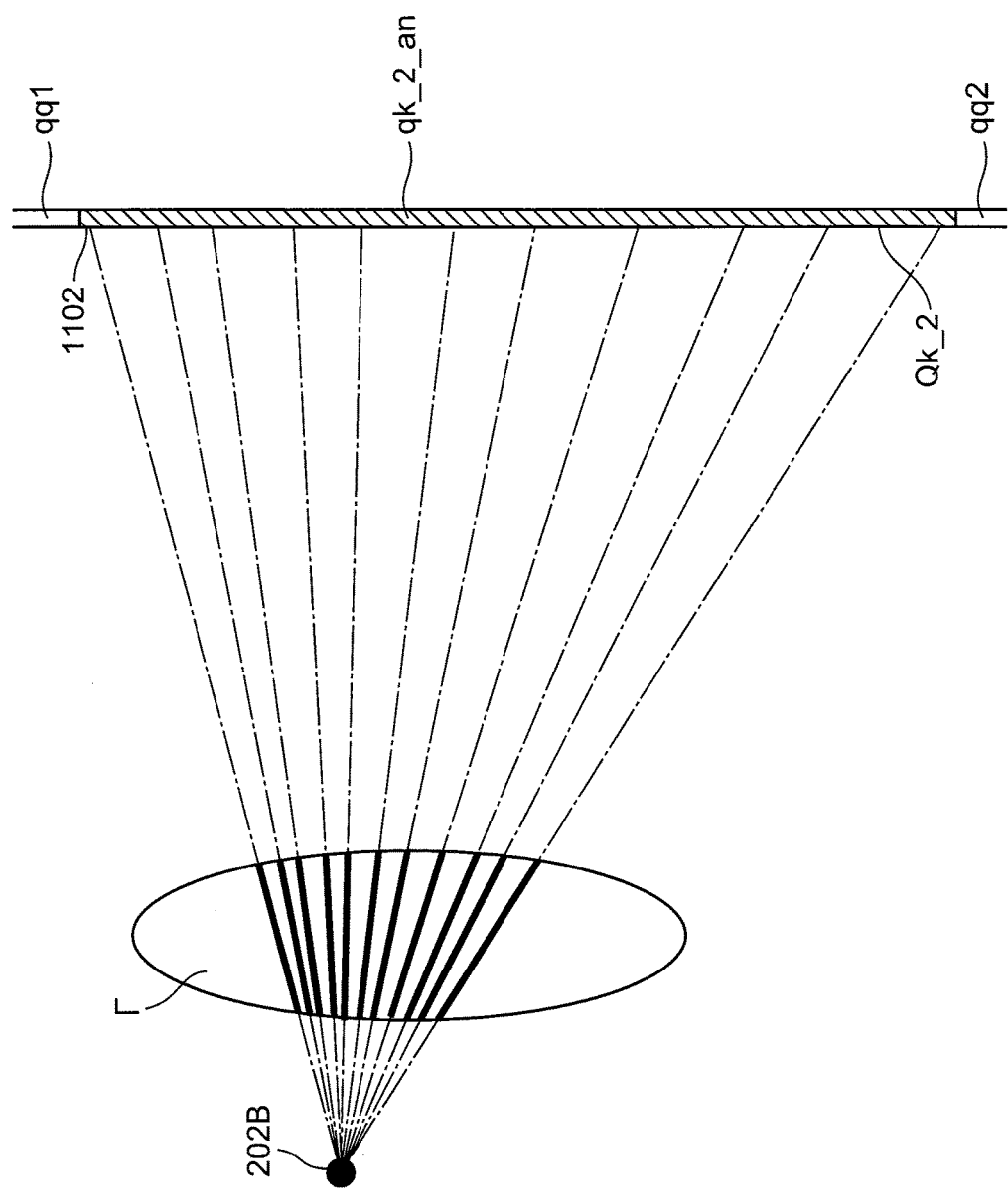
FIG. 39 is a view of an epipolar plane according to the modification example 2 of the second embodiment.
Figure 40:
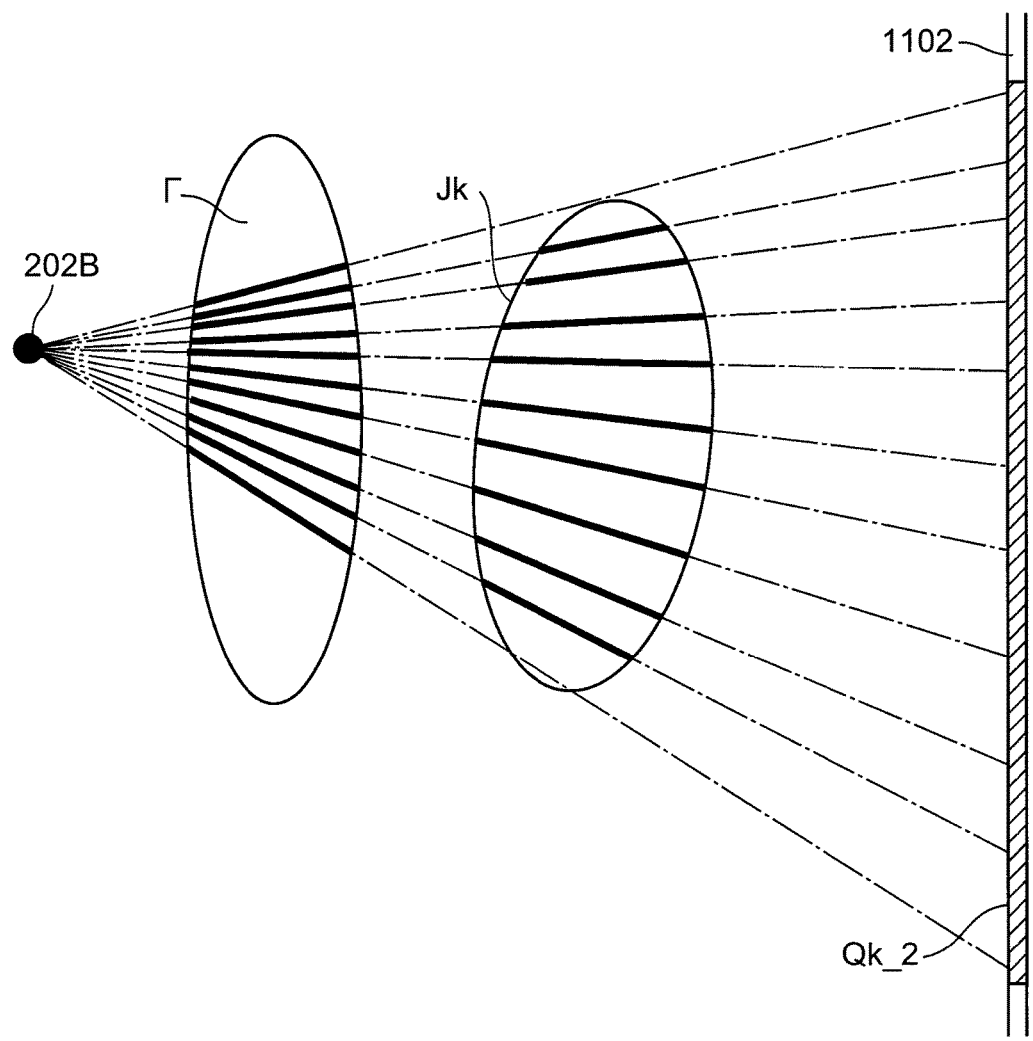
FIG. 40 is a view of an epipolar plane according to the modification example 2 of the second embodiment.

The second embodiment refers to the case where the epipolar plane includes only the blood vessel 1201. The modification example 2 of the second embodiment refers to a case where the epipolar plane includes an X-ray absorbing object in addition to the blood vessel. FIGS. 39 and 40 each depict an epipolar plane including a capture target T. FIG. 39 depicts a state before a contrast medium is injected whereas FIG. 40 depicts a state after a contrast medium is injected.

When intensity of the pixels pk_b composing the first image projection region Pk in FIG. 39 is denoted by I_b_0, a thickness of the capture target Γ passed by X-rays reaching the pixels pk_b is denoted by $d_\Gamma\_b$, and the capture target Γ has a linear attenuation coefficient $\mu_\Gamma$ [cm$^{-1}$], Equation 15 is obtained.

$$I\_b\_0 = I_0 \times e^{-\mu_\Gamma \cdot d_\Gamma\_b} \qquad \text{(Equation 15)}$$

When logarithms of the both members of the equation are obtained and the absorption property acquiring unit 1707 calculates the sum of b=1, 2, . . . , and B, Equation 16 is obtained.

$$\sum_{b=1}^{B} \log I\_b\_0 = B \log I_0 - \mu_\Gamma \sum_{b=1}^{B} d_\Gamma\_b \qquad \text{(Equation 16)}$$

When intensity of the pixels pk_b composing the first image projection region Pk in FIG. 40 is denoted by I_b_t, Equation 17 is obtained.

$$I\_b\_t = I_0 \times e^{-(\mu_\Gamma \cdot d_\Gamma\_b + \mu \cdot d)} \qquad \text{(Equation 17)}$$

When logarithms of the both members of the equation are obtained and the absorption property acquiring unit 1707 calculates the sum of b=1, 2, . . . , and B, Equation 18 is obtained.

$$\sum_{b=1}^{B} \log I\_b\_t = B \log I_0 - \mu_\Gamma \sum_{b=1}^{B} d_\Gamma\_b - \mu \sum_{b=1}^{B} d\_b \qquad \text{(Equation 18)}$$

The first and second terms of the right member of Equation 18 are replaced in accordance with Equation 16 to obtain Equation 19.

$$\sum_{b=1}^{B} \log I\_b\_t = \sum_{b=1}^{B} \log I\_b\_0 - \mu \sum_{b=1}^{B} d\_b \qquad \text{(Equation 19)}$$

Equation 20 is obtained by modifying Equation 19.

$$\mu \sum_{b=1}^{B} d\_b = \sum_{b=1}^{B} \log I\_b\_0 - \sum_{b=1}^{B} \log I\_b\_t \qquad \text{(Equation 20)}$$

The left member of Equation 20 describes a definition of an absorption property and clarifies that the absorption property acquiring unit 1707 can calculate an absorption property also in accordance with Equation 20. The absorption property acquiring unit 1707 calculates the first term of the right member to obtain the sum of logarithms of brightness of the points composing the first image projection region Pk at the time 0. The absorption property acquiring unit 1707 can similarly calculate an absorption property of the second image projection region Qk in accordance with Equation 21.

$$\mu \sum_{an=1}^{An} d\_an = \sum_{b=1}^{B} \log I\_an\_0 - \sum_{an=1}^{An} \log I\_an \qquad \text{(Equation 21)}$$

This modification example refers to the case where there is no contrast medium in the 3D region Jk at the time 0. The absorption property acquiring unit 1707 can calculate an amount of increase in absorption property from the time 0 in accordance with Equations 20 and 21 even in a case where there is a contrast medium at the time 0.

The absorption property acquiring unit 1707 according to the modification example 2 calculates a difference between a value (logarithm sums) obtained by adding logarithms of intensity of X-rays acquired at the respective pixels in the projection region (the first image region or each of the second image regions) at a first time and a value (logarithm sums) obtained by adding logarithms of intensity of X-rays acquired at the respective pixels in the projection region at a second time different from the first time, as the absorption property of the projection region (the first image region or each of the second image regions). With the apparatus according to the modification example 2, a blood vessel can be reconfigured even when an object causing a brightness difference such as a bone or the like is captured in an X-ray image.

Modification Example 3 of Second Embodiment

The absorption property according to the second embodiment is defined by Equations 12 and 13. The modification example 3 of the second embodiment has a different definition of an absorption property.

The both members of Equation 10 in the second embodiment are divided by the intensity $I_0$ to obtain Equation 22.

$$\frac{I\_b}{I_0} = e^{-\mu \cdot d\_b} \qquad \text{(Equation 22)}$$

Equation 22 is satisfied also when b=1, 2, . . . , and B. A product of the left members is equal to a product of the right members, and Equation 23 is thus obtained.

$$\prod_{b=1}^{B} \frac{I\_b}{I_0} = \prod_{b=1}^{B} e^{-\mu \cdot d\_b} = e^{-\mu \Sigma_{s=1}^{S} d\_b} \qquad \text{(Equation 23)}$$

Equation 24 is obtained by further modifying Equation 23. Reference sign $\pi$ denotes an operator indicating a product of respective elements.

$$\prod_{b=1}^{B} \frac{I\_b}{I_0} = e^{-\mu \Sigma_{b=1}^{B} d\_b} \qquad \text{(Equation 24)}$$

Equation 21 is also applicable to each of the pixels qk_n_an composing the second image projection region Qk_n. When intensity of the pixel qk_n_an is denoted by I_an and the thickness of the 3D region Jk passed by X-rays reaching the pixel qk_n_an is denoted by d_an, Equation 25 is obtained similarly.

$$\prod_{b=1}^{B} \frac{I\_an}{I_0} = e^{-\mu \Sigma_{b=1}^{An} d\_an} \qquad \text{(Equation 25)}$$

In Equation 24, $\Sigma d\_b$ denotes a sectional area of the 3D region Jk. When the second image projection region Qk_n is the corresponding point of the first image projection region Pk, $\Sigma d\_an$ in Equation 25 also denotes a sectional area of the 3D region Jx. Equations 24 and 25 have equal values in this case.

In the modification example 3, assume that the value of Equation 24 is the absorption property $\lambda\_pk$ whereas the value of Equation 25 is the absorption property $\lambda\_qk\_n$.

The absorption property acquiring unit 1707 calculates the absorption property $\lambda\_pk$ as a product of values obtained by dividing brightness I_b in the respective pixels pk_b (b=1, 2, . . . , and B) in the first image projection region Pk by the intensity $I_0$.

The absorption property acquiring unit 1707 according to the modification example 3 calculates a value obtained by dividing a product of intensities of X-rays acquired at the respective pixels in the projection region (the first image region or each of the second image regions) by a value obtained by multiplying intensity of an X-ray generated by the first or second X-ray generator and the number of pixels in the projection region, as the absorption property of the projection region (the first image region or each of the second image regions).

Modification Example 4 of Second Embodiment

The modification example 4 of the second embodiment refers to a case similar to that of the modification example 2, where the epipolar plane includes an X-ray absorbing object in addition to the blood vessel.

When intensity of the pixels pk_b composing the first image projection region Pk in FIG. 39 is denoted by I_b_0, a thickness of the capture target $\Gamma$ passed by X-rays reaching the pixels pk_b is denoted by $d_\Gamma\_b$, and the capture target $\Gamma$ has a linear attenuation coefficient $\mu_\Gamma$ [cm$^{-1}$], Equation 26 is obtained.

$$\frac{I\_b\_0}{I_0} = e^{-\mu_\Gamma \cdot d_\Gamma\_b} \qquad \text{(Equation 26)}$$

Equation 26 is satisfied when b=1, 2, . . . , and B. The absorption property acquiring unit 1707 calculates a product of the left members and a product of the right members to obtain Equation 27.

$$\prod_{b=1}^{B} \frac{I\_b\_0}{I_0} = e^{-\mu_\Gamma \Sigma_{s=1}^{S} d_\Gamma\_b} \qquad \text{(Equation 27)}$$

When intensity of the pixels pk_b composing the first image projection region Pk in FIG. 40 is denoted by I_b_t, Equation 14 is obtained. The both members are divided by the intensity $I_0$. Equation 14 is satisfied when b=1, 2, . . . , and B. The absorption property acquiring unit 1707 calculates a product of the left members and a product of the right members, and thus, Equation 28 is obtained.

$$\prod_{b=1}^{B} \frac{I\_b\_t}{I_0} = e^{-\mu_\Gamma \Sigma_{s=1}^{S} d_{\Gamma\_b}} e^{-\mu \Sigma_{s=1}^{S} d\_b} \quad \text{(Equation 28)}$$

Equation 29 is obtained from Equations 27 and 28.

$$\prod_{b=1}^{B} \frac{I\_b\_t}{I\_b\_0} = e^{-\mu \Sigma_{s=1}^{S} d\_b} \quad \text{(Equation 29)}$$

The right member of Equation 29 describes a definition of an absorption property according to the modification example 2 and clarifies that the absorption property acquiring unit 1707 can calculate an absorption property also in accordance with Equation 29. The left member is calculated to obtain a product of "values obtained by dividing brightness at the time t by brightness at the time 0" at the points pk_b (b=1, 2, . . . , and B) composing the first image region Pk. More specifically, the absorption property acquiring unit can acquire, as an absorption property, an absorbed X-ray amount in the projection region (the first image region or each of the second image regions) from a value obtained by dividing a product of intensities of X-rays emitted from the first or second radiographing unit and acquired at the respective pixels in the projection region at a first predetermined time by a product of intensities of X-rays emitted from the first or second radiographing unit and acquired at the respective pixels in the projection region at a second predetermined time.

This modification example refers to the case where there is no contrast medium in the 3D region Jk at the time 0. The absorption property acquiring unit 1707 can calculate an amount of increase in absorption property from the time 0 in accordance with Equations 20 and 21 even in a case where there is a contrast medium at the time 0.

The absorption property acquiring unit 1707 according to the modification example 4 calculates, as an absorption property, a value obtained by dividing a product of intensity values of X-rays acquired at the respective pixels in the projection region at the first time by a product of intensity values of X-rays acquired at the respective pixels in the projection region at the second time. The apparatus according to the modification example 2 achieves reconfiguration of a blood vessel even when an object causing a brightness difference is captured in an X-ray image of a bone or the like.

Modification Example 5 of Second Embodiment

The modification examples 2 and 4 refer to how the absorption property acquiring unit 1707 calculates an absorption property with reference to the image at the time 0 before a contrast medium is injected and the image at the time t after a contrast medium is injected, when the epipolar plane includes an X-ray absorbing object in addition to the blood vessel. The modification example 5 refers to how the absorption property acquiring unit 1707 calculates an absorption property with reference to a single image.

Figure 41:
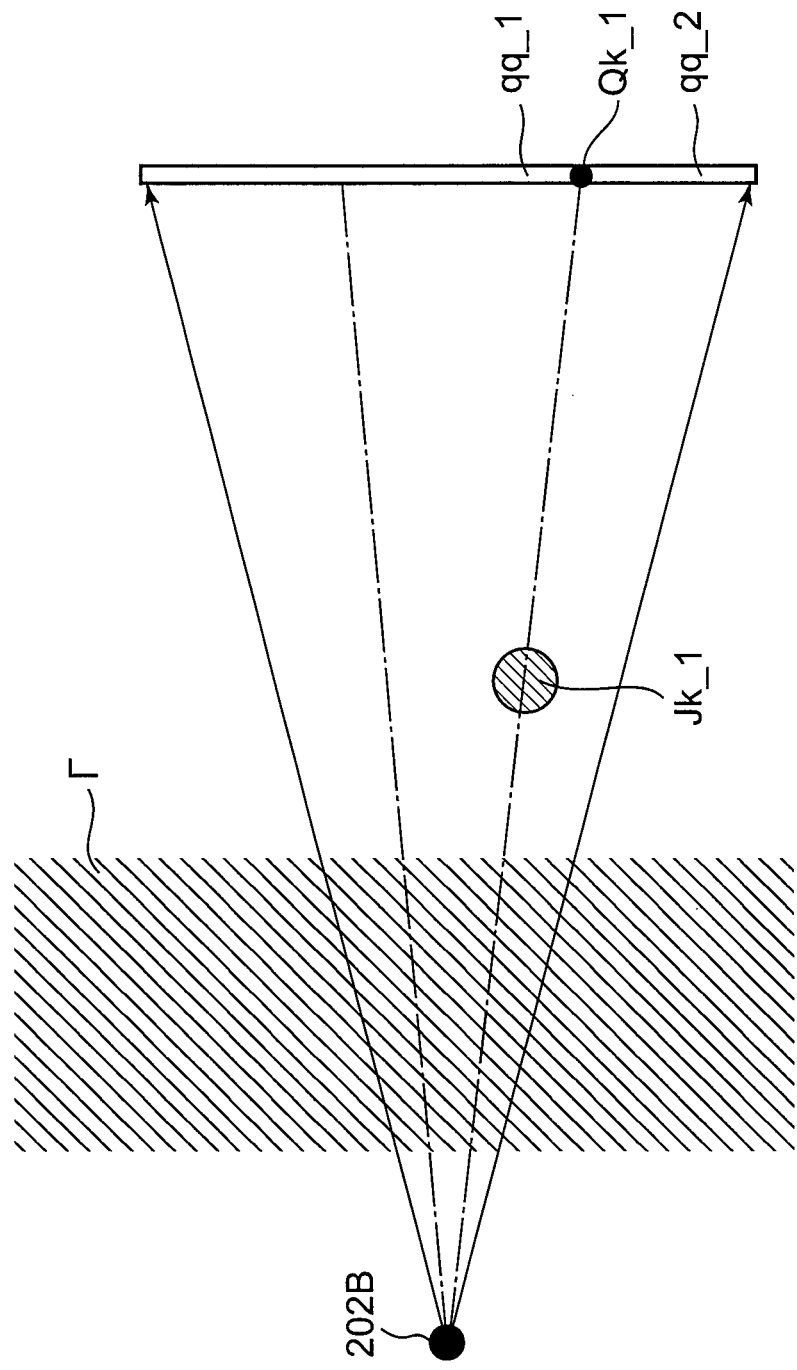
FIG. 41 is a view of an epipolar plane according to the modification example 2 of the second embodiment.

FIG. 40 depicts the capture target $\Gamma$ and the 3D region Jk as a region of the blood vessel 1201 in similar sizes. Actually, as depicted in FIG. 41, the 3D region Jk as the region of the blood vessel 1201 is quite small whereas the region of the capture target $\Gamma$ such as an organ is quite large. Points qq1 and qq2 in FIG. 41 are distant by, for example, five pixels or the like from the second image projection region Qk_2. X-rays reaching the points qq1 and qq2 transmit substantially same positions of the capture target r and thus have substantially equal brightness. When there is no contrast medium in the 3D region Jk_1, points in the second image region Qk_1 have brightness substantially equal to the brightness of the points qq1 and qq2. The absorption property acquiring unit 1707 calculates an absorption property with the brightness of the point qq1 (or the brightness of the point qq2, or average brightness of the points qq1 and qq2) being assumed as an approximate value of I_an_0 (an=1, 2, . . . , and An) in Equation 17. Similarly in Equations 16, 24, and 25, brightness of a point around the blood vessel is assumed as an approximate value of I_an_0 (an=1, 2, . . . , and An) or I_bn_0 (bn=1, 2, . . . , and Bn).

The absorption property acquiring unit 1707 can calculate an absorption property with reference to a single image in such a configuration.

Third Embodiment

A shape restoring apparatus 1C according to the third embodiment restores shapes of a plurality of blood vessels 1201 that overlap each other and appear like a single blood vessel on an image captured by the radiographing unit 101 (or 102).

When the intensity of each of the pixels pk_b composing the first image projection region Pk in FIG. 39 is denoted by I_b_0, the thickness of the capture target $\Gamma$ passed by X-rays reaching the pixels pk_b is denoted by $d_{\Gamma\_b}$, and the capture target $\Gamma$ has the linear attenuation coefficient $\mu_\Gamma$ [cm$^{-1}$], Equation 11 already described is satisfied.

Figure 42:
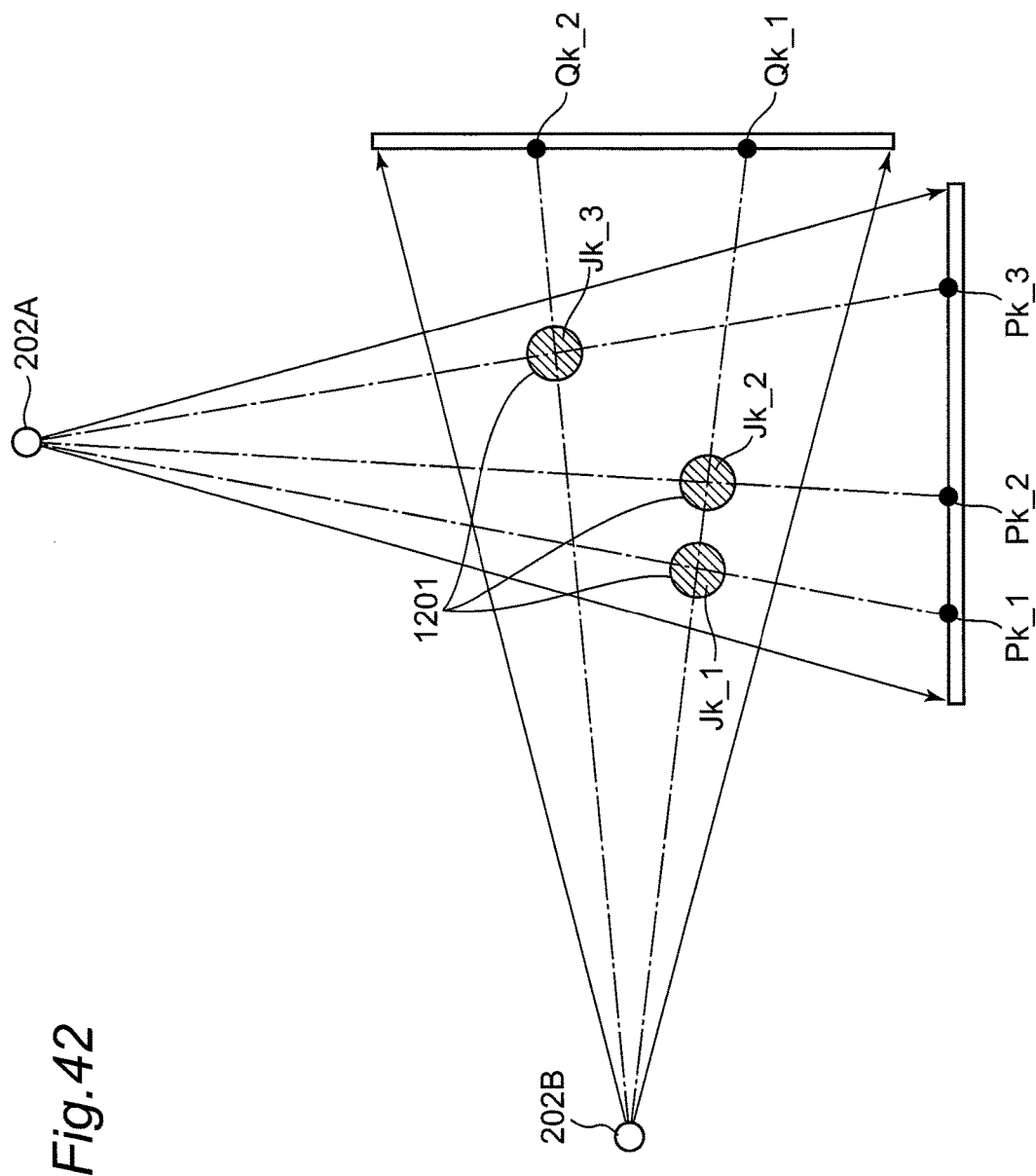
FIG. 42 is a view of an epipolar plane according to a third embodiment.

FIG. 42 depicts an epipolar section in a case where two blood vessels 1201 overlap each other on an image captured by the radiographing unit 102. An X-ray generated by the X-ray generator 202B in the radiographing unit 102 and having passed a 3D point Jk_1 of a first one of the blood vessels 1201 further passes a 3D point Jk_2 of a second one of the blood vessels 1201 and reaches a corresponding point Qk_1. An X-ray generated by the X-ray generator 202B in the radiographing unit 102 and having passed a 3D point Jk_3 reaches a corresponding point Qk_2. An X-ray generated by the X-ray generator 202A in the radiographing unit 101 and having passed the 3D point Jk_1 is projected at a first image projection point Pk_1 on the captured image. An X-ray generated by the X-ray generator 202A and having passed the 3D point Jk_2 is projected at a first image projection point Pk_2 on the captured image. An X-ray generated by the X-ray generator 202A in the radiographing unit 101 and having passed the 3D point Jk_3 is projected at a first image projection point Pk_3 on the captured image.

Figure 43:
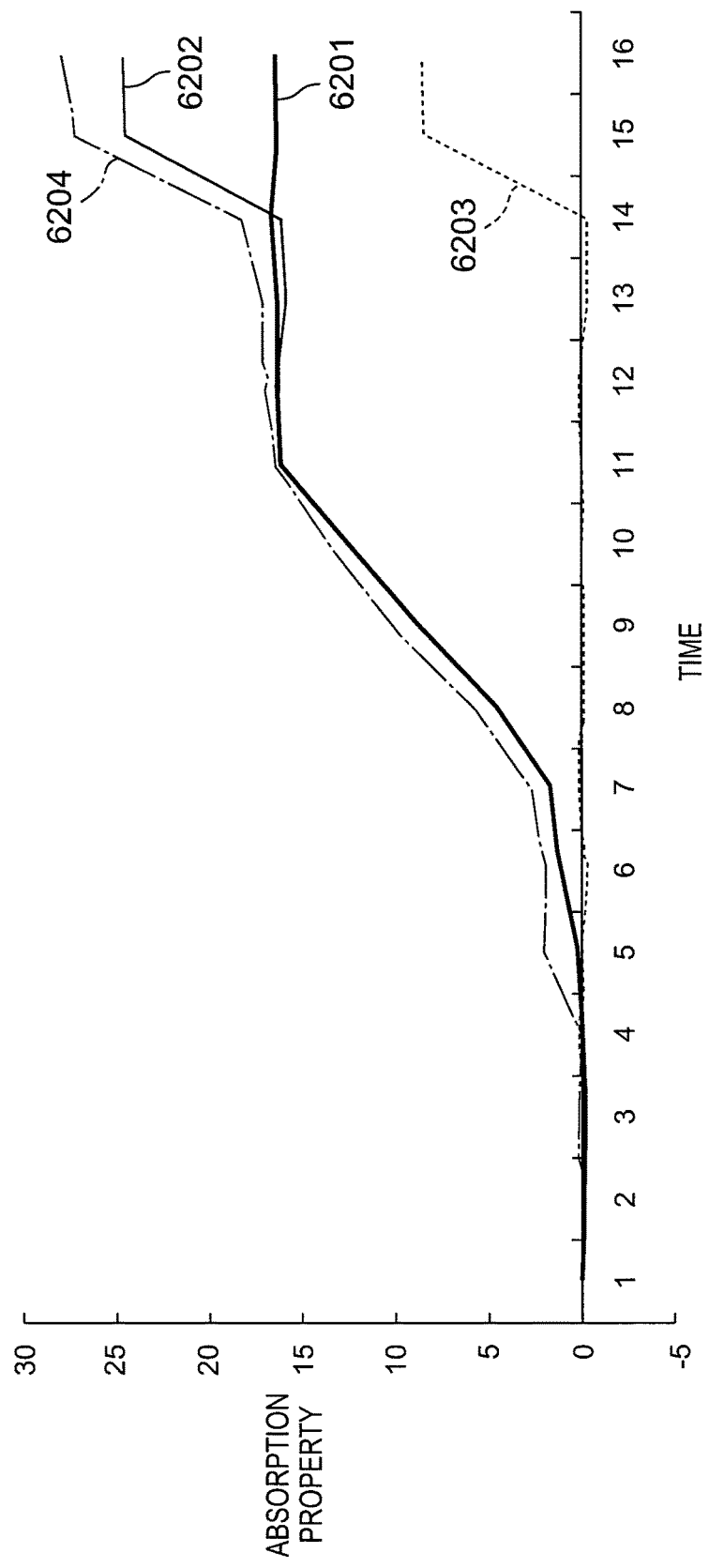
FIG. 43 is a graph indicating absorption properties of first image projection points Pk_1 to Pk_3 and second image projection regions Qk_1 and Qk_2 according to the third embodiment.
Figure 44:
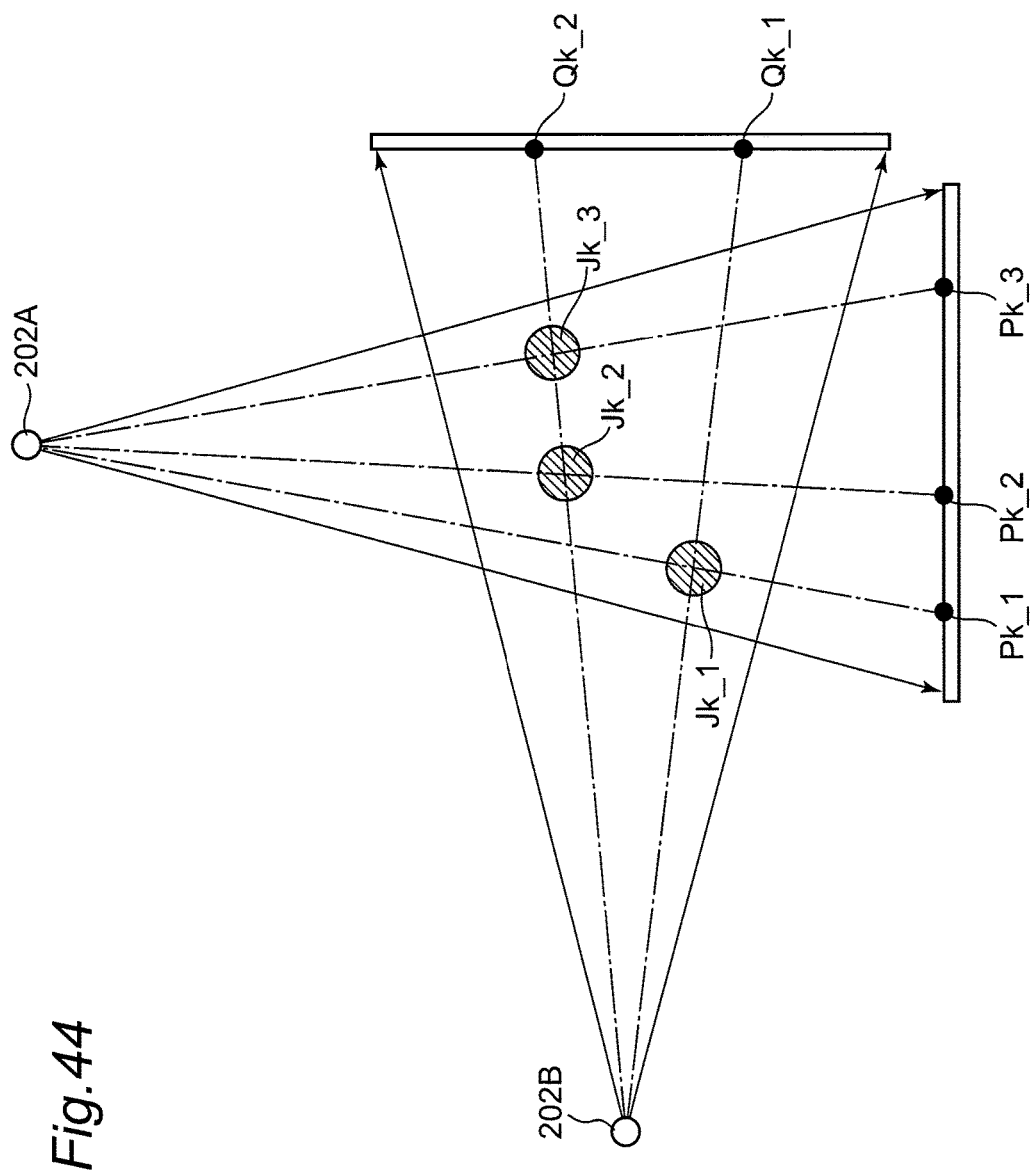
FIG. 44 is a view of an epipolar plane according to the third embodiment.
Figure 45:
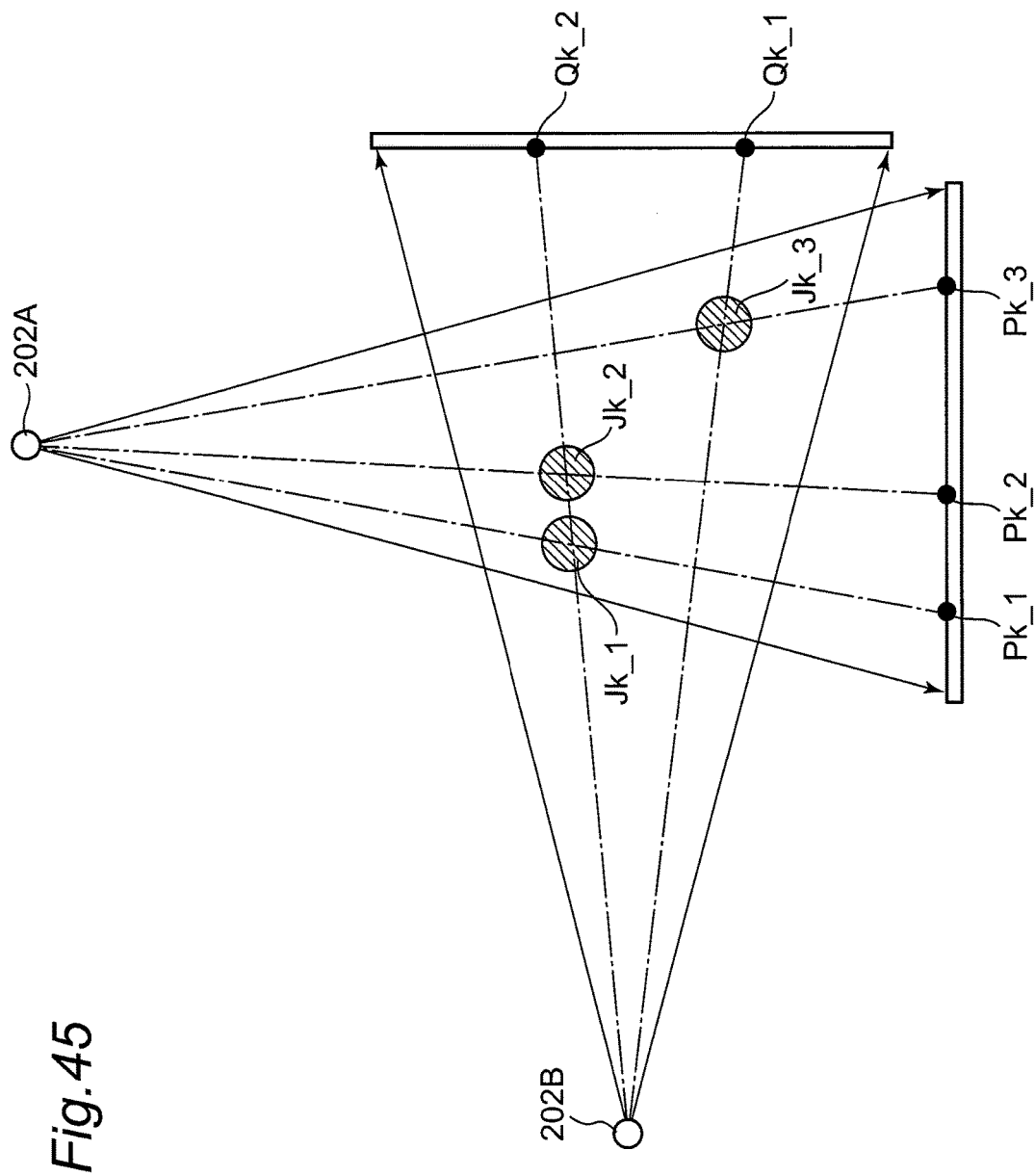
FIG. 45 is a view of an epipolar plane according to the third embodiment.
Figure 46:
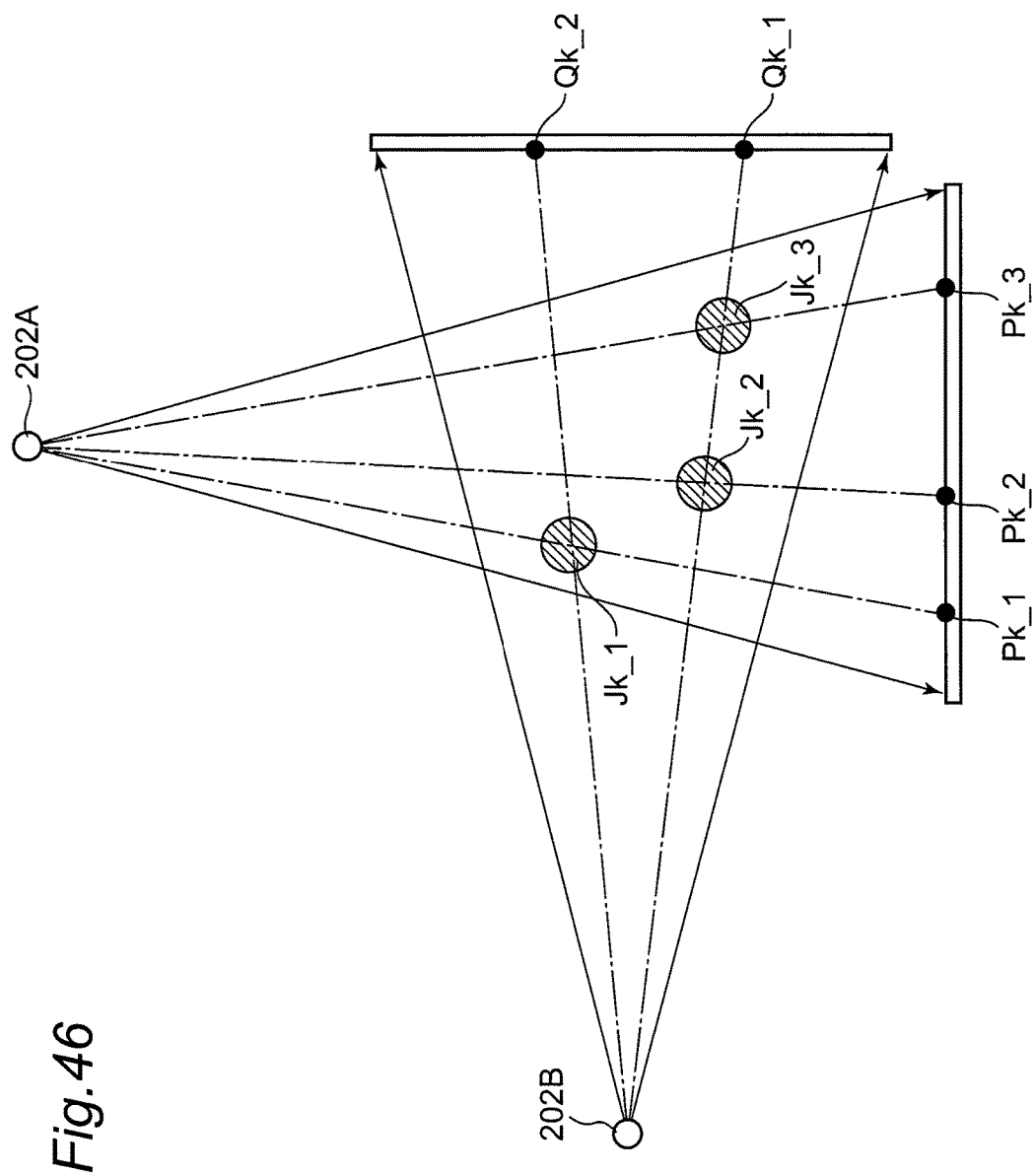
FIG. 46 is a view of an epipolar plane according to the third embodiment.
Figure 47:
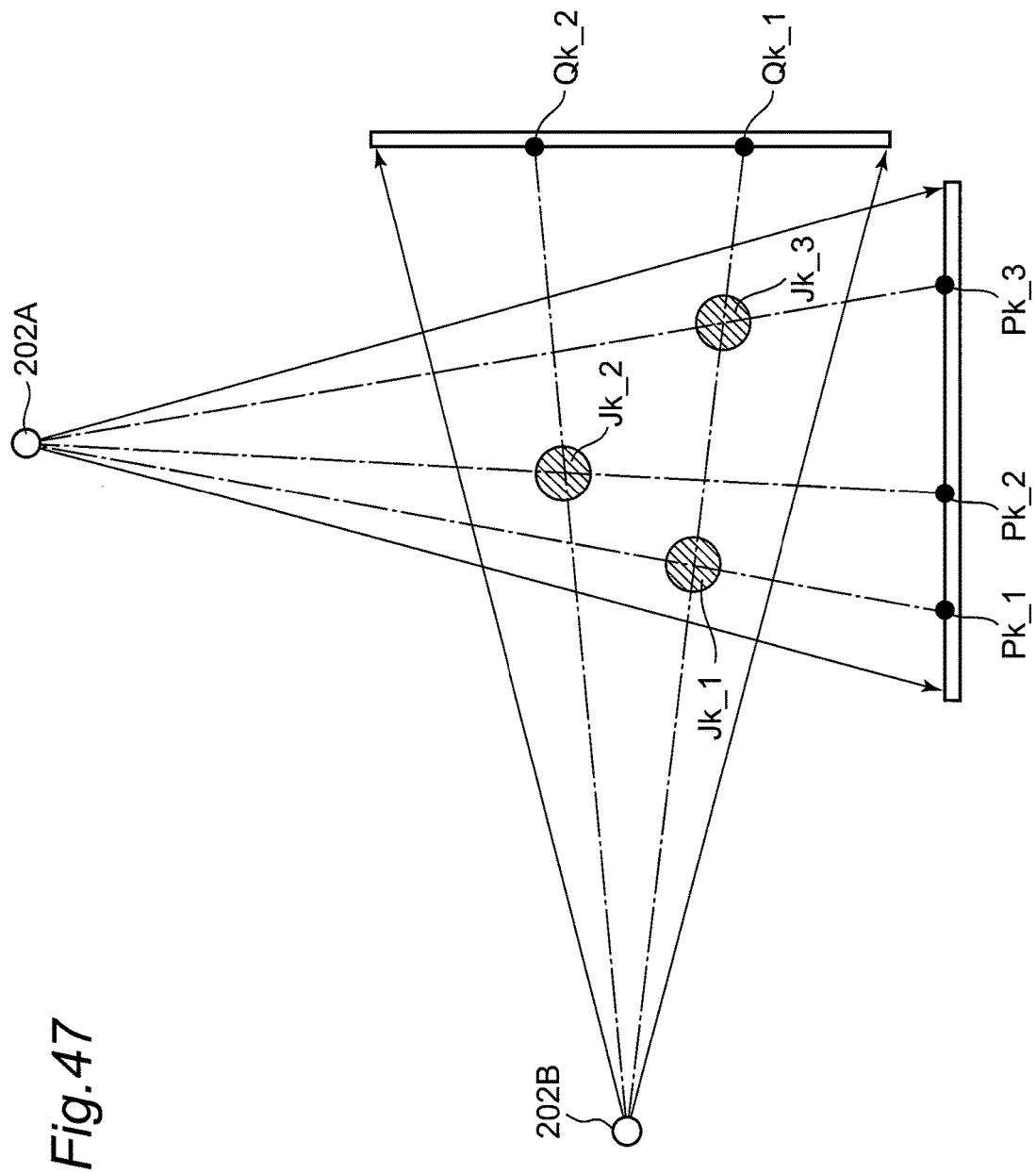
FIG. 47 is a view of an epipolar plane according to the third embodiment.
Figure 48:
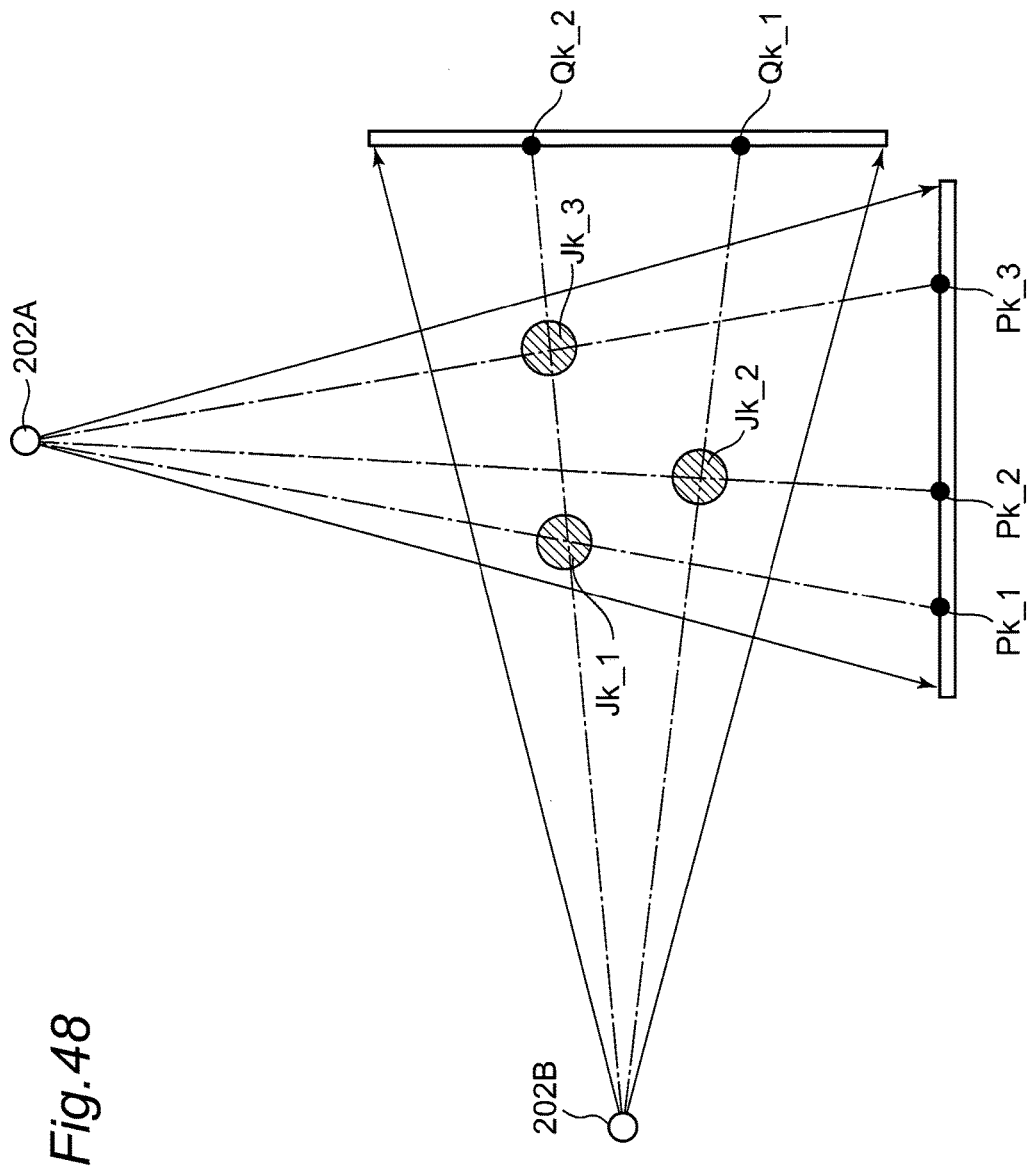
FIG. 48 is a view of an epipolar plane according to the third embodiment.

FIG. 43 is a graph indicating absorption properties of the first image projection regions Pk_1 and Pk_2 and the corresponding point Qk_1 in FIG. 42. In FIG. 43, a thick line 6201 indicates the absorption property of the first image projection region Pk_1, a dotted line 6203 indicates the absorption property of the first image projection region Pk_2, and a solid line 6202 indicates the brightness change of the corresponding point Qk_1. The blood vessels 1201 overlap each other, so that the absorption property of the corresponding point Qk_1 and the absorption property of the first image projection region Pk_1 are increased and decreased at different degrees. Furthermore, the absorption property of the corresponding point Qk_1 and the absorption property of the first image projection region Pk_2 are increased and decreased at different degrees.

However, a dashed line 6204 indicating an absorption property as the sum of the absorption property of the first image projection region Pk_1 and the absorption property of the first image projection region Pk_2 and the solid line 6202 indicating the absorption property of the second image projection region Qk_1 match each other.

The shape restoring apparatus 1C according to the third embodiment causes the absorption property evaluator 1709 to compare the absorption property as the total absorption properties of the plurality of first image projection regions and the absorption property of the second image projection region to perform mapping. In the case of FIG. 42, the absorption property evaluator 1709 compares the total absorption properties of the first image projection regions Pk_1 and Pk_2 and the absorption property of the corresponding point Qk_1. In FIG. 43, the dashed line 6204 indicates the sum of the absorption property of the first image projection region Pk_1 and the absorption property of the first image projection region Pk_2. The dashed line 6204 are increased and decreased at a degree similar to that of the solid line 6202.

For simplification in the following description, a case where the absorption property evaluator 1709 compares total absorption properties of first image projection regions Pk_x and Pk_y and an absorption property of a second image projection region Qk_z will be expressed as comparing [{x, y}, {z}] as a group.

The blood vessels 1201 depicted in FIG. 42 are projected at the first image projection regions Pk_1 to Pk_3 on an image captured by the radiographing unit 101 and are projected at the second image projection regions Qk_1 and Qk_2 on an image captured by the radiographing unit 102. In cases other than the case of FIG. 42, there may be a blood vessel that is projected at the same position as that of FIG. 42. More specifically, also when the 3D points Jk_1 to Jk_3 are located at the positions indicated in FIGS. 44 to 48, the first image projection regions and the second image projection regions appear at similar positions. (Although there may be specific other locations in actual cases, such cases will not be considered in the present embodiment.) The shape restoring apparatus 1C can extract a set of corresponding points of projection points of the blood vessel to be restored in shape from these blood vessels, and accurately restore the shape of the blood vessel.

Configuration According to Third Embodiment

Figure 49:
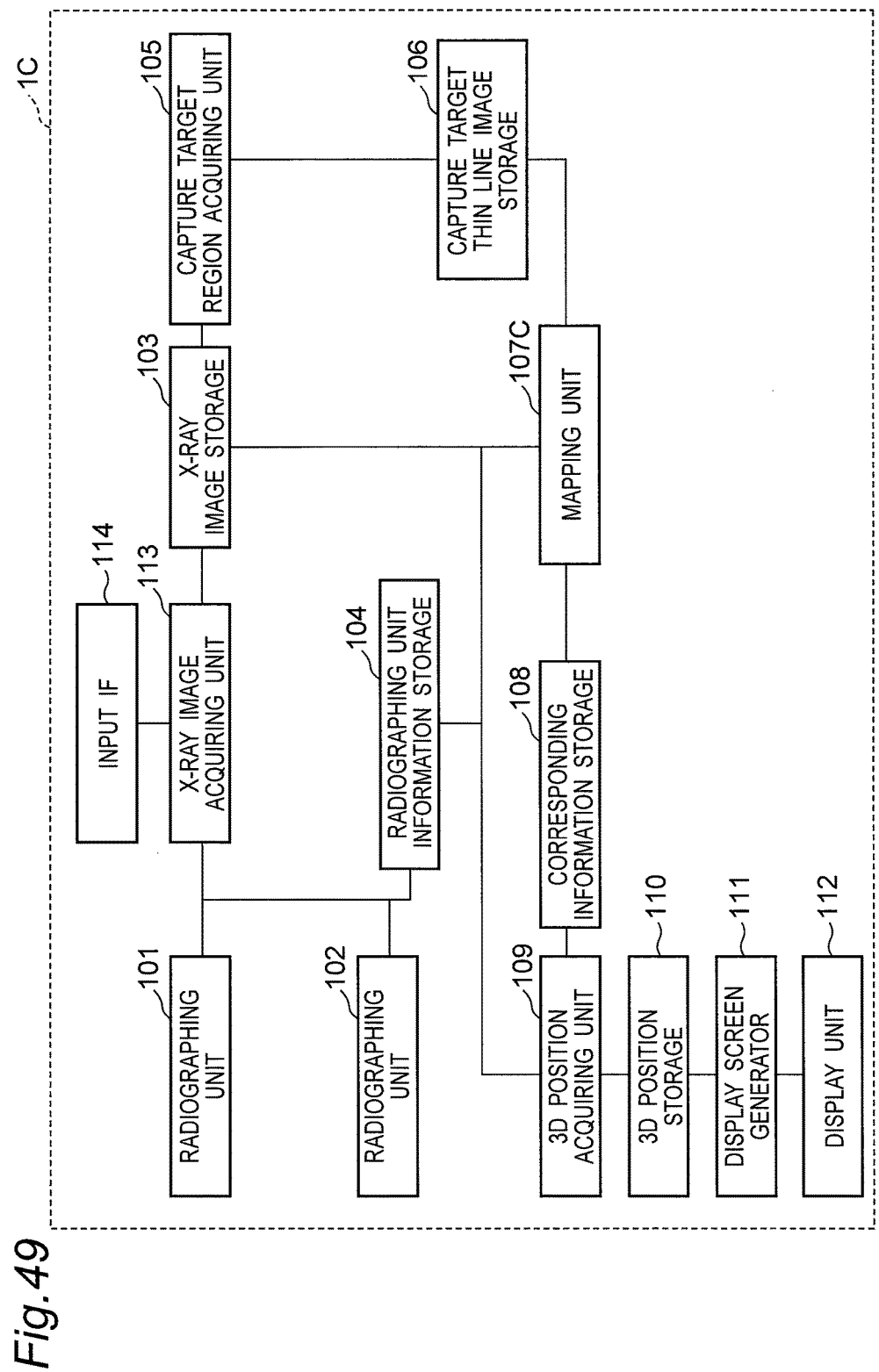
FIG. 49 is a view of the configuration of a shape restoring apparatus according to the third embodiment.
Figure 50:
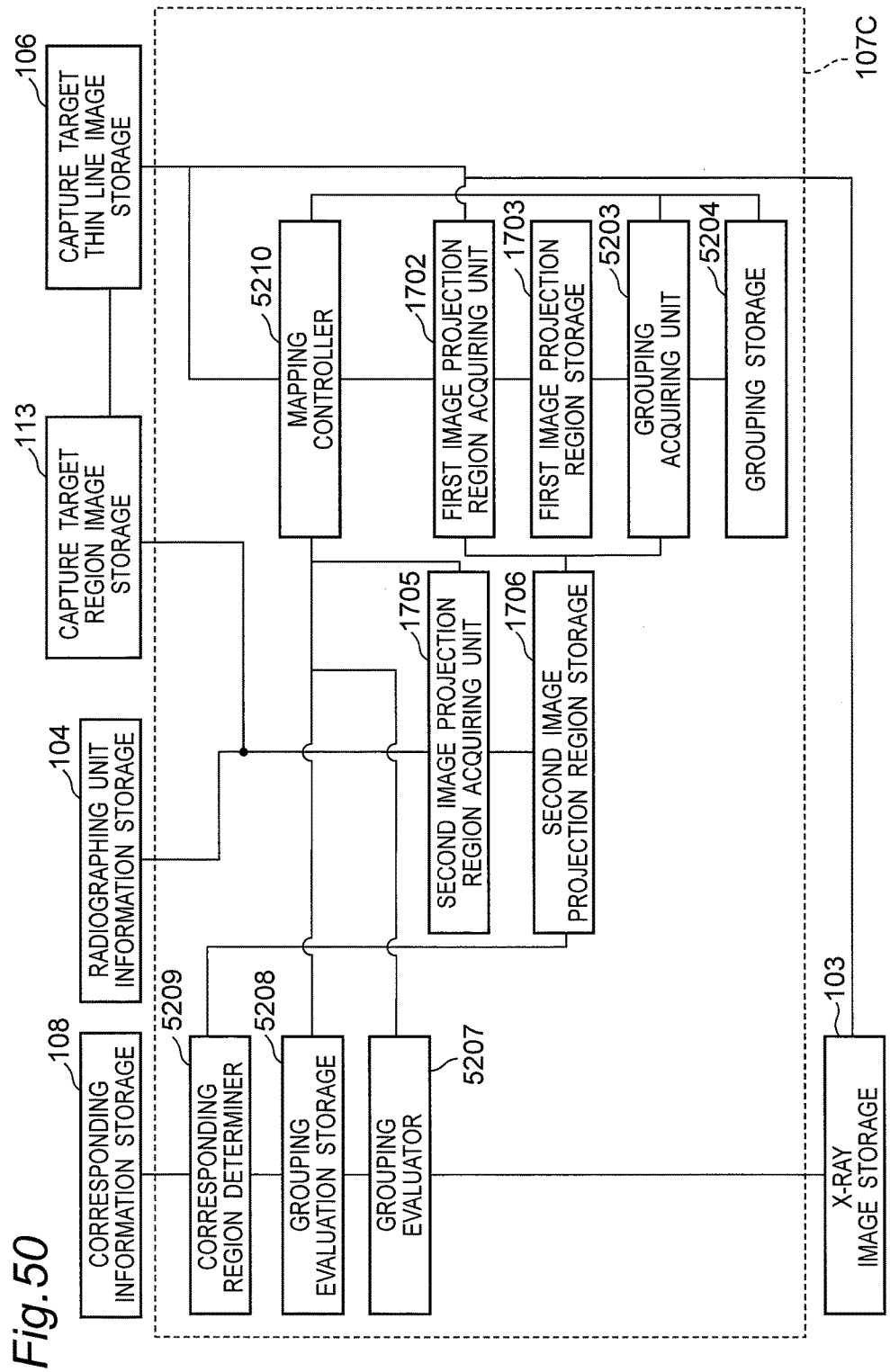
FIG. 50 is a view of the configuration of a mapping unit according to the third embodiment.

FIG. 49 is a view of the configuration of the shape restoring apparatus 1C according to the third embodiment. A mapping unit 107C replaces the mapping unit 107 according to the second embodiment. FIG. 50 is a view of the configuration of the mapping unit 107C.

The mapping unit 107C includes the second image projection region acquiring unit 1705, the second image projection region storage 1706, a first image projection region acquiring unit 1702, a first image projection region storage 1703, a grouping acquiring unit 5203, a grouping storage 5204, a grouping evaluator 5207, a grouping evaluation storage 5208, and a corresponding region determiner 5209.

The first image projection region acquiring unit 1702 acquires a position of each of first image projection regions Pk_m (m=1, 2, . . . , and M) of an intersection line (epipolar line) between the epipolar plane including the first image projection point Pk on the first capture target thin line image 1101T held by the capture target thin line image storage 106 and the second capture target thin line image 1102T, and stores the acquired positions in the first image projection region storage 1703. A first image projection point Pk_0 is assumed to be the same as the first image projection point Pk.

A specific method will be described below. A parameter l1 of the epipolar line L1 is initially calculated in accordance with Equation 30.

$$l1 = F^T m \quad \text{(Equation 30)}$$

In Equation 30, F denotes the determinant called the fundamental determinant that is calculated in accordance with Equation 6, and $F^T$ denotes the transpose of the fundamental determinant F. Furthermore, m denotes coordinates of an arbitrary projection point Qk_n acquired from the second image projection region storage 1706.

When the calculated parameter l1 of the epipolar line L1 is expressed as (a, b, c)T, the epipolar line L1 satisfies ax+by+c=0. Coordinates of an intersection point between the calculated epipolar line L1 and the first capture target thin line image 1101T are acquired similarly to the case with the second image projection region acquiring unit 1705, and the method thereof will not be described repeatedly.

The first image projection region storage 1703 holds coordinates of the first image projection regions Pk_m (m=1, 2, . . . , and M) acquired by the first image projection region acquiring unit 1702. In the following description, respective pixels composing the first image projection regions Pk_m will be denoted by pk_b_bm (bm=1, 2, . . . , and Bm; where Bm is the number of pixels composing the first image projection regions Pk_m).

The grouping acquiring unit 5203 generates grouping for the first image projection regions Pk_m (m=1, 2, . . . , and M) and the second image projection regions Qk_n (n=1, 2, . . . , and N). In an exemplary case where m=3 and n=2, six groupings are generated as indicated in FIG. 51. Grouping numbers (n=1, 2, . . . , and N), grouping results, and the numbers of the figures depicting corresponding epipolar sections are indicated in first, second, and third rows in FIG. 51

Figure 52:
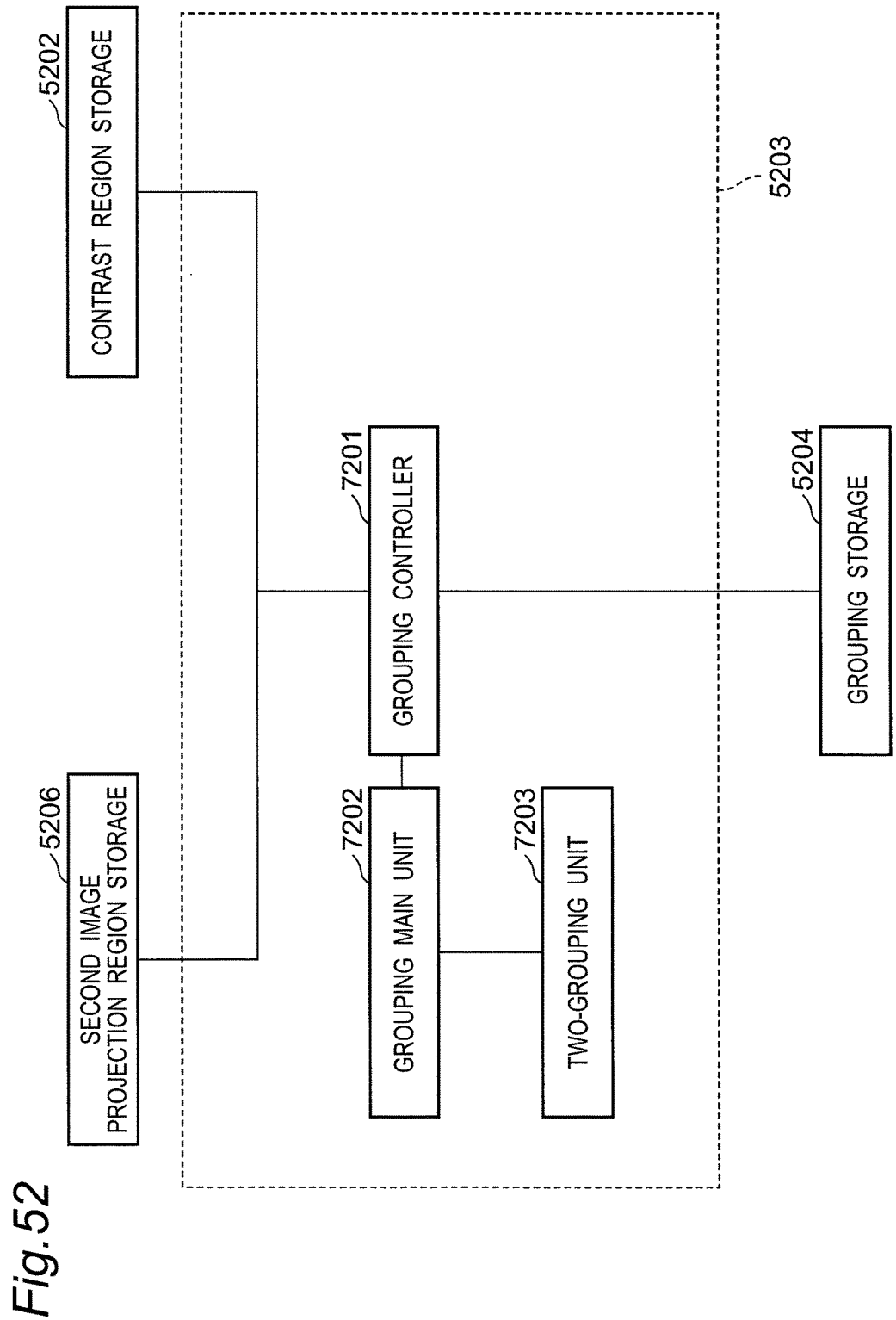
FIG. 52 is a view of the configuration of the grouping acquiring unit according to the third embodiment.

FIG. 52 is a view of the configuration of the grouping acquiring unit 5203. The grouping acquiring unit 5203 includes a grouping controller 7201, a grouping main unit 7202, and a two-grouping unit 7203.

The two-grouping unit 7203 generates a set of two-grouping for a group designated by the grouping main unit 7202, and transmits the set to the grouping main unit 7202.

A specific exemplary case of two-grouping when the grouping main unit 7202 transmits a group G={{F1, F2, F3}, {S1, S2}} to the two-grouping unit 7203 will be described below. FIG. 53 is a chart of sets for two-grouping (into a group G0 and a group G1). The chart in FIG. 53 has one set in each row. Each row includes a numerical value indicating to which group each element in a mass belongs. The value "0" indicates assignment to the group G0 whereas the value "1" indicates assignment to the group G1. In the set in the first row, an identifier S2 is assigned to the group G1 and other identifiers F1 to S1 are assigned to the group G0, for example. As indicated in FIG. 53, the group to which a first element in a mass G is assigned is called the group G0.

The number of grouping sets is 2^(N−1)−1 when the total number of elements is N, and generated are sets of the numbers from 1 to 2^(N−1)−1. An operator "^" indicates exponentiation operation. In the chart in FIG. 53, a U-th column from the right end has a value (number) % (2^U).

FIG. 54 exemplifies indications of respective element groups by grouping into groups 0 and 1.

The grouping controller 7201 acquires a number M of first image projection regions held by the first image projection region storage 1703 and a number N of projection regions held by the second image projection region storage 1706, causes the grouping main unit 7202 to be described later to perform grouping with arguments of a first element group {1, 2, . . . , and M} and a second element group {1, 2, . . . , and N}, and stores the grouping acquired by the grouping main unit 7202 in the grouping storage 5204.

The grouping main unit 7202 groups a first element group F {F_1, F_2, . . . , and F_M} and a second element group S {S_1, S_2, . . . , and S_N} having been designated. The grouping main unit 7202 groups the designated elements into groups satisfying the following conditions.

Condition 1: One element certainly belongs to one group. One element does not belong to a plurality of groups.

Condition 2: One group includes one or more elements in the first element group and one or more elements in the second element group.

Condition 3: Each group includes only one element in the first element group or only one element in the second element group.

Figure 55:
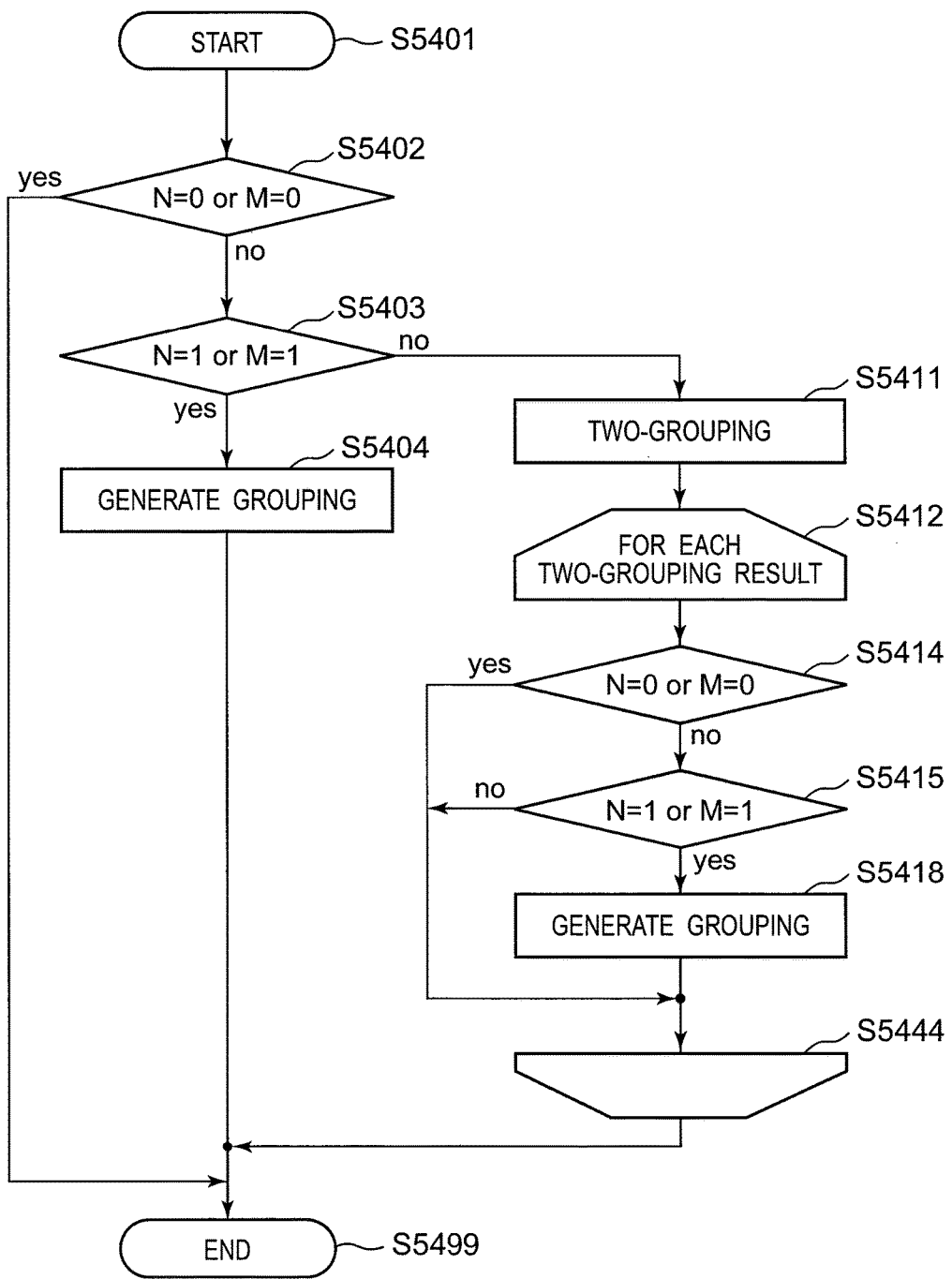
FIG. 55 is flowchart of a grouping unit according to the third embodiment.

FIG. 55 is a flowchart of a flow of the processes executed by the grouping main unit 7202.

Initially in step S5401, the grouping main unit 7202 starts grouping the first element group F {F_1, F_2, . . . , and F_M} and the second element group S {S_1, S_2, . . . , and S_N} having been designated.

Subsequently in step S5402, the grouping main unit 7202 decides whether or not the number M of elements in the first element group has the value "0", or whether or not the number N of elements in the second element group has the value "0". If any one of the number M and the number N is "0", the flow branches to step S5499 and ends the processes. Otherwise, the flow branches to step S5403.

Subsequently in step S5403, the grouping main unit 7202 decides whether or not the number M of elements in the first element group has the value "1", or whether or not the number N of elements in the second element group has the value "1". If any one of the number M and the number N is "1", the flow branches to step S5404. Otherwise, the flow branches to step S5411.

Then in step S5404, the grouping main unit 7202 forms a group including all the elements {F_1, F_2, . . . , and F_M} in the first element group and all the elements {S_1, S_2, . . . , and S_N} in the second element group, and outputs the group [{F_1, F_2, . . . , and F_M}, {S_1, S_2, . . . , and S_N}] as a result of the processes of the grouping main unit 7202, and ends the processes in step S5499.

For example, in a case where the first element group F includes {1, 2} and the second element group S includes {1}, a group [{1, 2}, {1}] is output. In another case where the first element group F includes {1} and the second element group S includes {2}, a group [{1}, {2}] is output.

In step S5411, the grouping main unit 7202 causes the two-grouping unit 7203 to execute the process. More specifically, the two-grouping unit 7203 acquires a two-grouping result indicated in FIG. 54, for example.

The grouping main unit 7202 executes the looping processes from steps S5412 to S444 to each grouping result acquired by execution of the two-grouping unit 7203. In the case of FIG. 54, the looping processes from steps S5412 to S444 are executed to the grouping in each row in FIG. 54.

Then in step S5414, the grouping main unit 7202 performs condition decision to a group 0 generated by two-grouping. More specifically, the grouping main unit 7202 decides whether or not the following condition is satisfied.

Condition: The number of elements in the first element group is "0" or the number of elements in the second element group is "0".

If the grouping main unit 7202 decides that the condition of step S5414 is satisfied, the flow branches to step S5444. If the grouping main unit 7202 decides that the condition of step S5414 is not satisfied, the flow branches to step S5415.

The group 0 includes an element group with the number of elements of "0" in Nos. "3, 7, 11, and 15" in FIG. 54. The flow thus branches to step S5444.

The group 1 includes an element group with the number of elements of "0" in Nos. "1, 2, (3,) 4, 8, and 12" in FIG. 54. The flow thus branches to step S5444.

Otherwise, namely, in Nos. "5, 6, 9, 10, 13, and 14", the flow branches to step S5415.

In step S5415, the grouping main unit 7202 performs condition decision to the group 0 generated by two-grouping. More specifically, the grouping main unit 7202 decides whether or not the following condition is satisfied.

Condition: The number of elements in the first element group is "1" or the number of elements in the second element group is "1".

If the grouping main unit 7202 decides that the condition is satisfied, the flow branches to step S5418. If the grouping main unit 7202 decides that the condition is not satisfied, the flow branches to step S5444.

The flow branches to step S5418 in Nos. "5, 6, 9, 10, 13, and 14" in FIG. 54.

In step S5418, the grouping main unit 7202 generates grouping for the group 0 that is generated by two-grouping, and stores the grouping in the grouping storage 5204.

Figure 56:
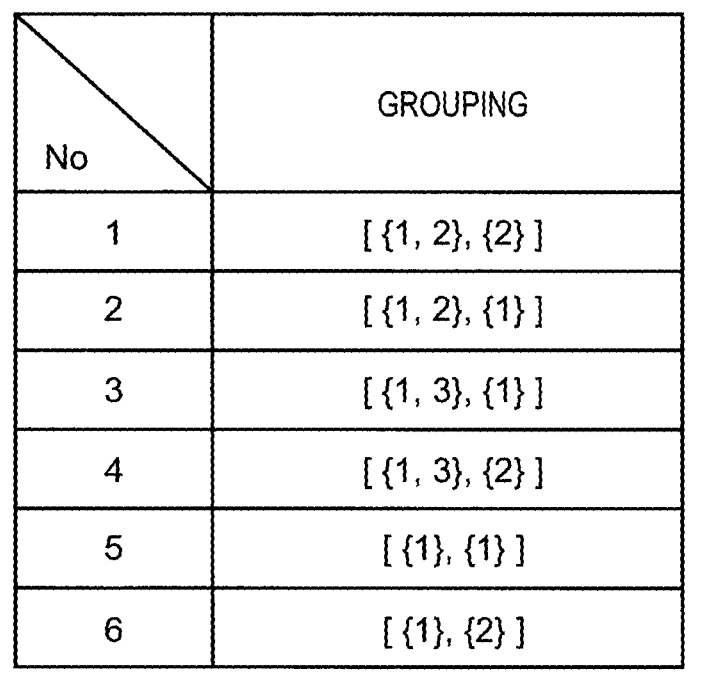

FIG. 56 indicates grouping generated in step S5418 in Nos. "5, 6, 9, 10, 13, and 14" in FIG. 54.

The grouping main unit 7202 executes the processes as described above.

The grouping storage 5204 holds a set of groupings Gw (w=1, 2, . . . , and W; where W is the number of groupings) acquired by the grouping acquiring unit 5203. A grouping is added every time the grouping main unit 7202 executes the process in step S5404 or S5418.

Figure 57:
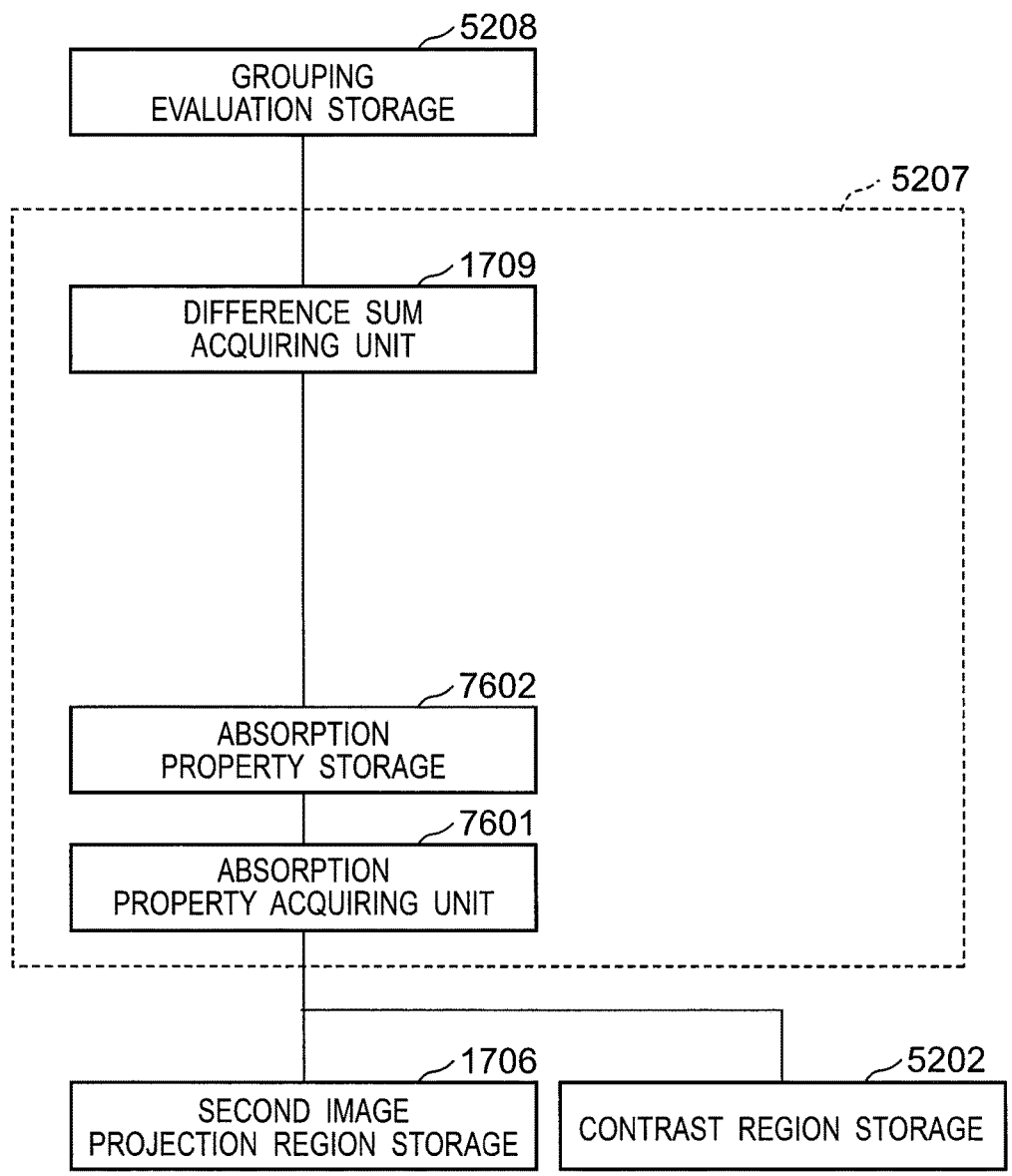
FIG. 57 is a view of the configuration of a grouping evaluator according to the third embodiment.

The grouping evaluator 5207 acquires evaluation values Hw (w=1, 2, . . . , and W) for the respective groupings Gw (w=1, 2, . . . , and W) held by the grouping storage 5204, and stores the acquired evaluation values in the grouping evaluation storage 5208. FIG. 57 is a view of the configuration of the grouping evaluator 5207. The grouping evaluator 5207 includes an absorption property acquiring unit 7601, an absorption property storage 7602, and a difference sum acquiring unit 1709. The difference sum acquiring unit 1709 will not be described because the difference sum acquiring unit 1709 performs difference summing similar to that of the absorption property evaluator 1709 according to the second embodiment.

The absorption property acquiring unit 7601 acquires chronological total absorption properties of all the regions in the first image projection regions Pk_m (m=1, 2, . . . , and M) belonging to the designated grouping Gw and chronological total absorption properties of all the regions in the second image projection regions Qk_n (n=1, 2, . . . , and N) held by the second image projection region storage 1706.

The absorption property storage 7602 holds absorption properties acquired by the absorption property acquiring unit 7601. In accordance with the absorption properties held by the absorption property storage 7602, the difference sum acquiring unit 1709 performs difference summing similar to that of the absorption property evaluator 1709 according to the second embodiment, and transmits the evaluation values Hw (w=1, 2, . . . , and W) to the grouping evaluation storage 5208.

The grouping evaluation storage 5208 holds the evaluation values Hw (w=1, 2, . . . , and W) acquired by the grouping evaluator 5207.

The corresponding region determiner 5209 selects a minimum evaluation value Hx from the evaluation values held by the grouping evaluation storage 5208.

Figure 58:
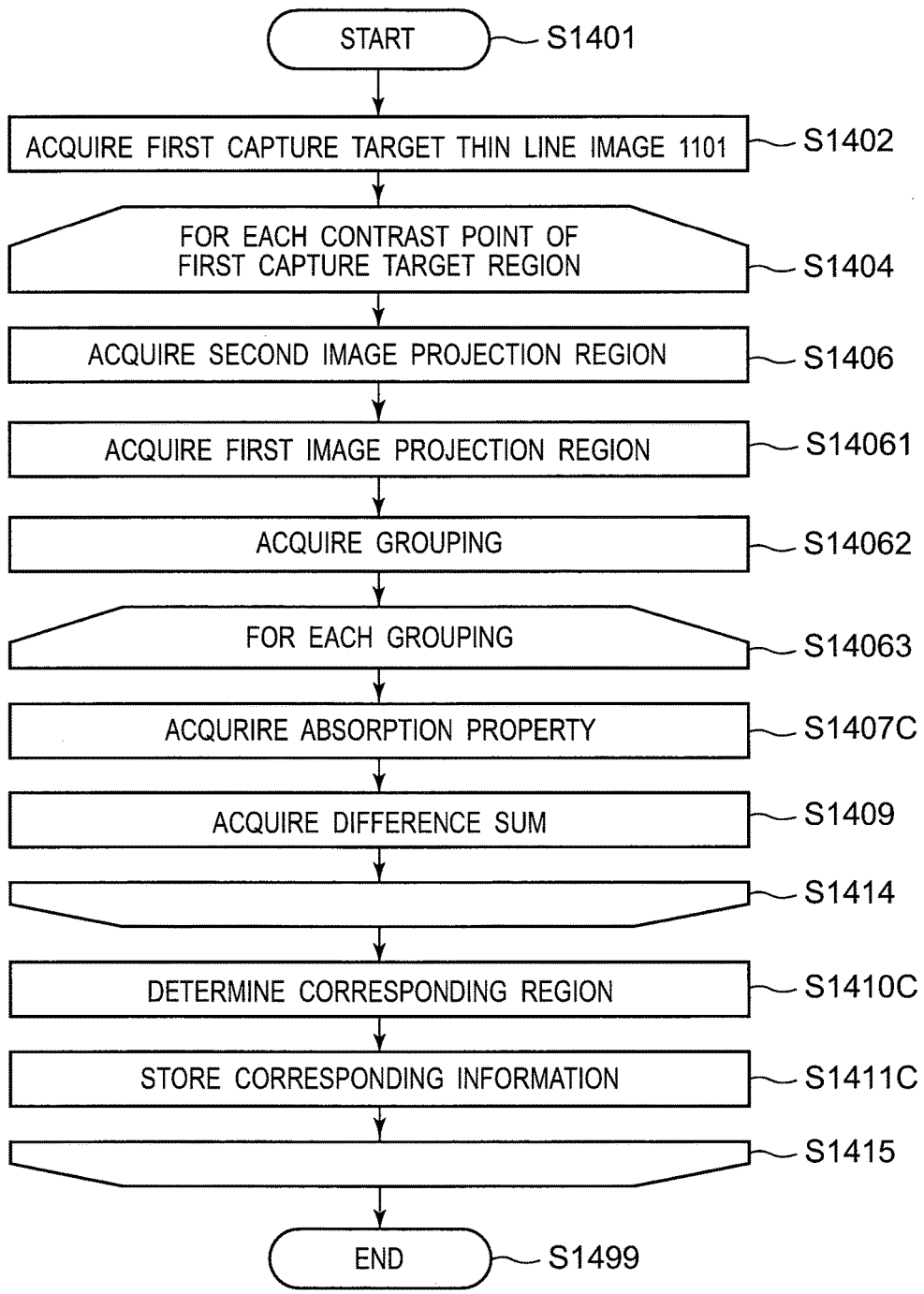
FIG. 58 is a flowchart of the processes executed by an absorption property acquiring unit according to the third embodiment.

A mapping controller 5210 controls the respective units in the mapping unit 107C to perform mapping. FIG. 58 is a flowchart of a flow of the processes executed by the mapping controller 5210.

The mapping controller 5210 starts the processes in step S1401.

Subsequently in step S1402, the mapping controller 5210 acquires the first capture target thin line image 1101T from the capture target thin line image storage 106.

The mapping controller 5210 executes the processes in steps S1404 to S1415 to a black point (s) in the capture target region on the first capture target thin line image 1101T acquired in step S1402. Assume in the following description that the black point corresponds to each of the first image projection points Pk (k=1, 2, . . . , and K; where k is the number of black points).

Then in step S1406, the mapping controller 5210 causes the second image projection region acquiring unit 1705 to acquire the second image projection regions Qk_n=1, 2, . . . , and N) for the first image projection point Pk and store coordinates of the acquired second image projection regions Qk_n (n=1, 2, . . . , and N) in the second image projection region storage 1706.

In step S14061, the mapping controller 5210 causes the first image projection region acquiring unit 1702 to acquire the first image projection regions Pk_m ((m=1, 2, . . . , and M) included in the epipolar plane including the first image projection point Pk and store coordinates of the acquired first image projection regions Pk_m ((m=1, 2, . . . , and M) in the first image projection region storage 1703.

Then in step S14062, the mapping controller 5210 commands the grouping acquiring unit 5203 to execute the process. More specifically, the grouping acquiring unit 5203 generates the groupings Gw (w=1, 2, . . . , and W) for the first image projection regions Pk_m (m=1, 2, . . . , and M) and the second image projection regions Qk_n (n=1, 2, . . . , and N).

The mapping controller 5210 executes the processes in steps S14063 to S1414 to the results of the groupings Gw (w=1, 2, . . . , and W) acquired in step S14062.

In step S1407C, the mapping controller 5210 commands the absorption property acquiring unit 7601 to execute the process. More specifically, the absorption property acquiring unit 7601 acquires the chronological total absorption properties of the first image projection points Pk_m (m=2, 1, . . . , and M) belonging to the grouping Gw and the chronological total absorption properties of the second image projection regions Qk_n (n=1, 2, . . . , and N) belonging to the grouping Gw, and stores the acquired absorption properties in the absorption property storage 7602.

Subsequently in step S1409, the mapping controller 5210 commands the difference sum acquiring unit 1709 to execute the process. More specifically, the difference sum acquiring unit 1709 calculates, as an evaluation value, the sum Hw of differences at respective times between the total absorption properties of the first image projection regions Pk_m and the total absorption properties of the second image projection regions Qk_n, stores the sum Hw in the grouping evaluation storage 5208, and ends.

Then in step S1410C, the mapping controller 5210 commands the corresponding region determiner 5209 to execute the process. More specifically, the corresponding region determiner 5209 acquires a minimum evaluation value Ha from the evaluation values Hw (w=1, 2, . . . , and W) held by the grouping evaluation storage 5208. Reference sign a denotes the grouping number corresponding to the selected evaluation value.

Then in step S1411C, the mapping controller 5210 stores, in the corresponding information storage 108, coordinates of gravity centers of the first image projection regions Pk_m (m=1, 2, . . . , and M) and coordinates of gravity centers of the second image projection regions Qk_n (n=1, 2, . . . , and N) belonging to a grouping Gα, as well as the evaluation value Hα, and ends the process in step S1415.

FIG. 59 indicates corresponding information to be added in a case where the grouping Gα includes a plurality of first image projection regions Pk_m. As indicated in FIG. 59, the corresponding information storage 108 stores rows each including the second image region Qk_1 as the corresponding region of the first image regions Pk_m (m=1, 2, . . . , and M). In FIG. 59, coordinates of the gravity center of a first image projection region Pk_k are expressed as (Pk_m_X, Pk_m_Y). Furthermore, coordinates of the gravity center of a second image projection region Qk_k are expressed as (Qk_n_X, Qk_n_Y).

FIG. 60 indicates corresponding information to be added in a case where the grouping Gα includes a plurality of second image projection regions Qk_n. As indicated in FIG. 60, the corresponding information storage 108 stores rows each including one of the second image regions Qk_n (n=1, 2, . . . , and N) as the corresponding region of the first image region Pk_1.

The mapping controller 5210 ends the processes in step S1499.

Effects of Third Embodiment

The third embodiment exerts effects similar to those of the second embodiment.

Fourth Embodiment

Described in the third embodiment is the exemplary flow of the processes. Alternatively, the order of the processes can be changed, or a plurality of processes can be executed parallelly (simultaneous parallel processing).

The elements included in the shape restoring apparatuses 1 and 1C can be partially or entirely configured to be actually a computer system that includes, for example, a microprocessor, ROM, RAM, hard disk unit, display unit, keyboard, mouse, and the like. A computer program is stored on the RAM or the hard disk unit. Functions of each of the apparatuses can be achieved by the microprocessor operating according to the computer program. The computer program mentioned here is a combination of a plurality of instruction codes that indicate commands to a computer for achieving predetermined functions.

The elements included in the shape restoring apparatuses 1 and 1C can be partially or entirely configured by one system large scale integration (LSI). A system LSI is a super-multifunctional LSI that includes a plurality of the configurations integrated on one chip, more particularly, is a computer system including a microprocessor, a ROM, a RAM, and the like. A computer program is stored in the RAM. The system LSI realizes its function when the microprocessor operates in accordance with the computer program.

The elements included in the shape restoring apparatuses 1 and 1C can be partially or entirely configured by an IC card or a monolithic module detachably attached to a corresponding apparatus. The IC card or the module is a computer system including a microprocessor, a ROM, a RAM, and the like. The IC card or the module can alternatively include the super-multifunctional LSI. The IC card or the module realizes its function when the microprocessor operates in accordance with the computer program. The IC card or the module can alternatively have the tamper resistant property.

The elements included in the shape restoring apparatuses 1 and 1C are partially or entirely applicable to methods of acquiring a tube shape. The present disclosure can be embodied by a computer program configured to cause a computer to acquire a tube shape, or digital signals configured by a computer program in accordance with the methods.

The elements included in the shape restoring apparatuses 1 and 1C can be partially or entirely embodied when recorded in a recording medium configured to cause a computer to read the computer program or the digital signals, such as a flexible disk, a hard disk, a CD-ROM, an MO, a DVD, a DVD-ROM, a DVD-RAM, a Blu-ray (registered trademark) disc (BD), or a semiconductor memory. These can be embodied by digital signals recorded in the recording medium.

The elements included in the shape restoring apparatuses 1 and 1C can be partially or entirely embodied by the computer program or the digital signals that are transmitted through a telecommunication line, a wireless communication line, a wired communication line, a network represented by the Internet, data broadcasting, or the like.

The elements included in the shape restoring apparatuses 1 and 1C can be partially or entirely embodied by a computer system including a microprocessor and a memory. Such a memory stores the computer program, and the microprocessor operates in accordance with the computer program.

Another independent computer system can execute the processes according to the present disclosure by transfer of the computer program or the digital signals that is recorded in a recording medium, or transfer of the computer program or the digital signals by way of a network or the like.

By properly combining the arbitrary embodiment (s) or modification (s) of the aforementioned various embodiments and modifications, the effects possessed by the embodiment (s) or modification (s) can be produced.

INDUSTRIAL APPLICABILITY

The image region mapping device, the 3D model generating apparatus, the image region mapping method, and the image region mapping program according to one of the aspects of the present disclosure enable mapping of a plurality of image regions in X-ray images of a blood vessel captured in two directions as well as generation of a 3D model in accordance with the mapping result, and are thus useful for catheterization and the like.

The entire disclosure of Japanese Patent Application No. 2013-079218 filed on Apr. 5, 2013, including specification, claims, drawings, and summary are incorporated herein by reference in its entirety.

Although the present disclosure has been fully described in connection with the embodiments thereof with reference to the accompanying drawings, it is to be noted that various changes and modifications are apparent to those skilled in the art. Such changes and modifications are to be understood as included within the scope of the present disclosure as defined by the appended claims unless they depart therefrom.

What is claimed is:

1. An image region mapping device configured to map a plurality of image regions of a blood vessel, the device comprising:
   an X-ray image acquiring unit configured to, by irradiating the blood vessel through which a contrast medium is passing with X-rays at first and second photographing angles different from each other, acquire an X-ray image set including a first X-ray image at the first photographing angle and a second X-ray image at the second photographing angle;
   a first X-ray absorption property acquiring unit configured to acquire, as an absorption property, an absorbed X-ray amount in a first image region corresponding to a portion of the blood vessel in the first X-ray image, from brightness of the contrast medium;
   a second X-ray absorption property acquiring unit configured to acquire, as an absorption property, an absorbed X-ray amount in each of a plurality of second image regions corresponding to a portion of the blood vessel in the second X-ray image as candidate corresponding image regions of the first image region, from brightness of the contrast medium;
   a similarity degree calculator configured to calculate a similarity degree between the absorbed X-ray amount acquired by the first X-ray absorption property acquiring unit and each of the plurality of absorbed X-ray amounts acquired by the second X-ray absorption property acquiring unit; and
   a corresponding region determiner configured to determine one of the second image regions corresponding to the first image region in accordance with the similarity degrees calculated by the similarity degree calculator.

2. The image region mapping device according to claim 1, further comprising:
   a radiographing unit information acquiring unit configured to acquire relative positional information between positional information on a first radiographing unit configured to capture the blood vessel at the first photographing angle and positional information on a second radiographing unit configured to capture the blood vessel at the second photographing angle;
   a capture target region acquiring unit configured to acquire positional information on the first image region on the first X-ray image; and
   a second image projection region acquiring unit configured to calculate an epipolar plane defined by the first radiographing unit, the second radiographing unit, and the first image region from the positional information acquired by each of the radiographing unit information acquiring unit and the capture target region acquiring unit, calculate an epipolar line as an intersection line between the calculated epipolar plane and the second X-ray image on the second X-ray image, and acquire positional information on a position on the calculated epipolar line for each of the plurality of second image regions, wherein
   the second X-ray absorption property acquiring unit acquires an absorption property at the position of the positional information on each of the plurality of second image regions acquired by the second image projection region acquiring unit.

3. The image region mapping device according to claim 2, wherein
the first X-ray absorption property acquiring unit acquires, as the absorption property, the absorbed X-ray amount in the first image region from a difference between a product of logarithms of a number of pixels in the first image region and intensity of an X-ray emitted from the first radiographing unit and logarithm sums of intensity of X-rays emitted from the first radiographing unit and acquired at the respective pixels in the first image region, and
the second X-ray absorption property acquiring unit acquires, as the absorption property, the absorbed X-ray amount in each of the plurality of second image regions from a difference between a product of logarithms of a number of pixels in the corresponding second image region and intensity of an X-ray emitted from the second radiographing unit and a logarithm sum of intensity of X-rays emitted from the second radiographing unit and acquired at the respective pixels in the corresponding second image region.

4. The image region mapping device according to claim 1, wherein
the first X-ray absorption property acquiring unit acquires, as the absorption property, a change in absorbed X-ray amount in the first image region from brightness of the contrast medium for a predetermined time period,
the second X-ray absorption property acquiring unit acquires, as the absorption property, a change in absorbed X-ray amount in each of the plurality of second image regions from brightness of the contrast medium for the predetermined time period, and
the similarity degree calculator calculates a similarity degree between the change in absorbed X-ray amount acquired by the first X-ray absorption property acquiring unit and each of the plurality of changes in absorbed X-ray amount acquired by the second X-ray absorption property acquiring unit.

5. The image region mapping device according to claim 2, wherein
the first X-ray absorption property acquiring unit acquires, as the absorption property, a change in absorbed X-ray amount in the first image region from brightness of the contrast medium for a predetermined time period,
the second X-ray absorption property acquiring unit acquires, as the absorption property, a change in absorbed X-ray amount in each of the plurality of second image regions from brightness of the contrast medium for the predetermined time period, and
the similarity degree calculator calculates a similarity degree between the change in absorbed X-ray amount acquired by the first X-ray absorption property acquiring unit and each of the plurality of changes in absorbed X-ray amount acquired by the second X-ray absorption property acquiring unit.

6. The image region mapping device according to claim 3, wherein
the first X-ray absorption property acquiring unit acquires, as the absorption property, a change in absorbed X-ray amount in the first image region from brightness of the contrast medium for a predetermined time period,
the second X-ray absorption property acquiring unit acquires, as the absorption property, a change in absorbed X-ray amount in each of the plurality of second image regions from brightness of the contrast medium for the predetermined time period, and
the similarity degree calculator calculates a similarity degree between the change in absorbed X-ray amount acquired by the first X-ray absorption property acquiring unit and each of the plurality of changes in absorbed X-ray amount acquired by the second X-ray absorption property acquiring unit.

7. The image region mapping device according to claim 2, wherein
the X-ray image acquiring unit acquires an X-ray image set including the first X-ray image and the second X-ray image at each of first and second predetermined times different from each other,
the first X-ray absorption property acquiring unit acquires, as the absorption property, the absorbed X-ray amount in the first image region from a difference between a logarithm sum of intensity of X-rays emitted from the first radiographing unit and acquired at the respective pixels in the first image region at the first predetermined time and logarithm sums of intensity of X-rays emitted from the first radiographing unit and acquired at the respective pixels in the first image region at the second predetermined time, and
the second X-ray absorption property acquiring unit acquires, as the absorption property, the absorbed X-ray amount in each of the plurality of second image regions from a difference between logarithm sums of intensity of X-rays emitted from the second radiographing unit and acquired at the respective pixels in the corresponding second image region at the first predetermined time, and logarithm sums of intensity of X-rays emitted from the second radiographing unit and acquired at the respective pixels in the corresponding second image region at the second predetermined time.

8. The image region mapping device according to claim 1, wherein
the first X-ray absorption property acquiring unit acquires, as the absorption property, the absorbed X-ray amount in the first image region from a value obtained by dividing a product of intensities of X-rays emitted from the first radiographing unit and acquired at the respective pixels in the first image region by a value obtained by multiplying intensity of an X-ray emitted from the first radiographing unit and a number of pixels in the first image region, and
the second X-ray absorption property acquiring unit acquires, as the absorption property, the absorbed X-ray amount in each of the plurality of second image regions from a value obtained by dividing a product of intensities of X-rays emitted from the second radiographing unit and acquired at the respective pixels in the corresponding second image region by a value obtained by multiplying intensity of an X-ray emitted from the second radiographing unit and a number of pixels in the corresponding second image region.

9. The image region mapping device according to claim 2, wherein
the first X-ray absorption property acquiring unit acquires, as the absorption property, the absorbed X-ray amount in the first image region from a value obtained by dividing a product of intensities of X-rays emitted from the first radiographing unit and acquired at the respective pixels in the first image region by a value obtained by multiplying intensity of an X-ray emitted from the first radiographing unit and a number of pixels in the first image region, and the second X-ray absorption property acquiring unit acquires, as the absorption property, the absorbed X-ray amount in each of the plurality of second image regions from a value obtained by dividing a product of intensities of X-rays emitted from the second radiographing unit and acquired at the respective pixels in the corresponding second image region by a value obtained by multiplying intensity of an X-ray emitted from the second radiographing unit and a number of pixels in the corresponding second image region.

10. The image region mapping device according to claim 2, wherein the X-ray image acquiring unit acquires an X-ray image set including the first X-ray image and the second X-ray image at each of first and second predetermined times different from each other, the first X-ray absorption property acquiring unit acquires, as the absorption property, the absorbed X-ray amount in the first image region from a value obtained by dividing a product of intensities of X-rays emitted from the first radiographing unit and acquired at the respective pixels in the first image region at the first predetermined time by a product of intensities of X-rays emitted from the first radiographing unit and acquired at the respective pixels in the first image region at the second predetermined time, and the second X-ray absorption property acquiring unit acquires, as the absorption property, the absorbed X-ray amount in each of the plurality of second image regions from a value obtained by dividing a product of intensities of X-rays emitted from the second radiographing unit and acquired at the respective pixels in the corresponding second image region at the first predetermined time by a product of intensities of X-rays emitted from the second radiographing unit and acquired at the respective pixels in the corresponding second image region at the second predetermined time.

11. A 3D model generating apparatus configured to generate a 3D model of the blood vessel having a bifurcation, the apparatus comprising:

the image region mapping device according to claim 1, in which the second X-ray absorption property acquiring unit acquires, as an absorption property, from brightness of the contrast medium, an absorbed X-ray amount in each of a plurality of second image regions corresponding to the bifurcation of the blood vessel in the second X-ray image as candidate corresponding image regions of the first image region; and a 3D model generator configured to generate the 3D model of the blood vessel in accordance with information determined by the image region mapping device.

12. An image region mapping method of mapping a plurality of image regions of a blood vessel, the method comprising:

by irradiating the blood vessel through which a contrast medium is passing with X-rays of equal intensity at first and second photographing angles different from each other, with an X-ray image acquiring unit, acquiring an X-ray image set including a first X-ray image at the first photographing angle and a second X-ray image at the second photographing angle;

with a first X-ray absorption property acquiring unit, acquiring, as an absorption property, an absorbed X-ray amount in a first image region corresponding to a portion of the blood vessel in the first X-ray image, from brightness of the contrast medium;

with a second X-ray absorption property acquiring unit, acquiring, as an absorption property, an absorbed X-ray amount in each of a plurality of second image regions corresponding to a portion of the blood vessel in the second X-ray image as candidate corresponding image regions of the first image region, from brightness of the contrast medium;

with a similarity degree calculator, calculating a similarity degree between the absorbed X-ray amount acquired by the first X-ray absorption property acquiring unit and each of the plurality of absorbed X-ray amounts acquired by the second X-ray absorption property acquiring unit; and with a corresponding region determiner, determining the second image region having a maximum similarity degree out of the similarity degrees calculated by the similarity degree calculator as a corresponding region of the first image region.

13. A non-transitory computer-readable recording medium including an image region mapping program configured to map a plurality of image regions of a blood vessel, the program causing a computer to function as:

an X-ray image acquiring unit configured to, by irradiating the blood vessel through which a contrast medium is passing with X-rays at first and second photographing angles different from each other, acquire an X-ray image set including a first X-ray image at the first photographing angle and a second X-ray image at the second photographing angle;

a first X-ray absorption property acquiring unit configured to acquire, as an absorption property, an absorbed X-ray amount in a first image region corresponding to a portion of the blood vessel in the first X-ray image, from brightness of the contrast medium;

a second X-ray absorption property acquiring unit configured to acquire, as an absorption property, an absorbed X-ray amount in each of a plurality of second image regions corresponding to a portion of the blood vessel in the second X-ray image as candidate corresponding image regions of the first image region, from brightness of the contrast medium;

a similarity degree calculator configured to calculate a similarity degree between the absorbed X-ray amount acquired by the first X-ray absorption property acquiring unit and each of the plurality of absorbed X-ray amounts acquired by the second X-ray absorption property acquiring unit; and a corresponding region determiner configured to determine one of the second image regions corresponding to the first image region in accordance with the similarity degrees calculated by the similarity degree calculator.

* * * * *